United States Patent
Pfeifer et al.

(10) Patent No.: US 10,858,426 B2
(45) Date of Patent: Dec. 8, 2020

(54) IL-18 BINDING PROTEIN (IL-18BP) IN INFLAMMATORY DISEASES

(71) Applicant: AB2 BIO SA, Lausanne (CH)

(72) Inventors: Andrea Pfeifer, St-Legier-la Chiesaz (CH); Greg Del Val, Rolle (CH)

(73) Assignee: AB2 BIO SA, Lausanne (CH)

( * ) Notice: Subject to any disclaimer, the term of this patent is extended or adjusted under 35 U.S.C. 154(b) by 1 day.

(21) Appl. No.: 14/916,917

(22) PCT Filed: Sep. 5, 2014

(86) PCT No.: PCT/EP2014/069013
§ 371 (c)(1),
(2) Date: Mar. 4, 2016

(87) PCT Pub. No.: WO2015/032932
PCT Pub. Date: Mar. 12, 2015

(65) Prior Publication Data
US 2016/0215048 A1    Jul. 28, 2016

(30) Foreign Application Priority Data
Sep. 5, 2013 (EP) .................................. 13183193

(51) Int. Cl.
| | |
|---|---|
| C07K 16/24 | (2006.01) |
| G01N 33/68 | (2006.01) |
| C07K 14/54 | (2006.01) |
| C07K 14/715 | (2006.01) |
| G01N 33/564 | (2006.01) |
| C07K 14/705 | (2006.01) |
| A61K 39/00 | (2006.01) |

(52) U.S. Cl.
CPC ............ C07K 16/244 (2013.01); C07K 14/54 (2013.01); C07K 14/7155 (2013.01); G01N 33/564 (2013.01); G01N 33/6869 (2013.01); A61K 2039/505 (2013.01); C07K 14/705 (2013.01); C07K 2317/76 (2013.01); C07K 2317/92 (2013.01); G01N 2333/54 (2013.01); G01N 2800/105 (2013.01); G01N 2800/205 (2013.01); G01N 2800/50 (2013.01); G01N 2800/52 (2013.01)

(58) Field of Classification Search
CPC . C07K 16/244; G01N 33/564; G01N 33/6869
See application file for complete search history.

(56) References Cited

U.S. PATENT DOCUMENTS

| | | | |
|---|---|---|---|
| 9,255,144 B2* | 2/2016 | Dobson ................ | C07K 16/244 |
| 9,376,489 B2* | 6/2016 | Bardroff ............... | C07K 16/244 |
| 2002/0098185 A1 | 7/2002 | Sims | |
| 2004/0076628 A1 | 4/2004 | Chvatchko et al. | |
| 2004/0234523 A1* | 11/2004 | Dinarello ............... | C07K 14/54 |
| | | | 424/145.1 |
| 2005/0064541 A1 | 3/2005 | Novick et al. | |
| 2005/0100965 A1 | 5/2005 | Ghayur et al. | |
| 2005/0147610 A1 | 7/2005 | Ghayur et al. | |
| 2013/0004416 A1 | 1/2013 | Wu | |
| 2013/0072441 A1 | 3/2013 | Hoshino | |
| 2014/0004128 A1* | 1/2014 | Dobson ................ | C07K 16/244 |
| | | | 424/158.1 |
| 2014/0112915 A1* | 4/2014 | Bardroff ............... | C07K 16/244 |
| | | | 424/133.1 |
| 2016/0215048 A1 | 7/2016 | Pfeifer et al. | |

FOREIGN PATENT DOCUMENTS

| | | |
|---|---|---|
| AU | 2011224023 C1 | 8/2013 |
| CL | 200100316 | 1/2001 |
| CL | 200701478 | 12/2007 |
| EP | 2161032 A2 | 3/2010 |
| JP | 2008541748 A | 11/2008 |
| JP | 2009102354 A | 5/2009 |
| JP | 2014508511 A | 4/2014 |
| WO | 0158956 A2 | 8/2001 |
| WO | 0162285 A1 | 8/2001 |
| WO | 2001062285 A1 | 8/2001 |
| WO | 0158956 A3 | 3/2002 |
| WO | 0232374 A2 | 4/2002 |
| WO | 02060479 A1 | 8/2002 |
| WO | 2002060479 A1 | 8/2002 |
| WO | 02096456 A1 | 12/2002 |
| WO | 2004101617 A1 | 11/2004 |
| WO | 2005087249 A1 | 9/2005 |
| WO | 2007030949 A2 | 3/2007 |
| WO | 2012085015 A1 | 6/2012 |
| WO | 2014037899 A2 | 3/2014 |
| WO | 2015032932 A1 | 3/2015 |
| WO | 2016139297 A1 | 9/2016 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
International Search Report for PCT/EP2014/059013, dated Jan. 8, 2015, 8 pages.
Dinarello, et al., "Interleukin-18 and IL-18 Binding Protein", Frontiers in Immunology, vol. 4, Jan. 1, 2013, 10.

(Continued)

*Primary Examiner* — Bridget E Bunner
*Assistant Examiner* — Fozia Hamud
(74) *Attorney, Agent, or Firm* — F. Brent Nix, Esq.; Johnson, Marcou, Isaacs & Nix, LLC

(57) ABSTRACT

The present invention provides means and methods for treating Interleukin 18 (IL-18)-associated diseases and disorders. In particular, the present invention discloses antibodies specific for free IL-18 and IL-18 Binding Protein (IL-18BP) for use in such treatments and for the diagnosis of the indications.

5 Claims, 23 Drawing Sheets
Specification includes a Sequence Listing.

(56) References Cited

OTHER PUBLICATIONS

Lochner, et al., "Anti-Interleukin-18 Therapy in Murine Models of Inflammatory Bowel Disease", Pathobiology, vol. 70, No. 3, Jan. 1, 2002, 164-169.
Lochner, et al., "Generation of Neutralizing Mouse Anti-Mouse IL-18 Antibodies for Inhibition of Inflammatory Responses In Vivo", Journal of Immunological Methods, Jan. 1, 2002, 149-157.
Novick, et al., "High Circulating Levels of Free Interleukin-18 in Patients with Active SLE in the Presence of Elevated Levels of Interleukin-18 Binding Protein", Journal of Autoimmunity, vol. 34, No. 2, Mar. 1, 2010, 121-126.
Thompson, et al., "Free Interleukin (IL)-18 Levels, and the Impact of IL18 and IL18BP Genetic Variation, in CHD Patients and Healthy Men", Arteriosclerosis, Thrombosis, and Vascular Biology, vol. 27, No. 12, Dec. 1, 2007, 2743-2749.
Efthimiou, P. et al., "Diagnosis and Management of Adult Onset Still's Disease", Ann Rheum Dis, vol. 65, 2006, 564-572.
Jordan, J. et al., "Role of IL-18 in Acute Lung Inflammation", The Journal of Immunology, vol. 167, 2001, 7060-7068.
Wong, et al., "Elevation of Plasma Interleukin-18 Concentration Is Correlated with Disease Activity in Systemic Lupus Erythematosus", Rheumatology (Oxford), vol. 39, 2000, 1078-1081.
Wright, "Animal Models of Chronic Obstructive Disease.", Am J Physiol Lung Cell Mol Physiol, 2008, L1-L15.
Zhang, et al., "Isolation of Lymphocytes and Their Innate Immune Characterizations from Liver, Intestine, Lung and Uterus", Cell Mol Immunol, vol. 2, 2005, 271-280.
Zheng, et al., "Inducible Targeting of IL-13 to the Adult Lung Causes Matrix Metalloproteinase- and Cathepsin-Dependent Emphysema", J Clin Invest, vol. 106, 2000, 1081-1093.
Zheng, et al., "Role of Cathepsin S-Dependent Epithelial Cell Apoptosis in IFN-Gamma-Induced Alveolar Remodeling and Pulmonary Emphysema", J Immunol, vol. 174, 2005, 8106-8115.
Colombian Office Action for Colombian Patent Application No. 16-077.559, dated Jan. 2018, 12.
Japanese Office Action for Japanese Patent Application No. 2016-539564 (English-language translation provided), dated Mar. 1, 2018, 1-13.
Chilean Office Action for Chilean Patent Application No. 0506-2016 (English-language translation included), dated Aug. 9, 2017, 16.
Argiriadi, et al., "Unusual Water-Mediated Antigenic Recognition of the Proinflammatory Cytokine Interleukin-18", J. Biol Chem, 2009, 24478-24489.
Azoulay, et al., "Granulocyte colony-stimulating factor enhances alpha-naphthylthiourea-induced pulmonary hypertension", J Appl Physiol, vol. 94, 2003, 2027-2033.
Baron, et al., "Genetically manipulated mouse models of lung disease: potential and pitfalls", Am J Physiol Lung Cell Mol Physiol, 2012, L485-L497.
Cao, et al., "Multimodality Imaging of IL-18-Binding Protein-Fc Therapy for Experimental Lung Metastasis", Cancer Therapy: Preclinical, vol. 14, No. 19, 2008, 6137-6145.
Chen, et al., "Predominance of Th1 cytokine in peripheral blood and pathological tissues of patients with active untreated adult onset Still's disease", Ann Rheum Dis, vol. 63, No. 10, 2004, 1300-1306.
Chen, et al., "Proinflammatory cytokine profiles in sera and pathological tissues of patients with active untreated adult onset Still's disease", J Rheumatol, vol. 31, 2004, 2189-2198.
Colafrancesco, et al., "IL-18 Serum Level in Adult Onset Still's Disease: A Marker of Disease Activity", International Journal of Inflammation, vol. 2012, Article ID No. 156890, 2012, 1-6.
Cunningham, "Tissue disaggregation", Methods Mol Biol, vol. 34, 1994, 225-228.
Daley, "Pulmonary arterial remodeling induced by a Th2 immune response", J Exp Med, vol. 205, 2008, 361-372.
Elias, et al., "Mechanistic heterogeneity in chronic obstructive pulmonary disease: insights from transgenic mice", Proc Am Thorac Soc, 2006, 494-498.

Eltom, et al., "P2X7 Receptor and Caspase-1 Activation Are Central to Airway Inflammation Observed after Exposure to Tobacco Smoke", PLoS ONE, vol. 6, No. 9, 2011, e24097.
Hackett, et al., "Clara cell secretory protein gene expression in bronchiolar epithelium", Am J Physiol, vol. 262, 1992, L399-L404.
Halbower, et al., "Agarose infiltration improves morphology of cryostat sections of lung", Lab Invest, vol. 71, 1994, 149-153.
Hautamaki, et al., "Requirement for macrophage elastase for cigarette smoke-induced emphysema in mice", Science, vol. 277, 1997, 2002-2004.
Hoshino, et al., "IL-18-transgenic mice: in vivo evidence of a broad role for IL-18 in modulating immune function", J Immunol, 2001, 7014-7018.
Hoshino, et al., "Pulmonary inflammation and emphysema: role of the cytokines IL-18 and IL-13", Am J Respir Crit Care Med, 2007, 49-62.
Hou, et al., "Humanization of an anti-CD34 monoclonal antibody by complementarity-determining region grafting based on computer-assisted molecular modeling", J Biochem, vol. 144, No. 1, Jul. 2008, 115-20.
Imaoka, et al., "Interleukin-18 production and pulmonary function in COPD", Eur Respir J, 2008, 287-97.
Jaatinen, et al., "Isolation of mononuclear cells from human cord blood by Ficoll-Paque density gradient", Curr Protoc Stem Cell Biol, Chapter 2:Unit 2A.1, 2007.
Kang, et al., "Cigarette smoke selectively enhances viral PAMP- and virus-induced pulmonary innate immune and remodeling responses in mice", J Clin Invest, vol. 118, 2008, 2771-2784.
Kang, et al., "IL-18 induces emphysema and airway and vascular remodeling via IFNγ, IL-17A, and IL-13", Am J Respir Crit Care Med, 2012, 1205-1217.
Kang, et al. "IL-18 is induced and IL-18 receptor alpha plays a critical role in the pathogenesis of cigarette smoke-induced pulmonary emphysema and inflammation", J Immunol, 2007, 1948-1959.
Kashmiri, et al., "SDR grafting—a new approach to antibody humanization", Methods, vol. 36, No. 1, May 2005, 25-34.
Kawashima, et al., "Levels of interleukin-18 and its binding inhibitors in the blood circulation of patients with adult-onset Still's disease", Arthritis Rheum, vol. 44, No. 3, 2001, 550-560.
Kim, et al., "Structural requirements of six naturally occurring isoforms of the IL-18 binding protein to inhibit IL-18", Proc Natl Acad Sci USA, vol. 97, No. 3, 2000, 1190-1195.
Kratzer, et al., "Role of IL-18 in second hand smoke-induced emphysema", Am J Respir Cell Mol Biol, vol. 48, No. 6, 2013, 725-32.
Lee, et al., "Role of breast regression protein 39 (BRP-39)/chitinase 3-like-1 in Th2 and IL-13-induced tissue responses and apoptosis", J Exp Med, vol. 206, 2009, 1149-1166.
Lee, et al., "Vascular endothelial growth factor (VEGF) induces remodeling and enhances TH2- mediated sensitization and inflammation in the lung", Nat Med 2004, vol. 10, 2004, 1095-1103.
Liu, et al., "Requirement for tumor necrosis factor-receptor 2 in alveolar chemokine expression depends upon the form of the ligand", Am J Respir Cell Mol Biol, vol. 33, 2005, 463-469.
Londhe, et al., "Systemic inflammatory profile and response to anti-tumor necrosis factor therapy in chronic obstructive pulmonary disease", Respir Res, 2012, 12.
Loza, et al., "Systemic Inflammatory Profile and Response to Anti-Tumor Necrosis Factor Therapy in Chronic Obstructive Pulmonary Disease", Respir Res, 2012, 12.
Ma, et al., "Role of CCR5 in IFN-γ-Induced And Cigarette Smoke-Induced Emphysema", J Clin Invest, vol. 115, 2005, 3460-3472.
Nakajima, et al., "The Master Regulator Driving Destructive and Remodeling Processes in the Lungs of Patients with Chronic Obstructive Pulmonary Disease?", Am J Respir Crit Care Med, 2012, 1137-1138.
Novick, et al., "A Novel IL-18BP ELISA Shows Elevated Serum IL-18BP In Sepsis and Extensive Decrease of Free IL-18", Cytokine, vol. 14, 2001, 334-342.
Park, et al., "Elevated interleukin-18 levels correlated with disease activity in systemic lupus erythematosus", Clin Rheumato, vol. 23, 2004, 225-229.

(56) References Cited

OTHER PUBLICATIONS

Petersen, et al., "Elevated Levels of IL-18 in Plasma and Skeletal Muscle in Chronic Obstructive Pulmonary Disease", Lung, 2007, 161-171.
Queen, et al., "A Humanized Antibody that Binds to the Interleukin 2 Receptor", Proc Natl Acad Sci U.S.A., vol. 86, No. 24, Dec. 1989, 10029-33.
Rastrick, et al., "Cigarette Smoke Induced Airway Inflammation Is Independent of NF-κB Signalling", PLoS ONE, vol. 8, No. 1, 2013, e54128.
Ray, et al., "Regulated Overexpression of Interleukin 11 in the Lung: Use to Dissociate Development-Dependent And -Independent Phenotypes", J Clin Invest, vol. 100, 1997, 2501-2511.
Reed, et al., "A Simple Method of Estimating 50% Endpoints", Am J Hyg, vol. 27, 1938, 493-497.
Riechmann, et al., "Reshaping Human Antibodies for Therapy", Nature, vol. 332, No. 6162, 1988, 332-323.
Rovina, et al., "Interleukin-18 in Induced Sputum: Association with Lung Function in Chronic Obstructive Pulmonary Disease", Respiratory Medicine, 2009, 1056-1062.
Shapiro, et al., "Transgenic and Gene-Targeted Mice as Models for Chronic Obstructive Pulmonary Disease", Eur J Respir, 2007, 375-378.
Sivakumar, et al., "Interleukin 18 Is a Primary Mediator of the Inflammation Associated with Dextran Sulphate Sodium Induced Colitis: Blocking Interleukin 18 Attenuates Intestinal Damage", Gut, vol. 50, No. 6, 2002, 812-820.
Taniguchi, et al., "Characterization of Anti-Human Interleukin-18 (IL-18)/Interferon-Gamma-Inducing Factor (IGIF) Monoclonal Antibodies and Their Application in the Measurement of Human IL-18 by ELISA", J Immunol Methods, vol. 206, 1997, 107-113.
Wang, et al., "Increased Expression of Interleukin-18 and its Receptor in Peripheral Blood of Patients with Chronic Obstructive Pulmonary Disease", COPD, vol. 9, No. 4, 2012, 375-381.
Wang, et al., "Interferon γ Induction of Pulmonary Emphysema in the Adult Murine Lung", J Exp Med, vol. 192, 2000, 1587-1600.
Wada, Taizo et al., "Sustained elevation of serum interleukin-18 and its association with hemophagocytic lymphohistiocytosis in XIAP deficiency", Cytokine, vol. 65, pp. 74-78, Available online: Sep. 29, 2013.
Canna, Scott et al., "An activating NLRC4 inflammasome mutation causes autoinflammation with recurrent macrophage activation syndrome", Nat Genet., vol. 46, No. 10, pp. 1140-1146, Oct. 2014.
Migliorini, Paola et al., "Free circulating interleukin-18 is increased in Schnitzler syndrome: a new autoinflammatory disease?", Eur. Cytokine Netw., vol. 20, No. 3, pp. 108-111, Accepted for publication: Sep. 8, 2009.
Mazodier, Karin et al., "Severe imbalance of IL-18/IL-18BP in patients with secondary hemophagocytic syndrome", BLOOD, vol. 106, No. 10, pp. 3483-3489, Nov. 15, 2005.

International Search Report and Written Opinion issued by the European Patent Office for PCT/EP2016/054524 dated Mar. 8, 2016.
Office Action issued by the Republic of Columbia Superintendence of Industry and Trade for corresponding CO Patent Application No. NC2017/0008940 dated Mar. 19, 2019.
Office Action issued by the Japanese Patent Office (JPO) for corresponding JP Patent Application No. 2016-539564 dated Jul. 25, 2019.
Office Action issued by the Federal Service for Intellectual Property (ROSPATENT), Ministry of Economic Development of the Russian Federation for corresponding RU Patent Application No. 2016112596 dated Jul. 2, 2019.
Mariuzza, et al., "The Structural Basis of Antigen-Antibody Recognition", Ann. Rev. Biophys. Biophys. Chem., vol. 16, pp. 139-159, 1987.
Novick, et al., "Interleukin-18 Binding Protein isoform a precursor [*Homo sapiens*]", NCBI Reference Sequence: NP_766630.2, Jun. 24, 2013.
Novick, et al., "Interleukin-18 Binding Protein: A Novel Modulator of the TH1 Cytokine Response", Immunity, vol. 10, pp. 127-138, Jan. 1999.
Esteban, et al., "Identification of residues in an orthopoxvirus interleukin-18 binding protein involved in ligand binding and species specificity", Virology, vol. 323, pp. 197-207, Received: Nov. 3, 2003.
Kim, et al., "Structural requirements of six naturally occurring isoforms of the IL-18 binding protein to inhibit IL-18", PNAS, vol. 97, No. 3, pp. 1190-1195, Feb. 1, 2000.
Krumm, et al., "Structural basis for antagonism of human interleukin 18 by poxvirus interleukin 18-binding protein", PNAS, vol. 105, No. 52, pp. 20711-20715, Dec. 30, 2008.
Krumm, et al., "A Unique Bivalent Binding and Inhibition Mechanism by the Yatapoxvirus Interleukin 18 Binding Protein" PLOS Pathogens, vol. 8, Issue 8, e1002876, pp. 1-15, Aug. 2012.
Xiang, et al., "Determination of the Functional Epitopes of Human Interleukin-18-binding Protein by Site-directed Mutagenesis*", Journal of Biological Chemistry, vol. 276, No. 20, pp. 17380-17386, Issue of May 18, 2001.
"Office Action issued by the Japanese Patent Office", for corresponding JP Patent Application No. 2017-546603 dated Dec. 25, 2019.
"Communication pursuant to Article 94(3) EPC", issued by the European Patent Office dated May 25, 2020 for counterpart application No. 16707773.4, pp. 1-6.
"Examination Report", issued by the Intellectual Property Office of India dated Feb. 12, 2019 for counterpart application No. 201647012010, pp. 1-7.
Hornbeck, et al., "Enzyme-Linked Immunosorbent Assays (ELISA)", Current Protocols in Immunology, Supplement 15, XP055034483, May 1, 2001, pp. 11.2.1-11.2.22.

\* cited by examiner

107C6

*VH DNA Sequence:*

ATGGGTTGGGTGTGGACCTTGCCATTCCTGATGGCAGCTGCCCAAAGTATCCA
AGCACAGATCCAGTTGGTGCAGTCTGGTCCTGAACTGAAGAAGCCTGGAGAGA
CAGTCAAGCTCTCCTGCAGGGCTTCTGGATATACATTCACAAACTATGGAATGA
ACTGGGTGAAGCAGGCTCCAGGAAAGGGTTTAAAGTGGATGGGCTGGATAAA
CACCTACTCTGGAGTGCCAACATATGCTGATGACTTCAAGGGACAGTTTGCCTT
CTCTTTGGAAACCTCTGCCGCCACTGCCTTTTTGCAGATCAACAACCTCAAAGA
TGAGGACACGGCTACATATTTTTGTGCAAGAGAGGGATATAGTACTACCAGGT
CTATGGACTACTGGGGTCAAGGAACCTCAGTCACCGTCTCCTCAGCCAAAACG
ACACCCCCATCTGTCTATCCACTGGCC     (SEQ ID NO: 81)

*VH Amino Acid Sequence:*

MGWVWTLPFLMAAAQSIQAQIQLVQSGPELKKPGETVKLSCRASGYTFTNYGMN
WVKQAPGKGLKWMGWINTYSGVPTYADDFKGQFAFSLETSAATAFLQINNLKD
EDTATYFCAREGYSTTRSMDYWGQGTSVTVSSAKTTPPSVYPLA (SEQ ID NO: 82; SEQ ID NO: 9 (bold sequence); (SEQ ID NO: 27-29 (underlined sequences))

*VK DNA Sequence:*

ATGGAGTCACAGTCTCAGGTTCTTATATTGCTGCTGCTATGGGTATCTGGTACC
TGTGGGGACATTGTGATGTCACAGTCTCCATCCTCCCTGGCTGTGTCAGCAGG
AGAGAAGGTCACTATGAGCTGCAAATCCAGTCAGAGTCTGCTCGACAGTAGAA
CCCGAAAGAACTACTTGGTTTGGTACCAGCAGAAACCAGGGCAGTCTCCTAAA
CTGCTGATCTACTGGGCATCCACTAGGGGATCTGGGGTCCCTGATCGCTTCAC
AGGCAGTGGATCTGGGACAGATTTCACTCTCACCATCAGCAGTGTGCAGGCTG
AAGACCTGGCAGTTTATTACTGCAAACAATCTTATAATCTTCGGACGTTCGGTG
GAGGCACCAAGCTGGAAATCAAACGGGCTGATGCTGCACCAACTGTATCCATC
TTCCCACCATCCAGTGAGCAGTTAACATCTGGAGGTGCCTCAGTCGTGTGCTT
CTTGAACAACTTCTACCCCAAA     (SEQ ID NO: 83)

*VK Amino Acid Sequence:*

MESQSQVLILLLLWVSGTCGDIVMSQSPSSLAVSAGEKVTMSCKSSQSLLDSRTR
KNYLVWYQQKPGQSPKLLIYWASTRGSGVPDRFTGSGSGTDFTLTISSVQAEDL
AVYYCKQSYNLRTFGGGTKLEIKRADAAPTVSIFPPSSEQLTSGGASVVCFLNNFY
PK     (SEQ ID NO: 84; SEQ ID NO: 10 (bold sequence); (SEQ ID NO: 30-32 (underlined sequences))

*VH DNA Sequence:*

ATGGGTTGGGTGTGGACCTTGCTATTCCTGATGGCAGCTGCCCAAAGTATCCA
ATCACAGATCCAGTTGGTGCAGTCTGGTCCTGATTCGAAGAAGCCTGGAGAGA
CAGTCAAGCTCTCCTGCAGGGCTTCTGGATATACATTCACAAACTATGGAATGA
ACTGGGTGAAGCAGGCTCCAGGAAAGGGTTTAAAGTGGATGGGCTGGATAAA
CACCTACTCTGGAGTGCCAACATATGCTGATGACTTCAAGGGACAGTTTGCCTT
CTCTTTGGAAACCTCTGCCGCCACTGCCTTTTTGCAGATCAACAACCTCAAAGA
TGAGGACACGGCTACATATTTTTGTGCAAGAGAGGGATATAGTACTACCAGGT
CTATGGACTACTGGGGTCAAGGAACCTCAGTCACCGTCTCCTCAGCCAAAACG
ACACCCCCATCTGTCTTCCCCCTGGCACCT    (SEQ ID NO: 85)

*VH Amino Acid Sequence:*

MGWVWTLLFLMAAAQSIQSQIQLVQSGPDSKKPGETVKLSCRASGYTFTNYGMN
WVKQAPGKGLKWMGWINTYSGVPTYADDFKGQFAFSLETSAATAFLQINNLKD
EDTATYFCAREGYSTTRSMDYWGQGTSVTVSSAKTTPPSVFPLAP

(SEQ ID NO: 86; SEQ ID NO: 11 (bold sequence); (SEQ ID NO: 33-35 (underlined sequences))

*VK DNA Sequence:*

ATGGGCTTCAAGATGAAGTCAGTCGACCTGGTTCTTATATTGCTGCTGCTATGG
GTATCTGGTACCTGTGGGGACATTGTGATGTCACAGTCTCCATCCTCCCTGGC
TGTGTCAGCAGGAGAGAAGGTCACTATGAGCTGCAAATCCAGTCAGAGTCTGC
TCGACAGTAGAACCCGAAAGAACTACTTGGTTTGGTACCAGCAGAAACCAGGG
CAGTCTCCTAAACTGCTGATCTACTGGGCATCCACTAGGGGATCTGGGGTCCC
TGATCGCTTCACAGGCAGTGGATCTGGGACAGATTTCACTCTCACCATCAGCA
GTGTGCAGGCTGAAGACCTGGCAGTTTATTACTGCAAACAATCTTATAATCTTC
GGACGTTCGGTGGAGGCACCAAGCTGGAAATCAAACGGGCTGATGCTGCACC
AACTGTATCCATCTTCCCACCATCCAGTGAGC-
AGTTAACATCTGGAGGTGCCTCAGTCGTGTGCTTCTTGAACAACTTCTACCCC (SEQ ID NO: 87)

*VK Amino Acid Sequence:*

MGFKMKSVDLVLILLLLWVSGTCGDIVMSQSPSSLAVSAGEKVTMSCKSSQSLLD
SRTRKNYLVWYQQKPGQSPKLLIYWASTRGSGVPDRFTGSGSGTDFTLTISSVQ
AEDLAVYYCKQSYNLRTFGGGTKLEIKRADAAPTVSIFPPSSEQLTSGGASVVCFL
NNFYP    (SEQ ID NO: 88; SEQ ID NO: 12 (bold sequence); (SEQ ID NO: 36-38 (underlined sequences))

*VH DNA Sequence:*

ATGAAATGCAGCTGGATTATGTTCTTCCTGATGGCAGTGGTTACAGGGGTCAAT
TCAGAGGTTCAGCTGCAGCAGTCTGGGGCAGAACTTGTGAAGCCAGGGGCCT
CAGTCAAGTTGTCCTGCACAGCTTCTGGCTTCAAAATTAAAGACACCTATATAC
ACTGGGTGATCCAGAGGCCTGCACAGGGCCTGGAATGGATTGGAAGGATTGA
TCCTGCGAATGGTAATACTATTTATGGCTCAAAGTTCCAGGGCAAGGCCACTCT
AACAGCGGACACATCATCCAACACAGCCTACATTCACCTCAGCAGCCTGACAT
CTGGGGACTCTGCCGTCTATTACTGTGCGGGCTACGTTTGGTTTGCTTACTGG
GGCCAAGGGACTCTGGTCACTGTCTCTGCAGCTACAACAACAGCCCCATCCGT
CTTCCCCCTGGCACCA (SEQ ID NO: 89)

*VH Amino Acid Sequence:*

MKCSWIMFFLMAVVTGVNSEVQLQQSGAELVKPGASVKLSCTAS<u>GFKIKDTYIH</u>
WVIQRPAQGLEWIG<u>RIDPANGNTIYGSKFQGKATL</u>TADTSSNTAYIHLSSLTSGDS
AVYYC<u>AGYVWFAY</u>WGQGTLVTVSAATTTAPSVFPLAP (SEQ ID NO: 90)

(SEQ ID NO: 90; SEQ ID NO: 13 (bold sequence); (SEQ ID NO: 39-41 (underlined sequences))

*VK DNA Sequence:*

ATGAAGTTGCCTGTTAGGCTGTTGGTGCTGATGTTCTGGATTCCTGCCTCCAG
CAGTGATGTTGTGATGACCCAAGTTCCACTCTCCCTGCCTGTCAGTCTTGGAG
ATCAAGCCTCCATCTCTTGCAGATCTAGTCAGAGACTTGTGCACAGTAATGGAA
ACACCTATTTACATTGGTTCTTACAGAAGCCAGGCCAGTCTCCAAAGCTCCTGA
TCTACACAGTTTCCAACCGATTTTCTGGGGTCCCAGACAGGTTCAGTGGCAGT
GGATCAGGGACAGATTTCACACTCAAGATCAGCAGAGTGGAGGCTGAGGATCT
GGGAGTTTATTTCTGCTCTCAAAGTACACTTGTTCCGTGGACGTTCGGTGGAG
GCACCAAGCTGGAAATCAAACGGGCTGATGCTGCACCAACTGTATCCATCTTC
CCACCATCCAGTGAGCAGTTAACATCTGGAGGTGCCTCAGTCGTGTGCTTCTT
GAACAACTTCTACCCAAAG (SEQ ID NO: 91)

*VK Amino Acid Sequence:*

MKLPVRLLVLMFWIPASSSDVVMTQVPLSLPVSLGDQASISCRSS<u>QRLVHSNGNT</u>
<u>YLH</u>WFLQKPGQSPKLLIY<u>TVS</u>NRFSGVPDRFSGSGSGTDFTLKISRVEAEDLGVY
FC<u>SQSTLVPWT</u>FGGGTKLEIKRADAAPTVSIFPPSSEQLTSGGASVVCFLNNFYPK (SEQ ID NO: 92; SEQ ID NO: 14 (bold sequence); (SEQ ID NO: 42-44 (underlined sequences))

*VH DNA Sequence:*

ATGAAATGCAGCTGGGTTATGTTCTTCCTGATGGCAGTGGTTACAGGGGTCAA
TTCAGAGGTTCAGCTGCAGCAGTCTGGGGCAGAACTTGTGAAGCCAGGGGCC
TCAGTCAAGTTGTCCTGCACAGCTTCTGGCTTCAAAATTAAAGACACCTATATA
CACTGGGTGATCCAGAGGCCTGCACAGGGCCTGGAATGGATTGGAAGGATTG
ATCCTGCGAATGGTAATACTATTTATGGCTCAAAGTTCCAGGGCAAGGCCACTC
TAACAGCGGACACATCATCCAACACAGCCTACATTCACCTCAGCAGCCTGACA
TCTGGGGACTCTGCCGTCTATTACTGTGCGGGCTACGTTTGGTTTGCTTACTG
GGGCCAAGGGACTCTGGTCACTGTCTCTGCAGCTACAACAACAGCCCCATCC
GTCTTCCCCCTGGCACCA     (SEQ ID NO: 93)

*VH Amino Acid Sequence:*

MKCSWVMFFLMAVVTGVNSEVQLQQSGAELVKPGASVKLSCTAS<u>GFKIKDTYIH</u>
**WVIQRPAQGLEWIGR<u>IDPANGNTI</u>YGSKFQGKATLTADTSSNTAYIHLSSLTSGDS
AVYYC<u>AGYVWFAY</u>WGQGTLVTVSA**ATTTAPSVFPLAP     (SEQ ID NO: 94;
SEQ ID NO: 15 (bold sequence); (SEQ ID NO: 45-47 (underlined sequences))

*VK DNA sequence1*

ATGGATTTTCAGGTGCAGATTTTCAGCTTCTTGCTAATCAGTGCCTCAGTTGCA
ATGTCCAGAGGAGAAAATGTGCTCACCCAGTCTCCAGCAATCATGTCTGCTTCT
CCAGGGGAGAAGGTCACCATGACCTGCAGGGCCAGGTCAAGTGTAAGTTCCA
GTTACTTGCACTGGTACCAGCAGAAGTCAGGTGCCTCCCCCAAACTCTGGATT
TATAGCACATCCAACTTGGCTTCTGGAGTCCCTACTCGCTTCAGTGGCAGTGG
GTCTGGGACCTCTTACTCTCTCACAATCAGCAGTGTGGAGGCTGAAGATGCTG
CCACTTATTACTGCCAGCAGTACAGTGGTTACCCACTCACGTTCGGTGCTGGG
ACCAAGCTGGAGCTGAAACGGGCTGATGCTGCACCAACTGTATCCATCTTCCC
ACCATCCAGTGAGCAGTTAACATCTGGAGGTGCCTCAGTCGTGTGCTTCTTGA
ACAACTTCTACCCCAAG     (SEQ ID NO: 95)

*VK Amino Acid Sequence:*

MDFQVQIFSFLLISASVAMSRGENVLTQSPAIMSASPGEKVTMTCRAR<u>SSVSSSYL</u>
**HWYQQKSGASPKLWIY<u>STS</u><u>N</u>LASGVPTRFSGSGSGTSYSLTISSVEAEDAATYY
C<u>QQYSGYPLT</u>FGAGTKLELK**RADAAPTVSIFPPSSEQLTSGGASVVCFLNNFYPK
(SEQ ID NO: 96; SEQ ID NO: 16 (bold sequence); (SEQ ID NO: 48-50 (underlined sequences))

*Figure 11-4*

*VK DNA sequence 2*

ATGAAGTTGCCTGTTAGGCTGTTGGTGCTGATGTTCTGGATTCCTGCCTCCAG
CAGTGATGTTGTGATGACCCAAGTTCCACTCTCCCTGCCTGTCAGTCTTGGAG
ATCAAGCCTCCATCTCTTGCAGATCTAGTCAGAGACTTGTGCACAGTAATGGAA
ACACCTATTTACATTGGTTCTTACAGAAGCAGGCCAGTCTCCAAAGCTCCTGA
TCTACACAGTTTCCAACCGATTTTCTGGGGTCCCAGACAGGTTCAGTGGCAGT
GGATCAGGACAGATTTCACACTCAAGATCAGCAGAGTGGAGGCTGAGGATCT
GGGAGTTTATTTCTGCTCTCAAAGTACACTTGTTCCGTGGACGTTCGGTGGAG
GCACCAAGCTGGAAATCAAACGGGCTGATGCTGCACCAACTGTATCCATCTTC
CCACCATCCAGTGAGCAGTTAACATCTGGAGGTGCCTCAGTCGTGTGCTTCTT
GAACAACTTCTACCCCAAAG (SEQ ID NO: 97)

*VK Amino Acid Sequence 2:*

MKLPVRLLVLMFWIPASSSDVVMTQVPLSLPVSLGDQASISCRSSQRLVHSNGNT
YLHWFLQKPGQSPKLLIYTVSNRFSGVPDRFSGSGSGTDFTLKISRVEAEDLGVY
FCSQSTLVPWTFGGGTKLEIKRADAAPTVSIFPPSSEQLTSGGASVVCFLNNFYPK
(SEQ ID NO: 98; SEQ ID NO: 17 (bold sequence); (SEQ ID NO: 51-53 (underlined sequences))

131B4

*VH DNA Sequence:*

ATGAAATGCAGCTGGATTATGTTCTTCCTGATGGCAGTGGTTACAGGGGTCAAT
TCAGAGGTTCAGGTGCAGCAGTCTGGGGCAGAGCTTGTGAAGCCAGGGGCCT
CAGTCAAGTTGTCCTGCACAGCTTCTGGCTTCAAAATTAAGGACACCTATATAC
ACTGGTTAAAACAGAGGCCTGAACAGGGCCTGGAATGGATTGGAAGGATTGAT
CCTGCGAATGGTAATACTATATATGGCTCAAAGTTCCAGGGCAAGGCCACTATA
ACAGCAGACACATCATCCAACACAGCCTACATTCAACTCAGCAGCCTGACATCT
GGGGACACTGCCGTCTATTTTGTGCGGGCTACGTTTGGTTTGCTTACTGGGG
CCAAGGGACTCTGGTCACTGTCTCTGCAGCCAAAACGACACCCCATCCGTCT
TCCCCCTGGCC (SEQ ID NO: 99)

*VH Amino Acid Sequence:*

MKCSWIMFFLMAVVTGVNSEVQVQQSGAELVKPGASVKLSCTASGFKIKDTYIH
WLKQRPEQGLEWIGRIDPANGNTIYGSKFQGKATITADTSSNTAYIQLSSLTSGDT
AVYFCAGYVWFAYWGQGTLVTVSAAKTTPPSVFPLA (SEQ ID NO: 100; SEQ
ID NO: 18 (bold sequence); (SEQ ID NO: 54-56 (underlined sequences))

*Figure 11-5*

*VH DNA Sequence 2:*

ATGGCTGTCTTGGGGCTGCTCTTCTGCCTGGTGACATTCCCAAGCTGTGTCCT
GTCCAGGTGCAGCTGAAGCAGTCAGGACCTAGCCTAGTGCAGCCCTCACAG
AGCCTGTCCATAACCTGCACAGTCTCTGGTTTCTCATTAACTAGCTATGGTGTA
CACTGGGTTCGCCAGTCTCCAGGAAAGGGTCTGGAGTGGCTGGGAGTGATAT
GGAGAGGTGGAAGCACAGACTACAATGCAGCTTTCATGTCCAGACTGAGCATC
ACCAAGGACAACTCCAAGAGCCAAGTTTTCTTTAAAATGAACAGTCTGCAAGCT
GATGACACTGCCATATACTACTGTGCCAAAAATTGGGAGTATGATGGTTACTGG
GGGTTTGCTTACTGGGGCCAAGGGACTCTGGTCACTGTCTCTGCAGAGAGTCA
GTCCTTCCCAAATGTCTTCCCCCTCGAA (SEQ ID NO: 101)

*VH Amino Acid Sequence 2:*

MAVLGLLFCLVTFPSCVLSQVQLKQSGPSLVQPSQSLSITCTVSGFSLTSYGVHW
VRQSPGKGLEWLGVIWRGGSTDYNAAFMSRLSITKDNSKSQVFFKMNSLQADD
TAIYYCAKNWEYDGYWGFAYWGQGTLVTVSAESQSFPNVFPLE (SEQ ID NO: 102; SEQ ID NO: 103 (bold sequence); (SEQ ID NO: 104-106 (underlined sequences))

*VH DNA Sequence 3:*

ATGGCAGTGGTTACAGGGGTCAATTCAGAGGTTCAGCTGCAGCAGTCTGGGG
CTGAGCTTGTGAGGCCAGGGGCCTCAGTCAAGTTGTCCTGCACAGCTTCTGG
CTTTAACATTAAAGACGACTATATGCACTGGGTGAAGCAGAGGCCTGAACAGG
GCCTGGAGTGGATTGGAAGGATTGATCCTGCGAATGGTAATACTAAATATGCC
CCGAAGTTCCAGGACAAGGCCACTATAACTGCAGACACATCCTCCAACACAGC
CTACCTGCAGCTCAGCAGCCTGACATCTGAGGACACTGCCGTCTATTACTGTG
CTAGAAGCTATGATGGTTCTCTGGGGACTACTGGGGCCAAGGCACCACTCTC
ACAGTCTCCTCAGAGAGTCAGTCCTTCCCAAATGTCTTCCCCCTCGAG (SEQ ID NO: 107)

*VH Amino Acid Sequence 3:*

MAVVTGVNSEVQLQQSGAELVRPGASVKLSCTASGFNIKDDYMHWVKQRPEQG
LEWIGRIDPANGNTKYAPKFQDKATITADTSSNTAYLQLSSLTSEDTAVYYCARS
YDGSLGDYWGQGTTLTVSSESQSFPNVFPLE (SEQ ID NO: 108; SEQ ID
NO: 109 (bold sequence); (SEQ ID NO: 110-112 (underlined sequences))

*Figure 11-6*

*VK DNA Sequence:*

ATGAAGTTGCCTGTTAGGCTGTTGGTGCTGATGTTCTGGATTCCTGCTTCCAGC
AGTGATGCTGTGTTGACCCAAACTCCACTCTCCCTGCCTGTCAGTCTTGGAGA
TCAAGCCTCCATCTCTTGCACATCTAGTCAGAGCCTTGTACACAGTAATGGAAA
CACCTATTTACATTGGTACCTGCAGAAGCCAGGCCAGTCTCCAAAGCTCCTGA
TCTACAAAGTTTCCGACCGATTTTCTGGGGTCCCAGACAGGTTCAGTGGCAGT
GGATCAGGAACAGATTTCACACTCATGATCACCAGAGTGGAGGCTGAGGATCT
GGGAGTTTATTTCTGCTCTCAAAGTTCACTTGTTCCGTGGACGTTCGGTGGAG
GCACCAAGCTGGAAGTCAAACGGGCTGATGCTGCACCAACTGTATCCATCTTC
CCACCATCCAGTGAGCAGTTAACATCTGGAGGTGCCTCAGTCGTGTGCTTCTT
GAACAACTTCTACCCCAAA (SEQ ID NO: 113)

*VK Amino Acid Sequence:*

MKLPVRLLVLMFWIPASSSDAVLTQTPLSLPVSLGDQASISCTSSQSLVHSNGNTY
LHWYLQKPGQSPKLLIYKVSDRFSGVPDRFSGSGSGTDFTLMITRVEAEDLGVYF
CSQSSLVPWTFGGGTKLEVKRADAAPTVSIFPPSSEQLTSGGASVVCFLNNFYPK (SEQ ID NO: 114; SEQ ID NO: 19 (bold sequence); (SEQ ID NO: 57-59 (underlined sequences))

131E8

*VH DNA Sequence 1:*

ATGGCTGTTTTGGGGCTGCTCTTCTGCCTGGTGACATTCCCAAGCTGTGTCCT
ATCCCAGGTGCAGCTGAAGCAGTCAAGACCTGGCCCAGTGCAGCCCTCACAG
AGCCTGTCCATCACCTGCACAGTCTCTGGTTTCTCATTACCTAACTATGGTGTA
CACTGGGTTCGCCAGCCTCCAGGAAAGGGTCTGGAGTGGCTGGGAGTGATAT
GGAGTGGTGGAAGCACAGACTATAATGCAGCTTTCAAATCCAGACTGAGCATC
AGCAAGGACAACTCCAAGAGCCAAGTTTTCTTTAAAATGAACAGTCTGCAAGCT
GATGACACAGCCATATACTACTGTGCCAGAAATTTTTATAGTAAGTACGACTAT
GCTATGGACTACTGGGGTCAAGGAACCTCAGTCACCGTCTCCTCAGCCAAAAC
AACACCCCCATCCGTCTTCCCCCTGGC (SEQ ID NO: 115)

*VH Amino Acid Sequence 1:*

MAVLGLLFCLVTFPSCVLSQVQLKQSRPGPVQPSQSLSITCTVSGFSLPNYGVHW
VRQPPGKGLEWLGVIWSGGSTDYNAAFKSRLSISKDNSKSQVFFKMNSLQADDT
AIYYCARNFYSKYDYAMDYWGQGTSVTVSSAKTTPPSVFPL (SEQ ID NO: 116;
SEQ ID NO: 20 (bold sequence); (SEQ ID NO: 60-62 (underlined sequences))

*VH DNA Sequence 2:*

ATGTTCTTCTTGGTAGCAACAGCTACAGGTGTCCACTCCCAGGTCCAACTGCA
GCAGCCTGGGTCTGTGCTGGTGAGGCCTGGAGCTTCAGTGAAGCTGTCCTGC
AAGGCTTCTGGCTACACATTCACCAGCTACTGGATGCACTGGGTGAAGCAGAG
GCCGGGACAAGGCCTTGAGTGGATTGGAAATATTAATCCTAATAGTGGTAGTA
CTAACTACAATGAGAAGTTCAAGGGCAAGGCCACACTGACTGTAGACACATCC
TCCAGCACAGCCTACATGGATCTCAGCAGCCTGACATCTGAGGACTCTGCGGT
CTATTACTGTGCAAGACTGGGTGACTACTGGGGCCAAGGCACCACTCTCACAG
TCTCCTCAAAGAGTCAGTCCTCCCCATCCGTCTTCCCCCTG (SEQ ID NO: 117)

*VH Amino Acid Sequence 2:*

MFFLVATATGVHSQVQLQQPGSVLVRPGASVKLSCKASGYTFTSYWMHWVKQR
PGQGLEWIGNINPNSGSTNYNEKFKGKATLTVDTSSSTAYMDLSSLTSEDSAVYY
CARLGDYWGQGTTLTVSSKSQSSPSVFPL (SEQ ID NO: 118; SEQ ID NO: 21
(bold sequence); (SEQ ID NO: 63-65 (underlined sequences))

*VH DNA Sequence 3:*

GCTGTCTTGGGGCTGCTCTTCTGCCTGGTTGCATTTCCAAGCTGTGTCCTGTC
CCAGGTGCAGCTGAAGGAGTCAGGACCTGGCCTGGTGGCGCCCTCACAGAGC
CTGTCCATCACTTGCACTGTCTCTGGGTTTTCATTAACCAGCTATGGTGTACAC
TGGGTTCGCCAGCCTCCAGGAAAGGGTCTGGAGTGGCTGGGAGTAATATGGG
CTGGTGGAAGCACAAATTATAATTCGGCTCTCATGTCCAGACTGAGCATCAGC
AAAGACAACTCCAAGAGCCAAGTTTTCTTAAAAATGAACAGTCTGCAAACTGAT
GACACAGCCATGTACTACTGTGCCAGAGATAGTAACTACTTTGACTACTGGGG
CCAAGGCACCACTCTCACAGTCTCCTCAGAGAGTCAGTCCTTCCCAAATGTCTT
CCCCCTCGTA (SEQ ID NO: 119)

*VH Amino Acid Sequence 3:*

AVLGLLFCLVAFPSCVLSQVQLKESGPGLVAPSQSLSITCTVSGFSLTSYGVHWV
RQPPGKGLEWLGVIWAGGSTNYNSALMSRLSISKDNSKSQVFLKMNSLQTDDT
AMYYCARDSNYFDYWGQGTTLTVSSESQSFPNVFPLV (SEQ ID NO: 120; SEQ
ID NO: 121 (bold sequence); (SEQ ID NO: 122-124 (underlined sequences))

*Figure 11-8*

*VK DNA Sequence:*

ATGGATTTTCAGGTGCAGATTTTCAGCTTCCTGCTAATCAGTGCCTCAGTCATA
ATGTCCAGAGGAGAAAATGTTCTCACCCAGTCTCCAGCAATCATGTCTGCATCT
CCAGGGGAAAAGGTCACCATGACCTGCAGTGCCAGCTCAAGTGTAAGTTACAT
GCACTGGTACCAGCAGAAGTCAAGCACCTCCCCCAAACTCTGGATTTATGACA
CATCCAAACTGGCTTCTGGAGTCCCAGGTCGCTTCAGTGGCAGTGGGTCTGGA
AACTCTTACTCTCTCACGATCAGCAGCATGGAGGCTGAAGATGTTGCCACTTAT
TACTGTTTTCAGGGGAGTGGGTACCCACTCACGTTCGGCTCGGGGACAAAGTT
GGAAATAAAACGGGCTGATGCTGCACCAACTGTATCCATCTTCCCACCATCCA
GTGAGCAGTTAACATCTGGAGGTGCCTCAGTCGTGTGCTTCTTGAACAACTTCT
ACCCCAAA         (SEQ ID NO: 125)

*VK Amino Acid Sequence:*

MDFQVQIFSFLLISASVIMSRGENVLTQSPAIMSASPGEKVTMTCSASSSVSYMH
WYQQKSSTSPKLWIYDTSKLASGVPGRFSGSGSGNSYSLTISSMEAEDVATYYC
FQGSGYPLTFGSGTKLEIKRADAAPTVSIFPPSSEQLTSGGASVVCFLNNFYPK (SEQ ID NO: 126; SEQ ID NO: 22 (bold sequence); SEQ ID NO: 66-68 (underlined sequences))

131H1

*VH DNA Sequence:*

ATGGCTGTCTTGGGGCTGCTCTTCTGCCTGGTGACATTCCCAAGCTGTGTCCT
ATCCCAGGTGCAGCTGAAGCAGTCAGGACCTGGCCTAGTGCAGCCCTCACAG
AGCCTGTCCATCACCTGCACAGTCTCTGGTTTCTCATTAACTAGCTATGGTGTA
CACTGGGTTCGCCAGTCTCCAGGAAAGGGTCTGGAGTGGCTGGGAGTGATAT
GGAGTGGTGGAAGCACAGACTATAATGCAGCTTTCATATCCAGACTGAGCATC
AGCAAGGACAATTCCAAGAGCCAAGTTTTCTTTAAAATGAACAGTCTGCAAGCT
GATGACACAGCCATATATTACTGTGCCAGATCTTATGATTACGACGGGAGGGG
TTACTTTGACTACTGGGGCCAAGGCACCACTCTCACAGTCTCCTCAGAGAGTC
AGTCCTTCCCAAATGTCTTCCCCCTCGTA  (SEQ ID NO: 127)

*VH Amino Acid Sequence:*

MAVLGLLFCLVTFPSCVLSQVQLKQSGPGLVQPSQSLSITCTVSGFSLTSYGVHW
VRQSPGKGLEWLGVIWSGGSTDYNAAFISRLSISKDNSKSQVFFKMNSLQADDT
AIYYCARSYDYDGRGYFDYWGQGTTLTVSSESQSFPNVFPLV (SEQ ID NO: 128; SEQ ID NO: 129 (bold sequence); SEQ ID NO: 130-132 (underlined sequences))

*Figure 11-9*

VK DNA Sequence 1:

ATGAGTGTGCTCACTCAGGTCCTGGGGTTGCTGCTGCTGTGGCTTACAGGTGC
CAGATGTGACATCCAGATGACTCAGTCTCCAGCCTCCCTGTCTGCATCTGTGG
GAGAAACTGTCACCATCACATGTCGAGCAAGTGAGAATGTTTACAGATATTTAG
CATGGTATCAGCAGAGACAGGGAAAATCTCCTCAGCTCCTGGTCTATAGTGCA
AAAACCTTAGCAGAAGGTGTGCCATCAAGGTTCAGTGGCAGTGGATCAGGCAC
ACAGTTTTCTCTGAAGATCAACACCCTGCAGCCTGAAGATTTTGGGACTTATTA
CTGTCAACATCATTATAATACTCCTCTCACGTTCGGTGCTGGGACCAAGCTGGA
GCTGAAACGGGCTGATGCTGCACCAACTGTATCCATCTTCCCACCATCCAGTG
AGCAGTTAACATCTGGAGGTGCCTCAGTCGTGTGCTTCTTGAACAACTTCTACC
CCAAA    (SEQ ID NO: 133)

VK Amino Acid Sequence 1:

MSVLTQVLGLLLLWLTGARCDIQMTQSPASLSASVGETVTITCRASENVYRYLAW
YQQRQGKSPQLLVYSAKTLAEGVPSRFSGSGSGTQFSLKINTLQPEDFGTYYCQ
HHYNTPLTFGAGTKLELKRADAAPTVSIFPPSSEQLTSGGASVVCFLNNFYPK ((SEQ ID NO: 134; SEQ ID NO: 135 (bold sequence); SEQ ID NO: 136-138 (underlined sequences))

VK DNA Sequence 2:

ATGGTTCTTATATGGCTCCTGCTATGGGTATCTGGTACCTGTGGGGACATTGTG
ATGTCACAGTCTCCATCCTCCCTGGCTGTGTCAGCAGGAGAGAAGGTCACTAT
GAGCTGCAAATCCAGTCAGAGTCTGTTCAACAGTAAAACCCGAAAGAACTACTT
GGCTTGGTTTCAGCAAAAACCAGGGCAGTCTCCTGAACTGCTGATCTACTGGG
CATCCACTAGGAAATCTGGGGTCCCTGATCGCTTCACAGGCAGTGGATCTGGG
ACAGATTTCACTCTCACCATCAGCAGTGTGCAGGCTGAAGACCTGGCAGTTTA
TTACTGCAAGCAATCTTATAATCTGTGGACGTTCGGCGGAGGCACCAAGCTGG
AAATCAAACGGGCTGATGCTGCACCAACTGTATCCATCTTCCCACCATCCAGT
GAGCAGTTAACATCTGGAGGTGCCTCAGTCGTGTGCTTCTTGAACAACTTCTAC
CCCAAA    (SEQ ID NO: 139)

VK Amino Acid Sequence 2:

MVLIWLLLWVSGTCGDIVMSQSPSSLAVSAGEKVTMSCKSSQSLFNSKTRKNYL
AWFQQKPGQSPELLIYWASTRKSGVPDRFTGSGSGTDFTLTISSVQAEDLAVYY
CKQSYNLWTFGGGTKLEIKRADAAPTVSIFPPSSEQLTSGGASVVCFLNNFYPK ((SEQ ID NO: 140; SEQ ID NO: 141 (bold sequence); SEQ ID NO: 142-144 (underlined sequences))

*VH DNA Sequence:*

TGAGCTGGGTTTTCCTTGTCCTTATTTTAAAAGGTGTCCAGTGTGAAGTGAAGC
TGGTGGAGTCTGGGGGAGGCTTAGTGAAGCCTGGAGGGTCCCTGAAACTCTC
CTGTGCAGCCTCTGGATTCACTTTCAGTAACTATGCCATGTCTTGGGTTCGCCA
GAATCCGGCGAAGAGGCTGGAGTGGGTCGCAACCATTAGTAGTGGTGGTGCT
AATATTTACTATCCAGACAGTGTGAAGGGCCGATTCATCATCTCCAGAGACAAT
GCCAGGAACACCCTGTACCTGCAAATGAGCAGTCTGAGGTCTGAGGACACGG
CCATGTATTACTGTGCAAGAGGCGACTATTTTAACCACTTCTGGTTTGCTTACT
GGGGCCAAGGGACTCTTGTCACTGTCTCTGCAGCCAAAACAACAGCCCCATCG
GTCTTCCCCCTGGCA (SEQ ID NO: 145)

*VH Amino Acid Sequence:*

SWVFLVLILKGVQCEVKLVESGGGLVKPGGSLKLSCAASGFTFSNYAMSWVRQN
PAKRLEWVATISSGGANIYYPDSVKGRFIISRDNARNTLYLQMSSLRSEDTAMYY
CARGDYFNHFWFAYWGQGTLVTVSAAKTTAPSVFPLA (SEQ ID NO: 146; SEQ ID NO: 23 (bold sequence); (SEQ ID NO: 69-71 (underlined sequences))

(missing A at the start of the sequence, should be MSWVF)

*Figure 11-11*

*VK DNA Sequence:*

ATGAAGTTGCCTGTTAGGCTGTTGGTGCTGATGTTCTGGATTCCTGCTTCCAGC
AGTGATGTTTTGATGACCCAAACTCCACTCTCCCTGCCTGTCAGTCTTGGAGAT
CAAGCCTCCATCTCTTGTAGATCGAGTCAGAGCATTGTACATAGTAATGGAAAC
ACCTATTTAGAATGGTACCTGCAGAAACCAGGCCAGTCTCCAAAGTTCCTGATC
TACAAAGTTTCCAACCGATTTTCAGGGGTCCCAGACAGGTTCAGTGGCAGTGG
ATCAGGGACAGATTTCACACTCAAGATCAACAGAGTGGAGGCTGAGGATCTGG
GAATTTATTACTGCTTTCAGGGTTCACATGTTCCGTGGACGTTCGGTGGAGGC
ACCAAGCTGGAAATCAAACGGGCTGATGCTGCACCAACTGTATCCATCTTCCC
ACCATCCAGTGAGCAGTTAACATCTGGAGGTGCCTCAGTCGTGTGCTTCTTGA (SEQ ID NO: 147)

*VK Amino Acid Sequence:*

MKLPVRLLVLMFWIPASSSDVLMTQTPLSLPVSLGDQASISCRSSQSIVHSNGNTY
LEWYLQKPGQSPKFLIYKVSNRFSGVPDRFSGSGSGTDFTLKINRVEAEDLGIYY
CFQGSHVPWTFGGGTKLEIKRADAAPTVSIFPPSSEQLTSGGASVVCFL (SEQ ID NO: 148; SEQ ID NO: 24 (bold sequence); (SEQ ID NO: 72-74 (underlined sequences))

_____(missing last 6 amino acids usually NNFYPK or NNFYPR)

133A6

*VH DNA Sequence:*

ATGAACTTTGGGTTGAGATTGGTTTTCCTTGTCCTTGTTTTAAAAGGTGTCCAGT
GTGAGGTGAAGCTAGTGGAGTCTGGAGGAGGCTTAGTGAAGCCTGGAGGGTC
CCTGAAACTCTCCTGTGCAGCCTCTGGATTCACTTTCAGTAACTATGCCATGTC
TTGGGTTCGCCAGACTCCGGCGAAGAGGCTGGAGTGGGTCACAACCATTAGT
AGTGGTGGTGGTAACATCTACTATACAGACAGTGTGAAGGGCCGATTCACCGT
CTCCAGAGACAATGCCAGGAACACCCTGTACCTGCAAATGAGCAGTCTGAGGT
CTGAGGACACGGCCATGTATTACTGTGCAAGAGGCGACTATAGTAACTACTTC
TGGTTTGCTTACTGGGGCCAAGGGACTCTGGTCTCTGTCTCTGAAGCCAAAAC
AACAGCCCCATCGGTCTTCCCCCTGGCACCT    (SEQ ID NO: 149)

*VH Amino Acid Sequence:*

MNFGLRLVFLVLVLKGVQCEVKLVESGGGLVKPGGSLKLSCAASGFTFSNYAMS
WVRQTPAKRLEWVTTISSGGGNIYYTDSVKGRFTVSRDNARNTLYLQMSSLRSE
DTAMYYCARGDYSNYFWFAYWGQGTLVSVSEAKTTAPSVFPLAP (SEQ ID NO: 150; SEQ ID NO: 25 (bold sequence); (SEQ ID NO: 75-77 (underlined sequences))

*Figure 11-12*

*VK DNA Sequence:*

ATGAAGTTGCCTGTTAGGCTGTTGGTGCTGATGTTCTGGATTCCTGCTTCCAGC
AGTGATGTTTTGATGACCCAAACTCCACTCTCCCTGCCTGTCAGTCTTGGAGAT
CAAGCCTCCATCTCTTGCAGATCTAGTCAGAGCATTGTACATAGTAATGGAAAC
ACCTATTTAGAATGGTACCTGCAGAAACCAGGCCAGTCTCCAAAGCTCCTGAT
CTACAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCTG
GGAGTTTATTACTGCTTTCAAGGTTCACATGTTCCGTGGACGTTCGGTGGAGG
CACCAAGCTGGAAATCAAACGGGCTGATGCTGCACCAACTGTATCCATCTTCC
CACCATCCAGGGAGCAGTTAACATCTGGAGGTGCCTCAGTCGTGTGCTTCTTG
AACAACTTCTACCCAAAA (SEQ ID NO: 151)

*VK Amino Acid Sequence:*

MKLPVRLLVLMFWIPASSSDVLMTQTPLSLPVSLGDQASISCRSSQSIVHSNGNTY
LEWYLQKPGQSPKLLIYKVSNRFSGVPDRFSGSGSGTDFTLKISRVEAEDLGVYY
CFQGSHVPWTFGGGTKLEIKRADAAPTVSIFPPSREQLTSGGASVVCFLNNFYPK (SEQ ID NO: 152; SEQ ID NO: 26 (bold sequence); (SEQ ID NO: 78-80 (underlined sequences))

*Figure 11-13*

IL-18 BINDING PROTEIN (IL-18BP) IN INFLAMMATORY DISEASES

CROSS REFERENCE TO RELATED APPLICATIONS

This application is a 35 U.S.C. § 371 national stage application of International Application No. PCT/EP2014/069013 filed on Sep. 5, 2014, published in English under PCT Article 21(2), which claims the benefit of priority to European Patent Application No. 13183193.5 filed on Sep. 5, 2013, the disclosures of which are hereby incorporated by reference.

TECHNICAL FIELD

The present invention provides means and methods for treating Interleukin 18 (IL-18)-associated diseases and disorders. In particular, the present invention discloses antibodies specific for free IL-18 and IL-18 Binding Protein (IL-18BP) for use in such treatments and for the diagnosis of the indications.

BACKGROUND ART

Interleukin-18 (IL-18), also known as interferon-gamma inducing factor is a cytokine, which is produced by activated macrophages, Kupffer cells and other cells. IL-18 binds to the IL-18 receptor and induces cell-mediated immunity. Defects (e.g. knock-out) of the IL-18 cytokine receptor or IL-18 cytokine lead to impaired natural killer (NK) cells activity and TH1 responses. Apart from its physiological role, IL-18 may also induce severe inflammatory disorders. For the purpose of early diagnosis of such disorders it therefore would be necessary to quantify the levels of free IL-18 in body fluids of a subject, expected to have such a disorder.

However, at present, the quantification of IL-18 levels in body fluids is usually performed by using ELISA assays, which comprise antibodies that are unspecific for the detection of free IL-18. The result achieved by ELISA assays is limited by the specificity of the used primary antibody, which binds the target antigen. Up to date it is merely possible to detect total IL-18 levels by using the commercially available antibodies, but no antibodies to free IL-18 are known so far. The detection of total IL-18 is inadequate for the assessment of free IL-18 levels, since IL-18 bound in a complex, e.g. bound to its natural antagonist IL-18 binding protein (IL-18BP) has a reduced affinity to IL-18 receptor. Further, it is known, that increased IL-18 levels often are associated with elevated IL-18BP levels.

In virtue of the reasons described above, the determination of total IL-18 it is insufficient to make an adequate diagnosis of IL-18 associated diseases. That means, in order to being able to assess the levels of free IL-18 in body fluids of a subject and to make an adequate diagnosis of IL-18 associated disease, a detection means would be required which specifically bind to free IL-18, but not to IL-18 bound in a complex. Accordingly, there exists at present no effective treatment for IL-18 associated diseases or disorders.

The present invention now provides such detection means in form of an IL-18 binding molecule, particularly an IL-18 binding protein (IL-18BP) or an antibody, which specifically binds to free IL-18, but not to IL-18 bound in a complex. Therefore, the present invention satisfies the need for an adequate means for the detection of free IL-18 and for diagnosis of diseases or disorders, which are associated with free IL-18 in the body fluids.

This opens the door for an efficient personalized medicine approach. In particular, it is now for the first time possible to identify the population of patients that are suffering from diseases or disorders, which are associated with free IL-18 in the body tissues, but particularly in the body fluids and to effectively treat said patients by administration of binding molecules which specifically bind free-IL18.

The present invention thus further provides effective therapeutic means for the treatment and prevention of IL-18 associated diseases or disorders in the population of patients that are suffering from diseases or disorders, which are associated with free IL-18 in the body tissues, but particularly in the body fluids. The present invention also satisfies the need for an effective treatment of diseases or disorders, which are associated with free IL-18 in the body tissues, particularly in the body fluids by providing IL-18 binding molecules, particularly (1) IL-18BP, and/or (2) antibodies, which are specific for free IL-18 and do not cross-react with IL-18 bound in a complex.

The IL-18 binding molecules, but particularly the IL-18BP and the IL-18 specific antibodies according to the present invention are able to reduce and/or abrogate the binding of free IL-18 to its receptor and to provide therapeutic benefits to patient suffering from an IL-18 associated disease or disorder.

Recent non-clinical and clinical investigations have defined a prominent role of the pro-inflammatory cytokine Interleukin 18 (IL-18) in the pathogenesis of Chronic Obstructive Pulmonary Disease, and suggest that IL-18 acts as the master regulator of destructive and remodeling processes.

Chronic obstructive pulmonary disease (COPD), also known as chronic obstructive lung disease (COLD), chronic obstructive airway disease (COAD), chronic airflow limitation (CAL) and chronic obstructive respiratory disease (CORD), is the occurrence of chronic bronchitis or emphysema, a pair of commonly co-existing diseases of the lungs in which the airways narrow over time. This leads to a limited airflow to and from the lung, which is considered as not fully reversible, but becomes rather becomes progressively worse over time. Smoking is responsible for 90% of COPD in the Europe and in the United States. Although not all tobacco smokers will develop COPD, it is estimated that 20% will. Smokers with COPD have higher death rates than nonsmokers with COPD. They also have more frequent respiratory symptoms (coughing, shortness of breath, etc.) and more deterioration in lung function than non-smokers. Other risk factors are, for instance, genetic susceptibility (e.g. α1-anti-trypsin deficiency as well as regions on chromosome 4 near HHIP and in FAM13A and on chromosome 15 in CHRNA and IREB2), previous tuberculosis, air pollution, occupational exposure to dusts and fumes (airborne particles), exposure to second-hand smoke, and biomass smoke inhalation. COPD is comprised primarily of two related diseases: chronic bronchitis and emphysema. Chronic bronchitis is the inflammation and eventual scarring of the lining of the bronchial tubes. When the bronchi are inflamed and/or infected, less air is able to flow to and from the lungs and a heavy mucus or phlegm is coughed up. Emphysema begins with the destruction of alveoli (air sacs in the lungs where oxygen from the air is exchanged for carbon dioxide in the blood) due in part, by an abnormal inflammatory response of the lung to noxious particles or gases, chiefly tobacco smoke. The walls of the air sacs are thin and fragile. Damage to the air sacs is irreversible and results in permanent "holes" in the tissues of the lower lungs. As air sacs are destroyed, the lungs are able to transfer less and less oxygen to the bloodstream, causing shortness of breath. The lungs also lose their elasticity, which is important to keep airways open. As a result, the patient experiences great difficulty exhaling. In both chronic bronchitis and emphysema the obstruction and tissue destruction is generally permanent and progressive. COPD patients often experience exacerbations. The term "exacerbation" refers to the aggravation of the symptoms or an increase in the severity of the disease. The duration of an exacerbation can vary greatly—from hours to several days. Exacerbations may cause symptoms specific to the respiratory process to increase. The patient may experience increased dyspnea, a productive cough with an altered sputum, and fever. The sputum may increase or be more purulent and change color. The patient may also experience nonspecific symptoms such as malaise, fatigue, insomnia, sleepiness, or depression. Exacerbations of COPD are usually caused by an infection of the lower respiratory tract. The most common causes of infection are: aerobic Gram-positive and Gram-negative bacteria, atypical bacteria, respiratory virus, rhinovirus, influenza virus, RSV, or a combination of pathogens. Viral exacerbations are more severe, last longer, and are associated with greater levels of inflammation and loss of lung function than exacerbations due to other causes (Wedzicha, 2004, PATS; Seemungel et al., 2001, AM. J. RCCM; Tan et al., 2003, Am. J. Med. Donaldson et al., 2000, Thorax). Each COPD patient is likely to experience 1 to 4 exacerbations a year. While many patients experience these exacerbations, it is estimated that they only report about 50% of all episodes to physicians. Frequent exacerbations have been associated with a poor quality of life and a high economic burden.

Studies in COPD disease models have addressed IL-18-induced pulmonary inflammation in cigarette smoke (CS)-induced and in second hand smoke-induced pulmonary emphysema and inflammation and its association with COPD in smokers, demonstrating that IL-18 and IL-18 signaling pathways via IL-18R are significantly activated by cigarette smoke exposure in animal models and in human lung inflammation and airspace enlargement in cigarette smoke-induced pulmonary emphysema. The results corroborate the important role of alveolar macrophages as the main cellular source of IL-18 release IL-18 was shown to induce airway and vascular remodeling in lung-specific, inducible IL-18-transgenic mice as well as tissue inflammation, emphysema, mucus metaplasia, and cardiac right ventricle hypertrophy.

IL-18 was further shown to induce emphysema and the cytotoxic response via an IFN-γ-dependent mechanism, fibrotic airway remodeling, mucus metaplasia, and vascular remodeling via an IL-17A- and IL-13-dependent pathway. There are important interactions between these pathways with IL-18-inducing IL-13 via an IL-17A-dependent mechanism and the IFN-γ and the IL-17A/IL-13 responses counter-regulating one another. Consequently, IL-18 is central to the modulation of multiple inflammatory cascades Systemic IL-18 levels in patients with COPD suggest alveolar macrophages as the source of circulating IL-18 in COPD and have shown that IL-18 is elevated in circulation and in induced sputum of COPD patients.

Elevated serum IL-18 levels in comorbidities to COPD are suggested to be associated with systemic inflammation.

Further, a strong correlation was found between serum IL-18 levels and lung function.

Overall, the non-clinical and clinical results clearly advocate for inhibiting/neutralizing IL-18 as a potential upstream target, thereby preventing or limiting both the destructive and remodeling processes typically leading to COPD disease manifestation and progression.

It can be concluded from the results of recent clinical investigations on IL-18 levels in circulation and in sputum of COPD patients, that IL-18 lung levels are significantly elevated in COPD patients in association with disease severity.

Data on IL-18 in sputum from patients with COPD suggests that alveolar macrophages are the predominant source of IL-18 in COPD and that IL-18 is significantly overexpressed in the lungs of COPD patients vs. controls.

Recent studies on the role of the NLRP3 inflammasome in stimulating caspase-1 activation followed by the release of the mature form of the pro-inflammatory cytokines IL-1b and IL-18 have contributed to further elucidate the effects of tobacco smoke in airway inflammation (Rastrick et al., 2013).

In mice exposed to cigarette smoke twice daily, the caspase-1 activation and IL-18 release was examined (Eltom et al., 2011).

The smoke-induced up-regulation of IL-18 via caspase-1 activation is demonstrated by comparing the effects of tobacco smoke and the exposure to normal air.

Altogether, IL-18 presents as the favorite upstream target for future COPD therapeutics capable to interfere with the destructive and remodeling processes in COPD lungs, thereby being a promising candidate for a disease-modifying treatment modality in COPD.

It was therefore suggested in WO2008/150431 A1 to treat COPD and associated comorbidities resulting from elevation of IL-18, IFN-γ, or PKR in subjects suffering from COPD and associated comorbidities by administering to said subjects an IL-18 Inhibitor, an IL-18Rα Inhibitor, and IFN-γ Inhibitor, a PKR Inhibitor, and any combination thereof.

Inhibition of IL-18 by, for example, monoclonal antibodies, which target IL-18 signaling by receptor blockade leads to a long duration of action due the prolonged half-life of these agents, thereby acting not only on the deleterious IL-18 activities but also interfere with the beneficial effects for host defense thus leading to undesired side effects in terms of the response driven to pathogens (viruses, bacteria, fungi and other parasites) by IFN-gamma suppression and lymphocyte T helper type 1.

It was now surprisingly found within the context of the present invention that these undesired side effects can be avoided by taking an alternative approach, i.e., administration of the naturally occurring IL-18 Binding Protein (IL-18BP), which has a high binding affinity to Interleukin 18 (IL-18) and a fundamentally different mode of action of targeting IL-18 as compared, for example, to the art-known monoclonal antibodies.

In a specific embodiment of the invention, the IL-18 Binding Protein (IL-18BP) has a binding affinity of between 20 pM and 30 pM, when determined in a BIAcore setup as shown in Example 4.4.2.

The present invention thus relates in one embodiment to an IL-18 binding molecule, which specifically binds to free IL-18 without cross-reacting with IL-18 bound in a complex (referred to in the following as "free IL-18 specific binding molecule"), particularly a free IL-18 specific binding molecule which is an IL-18 inhibitor, which reduces and/or abrogates the binding of free IL-18 to its receptor (referred to in the following as "IL-18 inhibitor"), particularly an IL-18BP, for use in the treatment of an IL-18 associated disease or disorder in a subject diagnosed of having abnormal levels of free IL-18 and/or an abnormal ratio of free IL-18/IL-18BP in the body fluids compared to the levels in body fluids of a healthy control subject.

In particular, said abnormal level of free IL-18 in the body fluids exceeds the level in body fluids of a healthy control subject by 5%, 10%, 20%, 30%, 40%, 50%, 60%, 70%, 80%, 90%, 100%, or more than 100%.

In another embodiment the present invention provides the free IL-18 specific binding molecule, particularly the IL-18 inhibitor, particularly the IL-18BP, for use according to the present invention and as disclosed herein, wherein said abnormal levels of free IL-18 in the body samples, particularly in body fluids, have been determined by use of an IL-18 binding molecule, particularly an IL-18 binding protein (IL-18BP) or an antibody, which specifically binds to free IL-18, but not to IL-18 bound in a complex according to the invention and as disclosed herein in certain embodiments.

Further, in one embodiment, the present invention provides the free IL-18 specific binding molecule, particularly the IL-18 inhibitor, particularly the IL-18BP, for use as disclosed in any one of the preceding embodiments, wherein the subject to be treated belongs to a group of subjects which have been determined to have elevated levels of free IL-18 and/or an abnormal ratio of free IL-18/IL-18BP in body samples, particularly in a sample selected from the group consisting of broncho-alveolar lavage fluid (BALF) circulation fluids, secretion fluids, biopsy and homogenized tissue, particularly serum, urine, tear, saliva, bile, sweat, exhalation, expiration, sputum, bronchoalveolar fluid, sebum, cellular, gland, mucosa, and tissue secretion compared to the levels in samples taken from healthy subjects.

Said elevated levels of free IL-18 in a sample form a diseased patient or subject are ≥5 pg/mL and up to 10000 pg/mL or higher. In particular, said elevated levels of free IL-18 in a sample form a diseased patient or subject are in the range of ≥5 pg/mL to 10000 pg/mL, particularly in the range of 100 pg/mL to 10000 pg/mL, particularly in the range of 200 pg/mL to 10000 pg/mL, particularly in the range of 300 pg/mL to 10000 pg/mL, particularly in the range of 400 pg/mL to 10000 pg/mL, particularly in the range of 500 pg/mL to 10000 pg/mL, particularly in the range of 600 pg/mL to 10000 pg/mL, particularly in the range of 700 pg/mL to 10000 pg/mL, particularly in the range of 800 pg/mL to 10000 pg/mL, particularly in the range of 900 pg/mL to 10000 pg/mL, particularly in the range of 1000 to 10000 pg/mL, particularly in the range of 1500 pg/mL to 10000 pg/mL, particularly in the range of 2000 pg/mL to 10000 pg/mL, particularly in the range of 3000 pg/mL to 10000 pg/mL, particularly in the range of 4000 pg/mL to 10000 pg/mL, particularly in the range of 5000 pg/mL to 10000 pg/mL. The amount of free IL-18 in serum of healthy subject, particularly a healthy human is ≤5 pg/mL, particularly ≤4 pg/mL, particularly ≤1 pg/mL, particularly ≤0.5 pg/m, particularly below detection level.

Yet another object of the present invention is to provide the free IL-18 specific binding molecule, particularly the IL-18 inhibitor, particularly the IL-18BP, for use as disclosed in any one of the preceding embodiments, wherein said IL-18 associated disease or disorder is one selected from the group consisting of Adult Still's disease, juvenile Still's disease, chronic obstructive pulmonary disease (COPD), transfusion-related lung injury, bronchopulmonary dysplasia (BPD), adult respiratory distress syndrome (ARDS), interstitial lung disease (ILD), idiopathic pulmonary fibrosis, cystic fibrosis, pulmonary arterial hypertension, asthma, bronchiectasis, heart failure, amyotrophic lateral sclerosis (ALS), dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behçet's disease, conjunctivitis, allergic conjunctivitis, dermatitis of eyelid, diabetes type 2, non-alcoholic fatty liver disease (NAFLD), steato hepatitis, solid organ and hematologic transplantation, ischemia reperfusion injury, familial Mediterranean fever, tumor necrosis factor receptor 1-associated periodic syndromes, cryopyrin-associated periodic fever syndromes, hyper-IgD syndromes, gout, Schnitzler syndrome, Wegener's granulomatosis also called granulomatosis with polyangitis (GPA), Hashimoto's thyroiditis, Crohn's disease, ulcerative colitis, immunoglobulin-4 (IgG4)-related diseases and stem cell therapies.

In a particular embodiment, the present invention provides the free IL-18 specific binding molecule, particularly the IL-18 inhibitor, particularly the IL-18BP, for use as disclosed in any one of the preceding embodiments, wherein said IL-18 associated disease or disorder is induced by smoking or second-hand smoke exposure, in particular tobacco smoke exposure.

In another particular embodiment, the present invention provides the free IL-18 specific binding molecule, particularly the IL-18 inhibitor, particularly the IL-18BP, for use as disclosed in any one of the preceding embodiments, wherein said IL-18 associated disease or disorder is induced by viral infection.

Yet another object of the present invention is to provide the free IL-18 specific binding molecule, particularly the IL-18 inhibitor, particularly the IL-18BP, for use as disclosed in any one of the preceding embodiments, wherein said IL-18 associated disease or disorder is an IL-18 induced systemic manifestation of inflammation and associated comorbidities selected from the group consisting of emphysema, tissue inflammation, tissue destruction, lung resection, disappearance of the vasculature, apoptosis of endothelial cells, mucos metaplasia, cardiac hypertrophy, decrease of VEGF in the lung tissue, pulmonary vessel loss, vessel muscularization, vascular remodeling, collagen deposition, aberrant elastin layers in the lung, fibrotic airway remodeling, airspace enlargement, chronic remodeling of the airways and pulmonary vessels and decreased pulmonary function.

Another object of the present invention is to provide a free IL-18 specific binding molecule, particularly an IL-18 inhibitor for use as disclosed in any one of the preceding embodiments, which is an antibody, particularly an antibody specific for free IL-18, particularly an antagonistic antibody, which prevents binding of free IL-18 to IL-18 receptor, especially free IL-18 binding to IL-18Rα.

The IL-18 specific antibody according to the present invention including any functionally equivalent antibody or parts thereof, binds to IL-18 at the binding site of IL-18BP or in the vicinity of the binding site of IL-18BP, or is a conformational antibody, which binds to at least two epitopes on the IL-18 molecule, which are comprised of discontinuous amino acids that come together in three-dimensional conformation and interact with the receptor's paratope such that the binding site of IL-18BP on the IL-18 molecule is blocked.

In one embodiment, the IL-18 specific antibody including any functionally equivalent antibody or parts thereof according to the present invention and as disclosed herein in the various embodiments binds free IL-18 protein, but not IL-18/IL-18BP complexes.

In particular, the IL-18 specific antibody including any functionally equivalent antibody or parts thereof according to the present invention shows cross-reactivity with the IL-18/IL-18BP complex of between ≤0.01% and ≤0.05%, particularly of between ≤0.1% and ≤0.2%, particularly between ≤0.2% and ≤0.5%, particularly of between ≤0.5% and ≤1%, particularly of between ≤1% and ≤2% as determined by competitive ELISA.

In a specific embodiment, the IL-18 specific antibody including any functionally equivalent antibody or parts thereof according to the present invention shows cross-reactivity with the IL-18/IL-18BP complex of ≤0.1% as determined by competitive ELISA.

In one embodiment, the IL-18 specific antibody including any functionally equivalent antibody or parts thereof as disclosed in any one of the preceding embodiments sterically hinders the binding of IL-18BP to IL-18.

In still another embodiment, the IL-18 specific antibody including any functionally equivalent antibody or parts thereof as disclosed in any one of the preceding embodiments specifically binds to a single epitope, a combination of two epitopes or a combination of 3 epitopes comprised in a sequence selected from a group of sequences depicted in SEQ ID NO: 1, SEQ ID NO: 2 and SEQ ID NO: 3, respectively.

In a specific embodiment, the antibody of the invention specifically binds to a single epitope, comprised in a sequence selected from a group of sequences depicted in SEQ ID NO: 1, SEQ ID NO: 2 and SEQ ID NO: 3.

In another specific embodiment, the antibody of the invention specifically binds to two epitopes, comprised in a sequence selected from a group of sequences depicted in SEQ ID NO: 1, SEQ ID NO: 2 and SEQ ID NO: 3, respectively.

In particular, the antibody binds to two epitopes comprised in a sequence of (a) SEQ ID NO: 1 and SEQ ID NO: 2, respectively, (b) SEQ ID NO: 1 and SEQ ID NO: 3, respectively, (c) SEQ ID NO: 2 and SEQ ID NO: 3, respectively.

In another specific embodiment, the antibody of the invention specifically binds to three epitopes, comprised in a sequence of SEQ ID NO:1, SEQ ID NO: 2 and SEQ ID NO: 3, respectively.

In one embodiment, the present invention provides the IL-18 specific antibody including any functionally equivalent antibody or parts thereof as disclosed in any one of the preceding embodiments, which antibody specifically binds to a single epitope, a combination of two epitopes or a combination of 3 epitopes selected from the group consisting of SEQ ID NO: 4, SEQ ID NO: 5 and SEQ ID NO: 6.

In particular, the present invention further relates to said IL-18 specific antibody including any functionally equivalent antibody or parts thereof, wherein said epitope has a sequence which has 90%, 91%, 92%, 93%, 94%, 95%, 96%, 97%, 98%, 99% or 100% sequence identity to the sequence depicted in SEQ ID NO: 4, SEQ ID NO:5 or SEQ ID NO: 6.

In a specific embodiment, the antibody of the invention specifically binds to a single epitope, comprised in a sequence selected from a group of sequences depicted in SEQ ID NO: 4, SEQ ID NO: 5 and SEQ ID NO: 6.

In another specific embodiment, the antibody of the invention specifically binds to two epitopes, comprised in a sequence selected from a group of sequences depicted in SEQ ID NO:4, SEQ ID NO: 5 and SEQ ID NO: 6.

In particular, the antibody binds to two epitopes comprised in a sequence of (a) SEQ ID NO: 4 and SEQ ID NO: 5, respectively, (b) SEQ ID NO: 4 and SEQ ID NO: 6, respectively, (c) SEQ ID NO: 5 and SEQ ID NO: 6, respectively.

In another specific embodiment, the antibody of the invention specifically binds to three epitopes, comprised in a sequence of SEQ ID NO: 4, SEQ ID NO: 5 and SEQ ID NO: 6, respectively.

In a specific embodiment, the antibody according to the present invention as disclosed herein in the various embodiments including any functionally equivalent antibody or an antigen-binding portion thereof comprises at least one, at least two or all three complementarity determining regions (CDRs) of the light chain variable region as shown in SEQ ID NOs: 10, 12, 14, 16, 17, 19, 22, 24 and 26, respectively, and/or at least one, at least two or all three complementarity determining regions (CDRs) of the heavy chain variable region as shown in SEQ ID NOs: 9, 11, 13, 15, 18, 20, 21, 23, and 25, respectively, wherein said antibody, equivalent antibody or antigen-binding portion thereof binds free IL-18 protein, particularly at the binding site of IL-18BP or in the vicinity of the binding site of IL-18BP, but does not bind IL-18/IL-18BP complexes.

In particular, the antibody according to the present invention as disclosed herein in the various embodiments including any functionally equivalent antibody or an antigen-binding portion thereof comprises the complementarity determining regions (CDRs) of the light chain variable region as shown in SEQ ID NOs: 10, 12, 14, 16, 17, 19, 22, 24 and 26, respectively, and the complementarity determining regions (CDRs) of the heavy chain variable region as shown in SEQ ID NOs: 9, 11, 13, 15, 18, 20, 21, 23, and 25, respectively, wherein said antibody, equivalent antibody or antigen-binding portion thereof binds free IL-18 protein, particularly at the binding site of IL-18BP or in the vicinity of the binding site of IL-18BP, but does not bind IL-18/IL-18BP complexes to any significant extent.

In a specific embodiment, the antibody according to the present invention as disclosed herein in the various embodiments including any functionally equivalent antibody or an antigen-binding portion thereof comprises at least one, at least two or all three complementarity determining regions (CDRs) of the light chain variable region as shown in FIG. 11, and/or at least one, at least two or all three complementarity determining regions (CDRs) of the heavy chain variable region as shown in FIG. 11, wherein said antibody, equivalent antibody or antigen-binding portion thereof binds free IL-18 protein, particularly at the binding site of IL-18BP or in the vicinity of the binding site of IL-18BP, but does not bind IL-18/IL-18BP complexes.

In particular, the antibody according to the present invention as disclosed herein in the various embodiments including any functionally equivalent antibody or an antigen-binding portion thereof comprises the complementarity determining regions (CDRs) of the light chain variable region as shown in as shown in FIG. 11, and the complementarity determining regions (CDRs) of the heavy chain variable region as shown in as shown in FIG. 11, wherein said antibody, equivalent antibody or antigen-binding portion thereof binds free IL-18 protein, particularly at the binding site of IL-18BP or in the vicinity of the binding site of IL-18BP, but does not bind IL-18/IL-18BP complexes to any significant extent.

In a specific embodiment of the invention, the complementarity determining regions (CDRs) are determined according to the variable domain residue numbering as in Kabat.

In another specific embodiment of the invention, the complementarity determining regions (CDRs) are determined according to the variable domain residue numbering as in Chothia.

In another specific embodiment of the invention, the complementarity determining regions (CDRs) are determined by the IMGT system.

The antibody according to the present invention as disclosed herein in the various embodiments including any functionally equivalent antibody or an antigen-binding portion thereof comprises the complementarity determining regions (CDRs) as follows:

a. CDR1, CDR2, and CDR 3 of the heavy chain variable region having the sequence as shown in SEQ ID NO: 27, SEQ ID NO: 28, and SEQ ID NO: 29, respectively; and CDR1, CDR2, and CDR 3 of the light chain variable region having the sequence as shown in SEQ ID NO: 30, SEQ ID NO: 31, and SEQ ID NO: 32, respectively; or b. CDR1, CDR2, and CDR 3 of the heavy chain variable region having the sequence as shown in SEQ ID NO: 33, SEQ ID NO: 34, and SEQ ID NO: 35, respectively; and CDR1, CDR2, and CDR 3 of the light chain variable region having the sequence as shown in SEQ ID NO: 36, SEQ ID NO: 37, and SEQ ID NO: 38, respectively; or c. CDR1, CDR2, and CDR 3 of the heavy chain variable region having the sequence as shown in SEQ ID NO: 39, SEQ ID NO: 40, and SEQ ID NO: 41, respectively; and CDR1, CDR2, and CDR 3 of the light chain variable region having the sequence as shown in SEQ ID NO: 42, SEQ ID NO: 43, and SEQ ID NO: 44, respectively; or d. CDR1, CDR2, and CDR 3 of the heavy chain variable region having the sequence as shown in SEQ ID NO: 45, SEQ ID NO: 46, and SEQ ID NO: 47, respectively; and CDR1, CDR2, and CDR 3 of the light chain variable region having the sequence as shown in SEQ ID NO: 48, SEQ ID NO: 49, and SEQ ID NO: 50, respectively; or e. CDR1, CDR2, and CDR 3 of the heavy chain variable region having the sequence as shown in SEQ ID NO: 45, SEQ ID NO: 46, and SEQ ID NO: 47, respectively; and CDR1, CDR2, and CDR 3 of the light chain variable region having the sequence as shown in SEQ ID NO: 51, SEQ ID NO: 52, and SEQ ID NO: 53, respectively; or f. CDR1, CDR2, and CDR 3 of the heavy chain variable region having the sequence as shown in SEQ ID NO: 54, SEQ ID NO: 55, and SEQ ID NO: 56, respectively; and CDR1, CDR2, and CDR 3 of the light chain variable region having the sequence as shown in SEQ ID NO: 57, SEQ ID NO: 58, and SEQ ID NO: 59, respectively; or g. CDR1, CDR2, and CDR 3 of the heavy chain variable region having the sequence as shown in SEQ ID NO: 60, SEQ ID NO: 61, and SEQ ID NO: 62, respectively; and CDR1, CDR2, and CDR 3 of the light chain variable region having the sequence as shown in SEQ ID NO: 66, SEQ ID NO: 67, and SEQ ID NO: 68, respectively; or h. CDR1, CDR2, and CDR 3 of the heavy chain variable region having the sequence as shown in SEQ ID NO: 63, SEQ ID NO: 64, and SEQ ID NO: 65, respectively; and CDR1, CDR2, and CDR 3 of the light chain variable region having the sequence as shown in SEQ ID NO: 66, SEQ ID NO: 67, and SEQ ID NO: 68, respectively; or i. CDR1, CDR2, and CDR 3 of the heavy chain variable region having the sequence as shown in SEQ ID NO: 69, SEQ ID NO: 70, and SEQ ID NO: 71, respectively; and CDR1, CDR2, and CDR 3 of the light chain variable region having the sequence as shown in SEQ ID NO: 72, SEQ ID NO: 73, and SEQ ID NO: 74, respectively; or j. CDR1, CDR2, and CDR 3 of the heavy chain variable region having the sequence as shown in SEQ ID NO: 75, SEQ ID NO: 78, and SEQ ID NO: 77, respectively; and CDR1, CDR2, and CDR 3 of the light chain variable region having the sequence as shown in SEQ ID NO: 78, SEQ ID NO: 79, and SEQ ID NO: 80, respectively.

k. CDR1, CDR2, and CDR 3 of the heavy chain variable region having the sequence as shown in FIG. 11; and CDR1, CDR2, and CDR 3 of the light chain variable region having the sequence as shown in FIG. 11.

In one embodiment of the invention, the antibody shows variation in one or more of the CDR sequences to an extent that the antibody incorporating said variant CDRs still has the specific binding activity of an antibody according to the present invention comprising binding of free IL-18 protein, particularly at the binding site of IL-18BP or in the vicinity of the binding site of IL-18BP, without binding IL-18/IL-18BP complexes.

In another specific embodiment of the invention, said antibody is a human or humanized antibody, in particular a human or humanized antibody, wherein the CDRs have been inserted into a human antibody "scaffold" being derived from one (or more) human immunoglobulin(s).

In still another specific embodiment, the invention provides an antibody including any functionally equivalent antibody or an antigen-binding portion thereof comprising at least a light chain variable region having 75%, 80%, 82%, 83%, 84%, 85%, 86%, 87%, 88%, 89%, 90%, 91%, 92%, 93%, 94%, 95%, 96%, 97%, 98%, 99%, 100% sequence identity to the sequence shown in SEQ ID NOs: 10, 12, 14, 16, 17, 19, 22, 24, 26, and FIG. 11, respectively and/or at least a heavy chain variable region having 75%, 80%, 82%, 83%, 84%, 85%, 86%, 87%, 88%, 89%, 90%, 91%, 92%, 93%, 94%, 95%, 96%, 97%, 98%, 99%, 100% sequence identity to the sequence shown in SEQ ID NOs: 9, 11, 13, 15, 18, 20, 21, 23, 25 and FIG. 11, respectively, wherein said antibody, equivalent antibody or antigen-binding portion thereof binds free IL-18 protein, particularly at the binding site of IL-18BP or in the vicinity of the binding site of IL-18BP, but does not bind IL-18/IL-18BP complexes.

In still another specific embodiment, the invention provides an antibody including any functionally equivalent antibody or an antigen-binding portion thereof comprising at least a light chain variable region having 75%, 80%, 82%, 83%, 84%, 85%, 86%, 87%, 88%, 89%, 90%, 91%, 92%, 93%, 94%, 95%, 96%, 97%, 98%, 99%, 100% sequence identity to the sequence shown in SEQ ID NOs: 10, 12, 14, 16, 17, 19, 22, 24, 26, and FIG. 11, respectively, and/or at least a heavy chain variable region having 75%, 80%, 82%, 83%, 84%, 85%, 86%, 87%, 88%, 89%, 90%, 91%, 92%, 93%, 94%, 95%, 96%, 97%, 98%, 99%, 100% sequence identity to the sequence shown in SEQ ID NOs: 9, 11, 13, 15, 18, 20, 21, 23, 25 and FIG. 11, respectively, with the proviso that the sequences of the CDRs of the light chain variable region and/or of the heavy chain variable region remain unchanged and wherein said antibody, equivalent antibody or antigen-binding portion thereof binds free IL-18 protein, particularly at the binding site of IL-18BP or in the vicinity of the binding site of IL-18BP, but does not bind IL-18/IL-18BP complexes.

In one embodiment, the present invention provides the IL-18 specific antibody including any functionally equivalent antibody or parts thereof for use as disclosed in any one of the preceding embodiments, wherein said antibody or part thereof is a monoclonal antibody or a polyclonal antibody.

In a particular embodiment, the present invention provides the IL-18 specific antibody including any functionally equivalent antibody or parts thereof for use as disclosed in any one of the preceding embodiments, wherein said antibody or part thereof is a chimeric, single chain, bispecific, simianized, human and humanized antibody.

In particular, said antibody is a humanized antibody, particularly a humanized antibody, wherein certain amino acids in the framework and constant domains of the heavy and light chain variable regions and/or the heavy and light chain constant regions have been mutated so as to avoid or abrogate an immune response in humans.

In particular, the IL-18 specific antibody including any functionally equivalent antibody or antigen-binding portion thereof according to the present invention shows cross-reactivity with the IL-18/IL-18BP complex of between ≤0.01% and ≤0.05%, particularly of between ≤0.1% and ≤0.2%, particularly between ≤0.2% and ≤0.5%, particularly of between ≤0.5% and ≤1%, particularly of between ≤1% and ≤2% as determined by competitive ELISA.

In a specific embodiment, the IL-18 specific antibody including any functionally equivalent antibody or antigen-binding portion thereof according to the present invention shows cross-reactivity with the IL-18/IL-18BP complex of ≤0.1% as determined by competitive ELISA.

In another particular embodiment the present invention provides the IL-18 specific antibody including any functionally equivalent antibody or parts thereof as disclosed in any one of the preceding embodiments, wherein said antibody or part thereof binds to human IL-18.

Yet another object of the present invention is to provide the IL-18 specific antibody including any functionally equivalent antibody or parts thereof as disclosed in any one of the preceding embodiments, wherein binding of IL-18 to IL-18 receptor subunit alpha (IL-18Rα) and beta (IL-18Rβ), particularly binding to IL-18Rα is reduced by at least 5%, particularly by at least 10%, particularly by at least 15%, particularly by at least 20%, particularly by at least 25%, particularly by at least 30%, particularly by at least 40%, particularly by at least 45%, particularly by at least 50%, particularly by at least 55%, particularly by at least 60%, particularly by at least 65%, particularly by at least 70, particularly by at least 75, particularly by at least 80, particularly by at least 85%, particularly by at least 90%, particularly by at least 95%, particularly by 96%, particularly by 97%, particularly by 98%, particularly by 99%, particularly by 100%.

A further object of the present invention is to provide the free IL-18 specific binding molecule, particularly the IL-18 inhibitor, particularly the IL-18BP, particularly the IL-18 specific antibody including any functionally equivalent antibody or parts thereof as disclosed in any one of the preceding embodiments for use in the treatment of an IL-18 associated disease or disorder in a population of subjects diagnosed of having abnormal levels of free IL-18 and/or an abnormal ratio of free IL-18/IL-18BP in body samples, particularly in body fluids, compared to the levels in body fluids of a healthy control subject, wherein said free IL-18 specific binding molecule, inhibitor, IL-18BP or IL-18 specific antibody or part thereof neutralizes the effect of free IL-18 by restricting or preventing IL-18 binding to IL-18 receptor (IL-18R), especially free IL-18 binding to IL-18Rα.

In one embodiment, the present invention provides the IL-18 specific antibody including any functionally equivalent antibody or parts thereof as disclosed in any one of the preceding embodiments, wherein said antibody or parts thereof
a) specifically binds to a single epitope, a combination of two epitopes or a combination of 3 epitopes comprised in a sequence selected from a group of sequences depicted in SEQ ID NO: 1, SEQ ID NO: 2 and SEQ ID NO: 3; and/or
b) specifically binds to an epitope, which has a sequence identity of 90%, 91%, 92%, 93%, 94%, 95%, 96%, 97%, 98%, 99% or 100% to the sequence depicted in SEQ ID NO: 4, SEQ ID NO:5 or SEQ ID NO: 6; and
c) specifically binds to IL-18 at the binding site of IL-18BP or in the vicinity of the binding site of IL-18BP; and
d) specifically binds to free IL-18 protein, but not IL-18/IL-18BP complexes; and e) sterically hinders the binding of IL-18BP to IL-18; and
f) reduces binding of IL-18 to IL-18 receptor, particularly binding to IL-18Rα by at least 5%, particularly by at least 10%, particularly by at least 15%, particularly by at least 20%, particularly by at least 25%, particularly by at least 30%, particularly by at least 40%, particularly by at least 45%, particularly by at least 50%, particularly by at least 55%, particularly by at least 60%, particularly by at least 65%, particularly by at least 70, particularly by at least 75, particularly by at least 80, particularly by at least 85%, particularly by at least 90%, particularly by at least 95%, particularly by 100%.

In particular, the above specifically defined antibody shows a cross-reactivity with IL-18/IL-18BP complex of between 0.01% and ≤0.05%, particularly of between ≤0.1% and ≤0.2%, particularly between ≤0.2% and ≤0.5%, particularly of between ≤0.5% and ≤1%, particularly of between ≤1% and ≤2% as determined by competitive ELISA.

In certain embodiments of the invention, the IL-18BP and/or the free IL-18 specific antibody as disclosed in any one of the various embodiments can be used as an IL-18 inhibitor.

In certain other embodiment of the invention, the IL-18BP and/or the free IL-18 specific antibody as disclosed in any one of the various embodiments can be used as a capturing molecule, in an assay for detecting free IL-18 in a body sample, particularly in a sample selected from the group consisting of broncho-alveolar lavage fluid (BALF) circulation fluids, secretion fluids, biopsy and homogenized tissue, particularly serum, urine, tear, saliva, bile, sweat, exhalation, expiration, sputum, bronchoalveolar fluid, sebum, cellular, gland, mucosa, and tissue secretion.

In one embodiment, the invention relates to a polynucleotide encoding an antibody according to the invention as disclosed herein in the various embodiments.

In one embodiment, the polynucleotide encodes the variable heavy chain shown in SEQ ID NOs: 9, 11, 13, 15, 18, 20, 21, 23, 25 and FIG. 11.

In one embodiment, the polynucleotide encodes the variable light chain shown in SEQ ID NOs: 10, 12, 14, 16, 17, 19, 22, 24, 26, and FIG. 11.

In one embodiment, the polynucleotide encodes the CDR regions as shown in SEQ ID NOs: 27-80.

In particular, the invention relates to a polynucleotide encoding the heavy chain and/or the light chain variable region of the antibody according to the invention having a sequence that has 75%, 80%, 82%, 83%, 84%, 85%, 86%, 87%, 88%, 89%, 90%, 91%, 92%, 93%, 94%, 95%, 96%, 97%, 98%, 99%, 100% sequence identity to the sequence shown in FIG. 11.

Moreover, the present invention also provides the IL-18 inhibitor according to the present invention for use as disclosed in any one of the preceding embodiments, wherein the inhibitor is IL-18 Binding Protein (IL-18BP), particularly human IL-18BP (hIL-18 BP), particularly IL-18BP including any functionally equivalent or parts thereof, particularly an IL-18BP as shown in SEQ ID NO: 7.

Also included are transcript variants encoding the IL-18BP.

In one embodiment, the present invention provides the IL-18 inhibitor for use as disclosed in any one of the preceding embodiments, wherein the inhibitor is an IL-18 Binding Protein (IL-18BP) which has a sequence identity of 80%, 85%, 90%, 91%, 92%, 93%, 94%, 95%, 96%, 97%, 98%, 99% or 100% to the sequence depicted in SEQ ID NO: 7.

Yet another object of the present invention is to provide the IL-18 inhibitor for use as disclosed in any one of the preceding embodiments, wherein treatment comprises prevention, halting, alleviation or reversion of symptoms associated with said disease or disorder.

In a further embodiment, the present invention provides the IL-18 inhibitor for use as disclosed in any one of the preceding embodiments, wherein IL-18 binding is restricted or inhibited, particularly binding of free IL-18 to IL-18R, but especially binding of free IL-18 to IL-18Rα.

In another embodiment, the present invention provides the IL-18 inhibitor for use as disclosed in any one of the preceding embodiments, wherein IL-18-dependent downstream signaling pathways are modified, particularly inhibited.

In still another embodiment, the present invention provides the IL-18 inhibitor for use as disclosed in any one of the preceding embodiments, wherein increased expression of IFN-γ, IL-13 or IL-17A is modified, particularly inhibited, compared to untreated subjects suffering from said disease or disorder.

It is still another object of the present invention to provide the IL-18 inhibitor for use as disclosed in any one of the preceding embodiments, wherein the IL-18 inhibitor compensates the IL-18/IL-18BP imbalance by trapping the excess of free IL-18 in tissue and circulation.

In one embodiment, the present invention provides the IL-18 inhibitor for use as disclosed in any one of the preceding embodiments, wherein the IL-18 inhibitor inhibits infiltration of neutrophils into the lung, particularly through mitigation of G-CSF release in the lung airways.

Yet another embodiment of the present invention is to provide the IL-18 inhibitor for use as disclosed in any one of the preceding embodiments, which is a full-length protein or a mutein, functional derivative, functional fragment, biologically active peptide, fraction, circularly permuted derivative, fused protein, isoform or a salt thereof.

The present invention also provides the IL-18 inhibitor, particularly the IL-18BP, particularly the antagonistic antibody, as disclosed in any one of the preceding embodiments, for use in the treatment of chronic obstructive pulmonary disease (COPD), heart disease, dry eye disease and/or diabetes type II.

The present invention also provides the IL-18 inhibitor, particularly the IL-18BP, particularly the antagonistic antibody, as disclosed in any one of the preceding embodiments, for use in the treatment of chronic obstructive pulmonary disease (COPD).

The present invention also provides the IL-18 inhibitor, particularly the IL-18BP, particularly the antagonistic antibody, as disclosed in any one of the preceding embodiments, for use in the treatment of heart disease.

The present invention also provides the IL-18 inhibitor, particularly the IL-18BP, particularly the antagonistic antibody, as disclosed in any one of the preceding embodiments, for use in the treatment of dry eye disease.

The present invention also provides the IL-18 inhibitor, particularly the IL-18BP, particularly the antagonistic antibody, as disclosed in any one of the preceding embodiments, for use in the treatment of amyotrophic lateral sclerosis (ALS), The present invention also provides the IL-18 inhibitor, particularly the antagonistic antibody, particularly the IL-18BP, as disclosed in any one of the preceding embodiments, for use in the treatment of diabetes type II.

The present invention also provides the IL-18 inhibitor, particularly the IL-18BP, particularly the antagonistic antibody, as disclosed in any one of the preceding embodiments, for use in the treatment of Adult Still's disease The present invention also provides the IL-18 inhibitor, particularly the IL-18BP, particularly the antagonistic antibody, as disclosed in any one of the preceding embodiments, for use in the treatment of transfusion-related lung injury.

The present invention also provides the IL-18 inhibitor, particularly the IL-18BP, particularly the antagonistic antibody, as disclosed in any one of the preceding embodiments, for use in the treatment of juvenile Still's disease.

The present invention also provides the IL-18 inhibitor, particularly the IL-18BP, particularly the antagonistic antibody, as disclosed in any one of the preceding embodiments, for use in the treatment of bronchopulmonary dysplasia (BPD).

The present invention also provides the IL-18 inhibitor, particularly the IL-18BP, particularly the antagonistic antibody, as disclosed in any one of the preceding embodiments, for use in the treatment of acute respiratory distress syndrome (ARDS).

The present invention also provides the IL-18 inhibitor, particularly the IL-18BP, particularly the antagonistic antibody, as disclosed in any one of the preceding embodiments, for use in the treatment of interstitial lung disease (ILD).

The present invention also provides the IL-18 inhibitor, particularly the IL-18BP, particularly the antagonistic antibody, as disclosed in any one of the preceding embodiments, for use in the treatment of idiopathic pulmonary fibrosis.

The present invention also provides the IL-18 inhibitor, particularly the IL-18BP, particularly the antagonistic antibody, as disclosed in any one of the preceding embodiments, for use in the treatment of cystic fibrosis.

The present invention also provides the IL-18 inhibitor, particularly the antagonistic antibody, particularly the IL-18BP, as disclosed in any one of the preceding embodiments, for use in the treatment of pulmonary arterial hypertension The present invention also provides the IL-18 inhibitor, particularly the IL-18BP, the antagonistic antibody, as disclosed in any one of the preceding embodiments, for use in the treatment of asthma.

The present invention also provides the IL-18 inhibitor, particularly the IL-18BP, particularly the antagonistic antibody, as disclosed in any one of the preceding embodiments, for use in the treatment of bronchiectasis.

The present invention also provides the IL-18 inhibitor, particularly the IL-18BP, particularly the antagonistic antibody, as disclosed in any one of the preceding embodiments, for use in the treatment of heart failure.

The present invention also provides the IL-18 inhibitor, particularly the IL-18BP, particularly the antagonistic antibody, as disclosed in any one of the preceding embodiments, for use in the treatment of keratitis.

The present invention also provides the IL-18 inhibitor, particularly the IL-18BP, the antagonistic antibody, as disclosed in any one of the preceding embodiments, for use in the treatment of corneal ulcer.

The present invention also provides the IL-18 inhibitor, particularly the IL-18BP, particularly the antagonistic antibody, as disclosed in any one of the preceding embodiments, for use in the treatment of corneal neovascularization.

The present invention also provides the IL-18 inhibitor, particularly the IL-18BP, particularly the antagonistic antibody, as disclosed in any one of the preceding embodiments, for use in the treatment of pathological intraocular neovascularization.

The present invention also provides the IL-18 inhibitor, particularly the IL-18BP, particularly the antagonistic antibody, as disclosed in any one of the preceding embodiments, for use in the treatment of iritis.

The present invention also provides the IL-18 inhibitor, particularly the antagonistic antibody, particularly the IL-18BP, as disclosed in any one of the preceding embodiments, for use in the treatment of glaucoma.

The present invention also provides the IL-18 inhibitor, particularly the IL-18BP, particularly the antagonistic antibody, as disclosed in any one of the preceding embodiments, for use in the treatment of macular degeneration.

The present invention also provides the IL-18 inhibitor, particularly the IL-18BP, particularly the antagonistic antibody, as disclosed in any one of the preceding embodiments, for use in the treatment of Sjögren's syndrome.

The present invention also provides the IL-18 inhibitor, particularly the antagonistic antibody, particularly the IL-18BP, as disclosed in any one of the preceding embodiments, for use in the treatment of autoimmune uveitis.

The present invention also provides the IL-18 inhibitor, particularly the IL-18BP, particularly the antagonistic antibody, as disclosed in any one of the preceding embodiments, for use in the treatment of Behçet's disease.

The present invention also provides the IL-18 inhibitor, particularly the IL-18BP, particularly the antagonistic antibody, as disclosed in any one of the preceding embodiments, for use in the treatment of conjunctivitis.

The present invention also provides the IL-18 inhibitor, particularly the IL-18BP, particularly the antagonistic antibody, as disclosed in any one of the preceding embodiments, for use in the treatment of dermatitis of eyelid.

The present invention also provides the IL-18 inhibitor, particularly the IL-18BP, particularly the antagonistic antibody, as disclosed in any one of the preceding embodiments, for use in the treatment of non-alcoholic fatty liver disease (NAFLD).

The present invention also provides the IL-18 inhibitor, particularly the IL-18BP, particularly the antagonistic antibody, as disclosed in any one of the preceding embodiments, for use in the treatment of steato hepatitis.

The present invention also provides the IL-18 inhibitor, particularly the IL-18BP, particularly the antagonistic antibody, as disclosed in any one of the preceding embodiments, for use in the treatment of solid organ and hematologic transplantation.

The present invention also provides the IL-18 inhibitor, particularly the IL-18BP, particularly the antagonistic antibody, as disclosed in any one of the preceding embodiments, for use in the treatment of ischemia reperfusion injury.

The present invention also provides the IL-18 inhibitor, particularly the IL-18BP, particularly the antagonistic antibody, as disclosed in any one of the preceding embodiments, for use in the treatment of familial Mediterranean fever.

The present invention also provides the IL-18 inhibitor, particularly the IL-18BP, particularly the antagonistic antibody, as disclosed in any one of the preceding embodiments, for use in the treatment of tumor necrosis factor receptor 1-associated periodic syndromes.

The present invention also provides the IL-18 inhibitor, particularly the IL-18BP, particularly the antagonistic antibody, as disclosed in any one of the preceding embodiments, for use in the treatment of cryopyrin-associated periodic fever syndromes.

The present invention also provides the IL-18 inhibitor, particularly the IL-18BP, particularly the antagonistic antibody, as disclosed in any one of the preceding embodiments, for use in the treatment of hyper-IgD syndromes.

The present invention also provides the IL-18 inhibitor, particularly the IL-18BP, particularly the antagonistic antibody, as disclosed in any one of the preceding embodiments, for use in the treatment of gout.

The present invention also provides the IL-18 inhibitor, particularly the IL-18BP, particularly the antagonistic antibody, as disclosed in any one of the preceding embodiments, for use in the treatment of Schnitzler syndrome.

The present invention also provides the IL-18 inhibitor, particularly the IL-18BP, particularly the antagonistic antibody, as disclosed in any one of the preceding embodiments, for use in the treatment of Wegener's granulomatosis.

The present invention also provides the IL-18 inhibitor, particularly the IL-18BP, particularly the antagonistic antibody, as disclosed in any one of the preceding embodiments, for use in the treatment of Hashimoto's thyroiditis.

The present invention also provides the IL-18 inhibitor, particularly the IL-18BP, particularly the antagonistic antibody, as disclosed in any one of the preceding embodiments, for use in the treatment of Crohn's disease.

The present invention also provides the IL-18 inhibitor, particularly the IL-18BP, particularly the antagonistic antibody, as disclosed in any one of the preceding embodiments, for use in the treatment of ulcerative colitis.

The present invention also provides the IL-18 inhibitor, particularly the IL-18BP, particularly the antagonistic antibody, as disclosed in any one of the preceding embodiments, for use in the treatment of immunoglobulin-4 (IgG4)-related diseases.

The present invention also provides the IL-18 inhibitor, particularly the IL-18BP, particularly the antagonistic antibody, as disclosed in any one of the preceding embodiments, for use in the treatment of stem cell therapies.

In another embodiment, the present invention provides the IL-18 inhibitor, particularly the IL-18BP, particularly the antagonistic antibody, as disclosed in any one of the preceding embodiments, for use as disclosed in any one of the preceding embodiments, wherein said disease or disorder is induced by smoking or second-hand smoke exposure, in particular tobacco smoke exposure.

In another embodiment, the present invention provides the IL-18 inhibitor, particularly the IL-18BP, particularly the antagonistic antibody, as disclosed in any one of the preceding embodiments, for use as disclosed in any one of the preceding embodiments, wherein said disease or disorder is induced by viral infection.

Further, the present invention also provides the IL-18 inhibitor, particularly the IL-18BP, particularly the antagonistic antibody, as disclosed in any one of the preceding embodiments, for use as disclosed in any one of the preceding embodiments, wherein said disease or disorder is an IL-18 induced systemic manifestation of inflammation and associated comorbidities selected from the group consisting of emphysema, tissue inflammation, tissue destruction, lung resection, disappearance of the vasculature, mucos metaplasia, cardiac hypertrophy, decrease of VEGF in the lung tissue, pulmonary vessel loss, vessel muscularization, collagen deposition, aberrant elastin layers in the lung, fibrotic airway remodeling, airspace enlargement, chronic remodeling of the airways and pulmonary vessels and decreased pulmonary function.

Yet another object of the present invention is to provide the IL-18 inhibitor, particularly the IL-18BP, particularly the antagonistic antibody, as disclosed in any one of the preceding embodiments, for use as disclosed in any one of the preceding embodiments, wherein IL-18 binding is restricted or inhibited, particularly binding of free IL-18 to IL-18R, but especially free IL-18 binding to IL-18Rα.

It is yet another object of the present invention to provide the IL-18 inhibitor, particularly the IL-18BP, particularly the antagonistic antibody, as disclosed in any one of the preceding embodiments, for use as disclosed in any one of the preceding embodiments, wherein IL-18-dependent downstream signaling pathways are modified, particularly inhibited.

It is yet another object of the present invention to provide the IL-18 inhibitor, particularly the IL-18BP, particularly the antagonistic antibody, as disclosed in any one of the preceding embodiments, for use as disclosed in any one of the preceding embodiments, wherein increased expression of IFN-γ, IL-13 or IL-17A is modified, particularly inhibited, compared to untreated subjects suffering from said disease or disorder.

In one embodiment, the present invention provides the IL-18 inhibitor, particularly the IL-18BP, particularly the antagonistic antibody, as disclosed in any one of the preceding embodiments, for use as disclosed in any one of the preceding embodiments, wherein the IL-18 inhibitor compensates the IL-18/IL-18BP imbalance by trapping the excess of free IL-18 in tissue and circulation.

In another embodiment, the present invention provides the IL-18 inhibitor, particularly the IL-18BP, particularly the antagonistic antibody, as disclosed in any one of the preceding embodiments, for use as disclosed in any one of the preceding embodiments, wherein treatment comprises prevention, halting, alleviation or reversion of symptoms associated with said disease or disorder.

Further, the present invention also provides a pharmaceutical composition for use in the treatment of the disease or disorder as defined in any one of the preceding embodiments in a subject suffering from such a disease or disorder or having a predisposition to develop such a disease or disorder as defined in any one of the preceding embodiments, wherein said composition comprises the IL-18 inhibitor, particularly the IL-18BP, particularly the antagonistic antibody, as disclosed in any one of the preceding embodiments, particularly together with a pharmaceutically acceptable carrier and/or excipient, particularly in a prophylactically and/or therapeutically effective amount.

In particular, the present invention provides the pharmaceutical composition of the preceding embodiment, wherein said pharmaceutical composition optionally further provides another inhibitor of a pro-inflammatory cytokine or functional fragment thereof, or a regulatory factor, which induces in-situ expression of said inhibitor of pro-inflammatory cytokine or functional fragment thereof, co-therapeutic agents such as anti-inflammatory, bronchodilatory, antihistamine, decongestant or anti-tussive drug substances.

In one embodiment, the present invention provides the pharmaceutical composition as disclosed in any one of the preceding embodiments, comprising a pharmaceutically acceptable carrier and/or excipient.

In a specific embodiment, the present invention provides a pharmaceutical composition for use in the treatment of the disease or disorder as defined in any one of the preceding embodiments in a subject suffering from such a disease or disorder or having a predisposition to develop such a disease or disorder as defined in any one of the preceding embodiments, wherein said composition comprises the Interleukin-18 Binding Protein (IL-18BP) as disclosed in one or more of the preceding embodiments, particularly together with a pharmaceutically acceptable carrier and/or excipient, particularly in a prophylactically and/or therapeutically effective amount.

In another specific embodiment, the present invention provides a pharmaceutical composition for use in the treatment of the disease or disorder as defined in any one of the preceding embodiments in a subject suffering from such a disease or disorder or having a predisposition to develop such a disease or disorder as defined in any one of the preceding embodiments, wherein said composition comprises the antagonistic free IL-18 specific antibody as disclosed in any one of the preceding embodiments, particularly the antagonistic free IL-18 specific antibody including any functionally equivalent antibody or parts thereof according to the present invention, which shows cross-reactivity with the IL-18/IL-18BP complex of ≤0.01% and ≤0.05%, particularly of between ≤0.1% and ≤0.2%, particularly between ≤0.2% and ≤0.5%, particularly of between ≤0.5% and ≤1%, particularly of between ≤1% and ≤2 as determined by competitive ELISA, particularly together with a pharmaceutically acceptable carrier and/or excipient, particularly in a prophylactically and/or therapeutically effective amount.

In a particular embodiment, the present invention provides the pharmaceutical composition of the preceding embodiment, wherein said composition optionally further provides another inhibitor of a pro-inflammatory cytokine or functional fragment thereof, or a regulatory factor, which induces in-situ expression of said inhibitor of pro-inflammatory cytokine or functional fragment thereof, co-therapeutic agents such as anti-inflammatory, bronchodilatory, antihistamine, decongestant or anti-tussive drug substances.

Yet another object of the present invention is to provide the pharmaceutical composition as disclosed in any one of the preceding embodiments, comprising a pharmaceutically acceptable carrier and/or excipient.

The present invention further discloses an expression vector comprising a coding sequence of the IL-18 inhibitor or an IL-18 antisense expressing vector as disclosed in any one of the preceding embodiments, which upon administration to a subject suffering from a disease or disorder or having a predisposition to develop such a disease or disorder as defined in the preceding embodiments leads to in situ expression of IL-18 inhibitor for use in the treatment of the disease or disorder as disclosed in any one of the preceding embodiments.

The present invention further discloses an expression vector comprising an IL-18 antisense expressing vector, which upon administration to a subject suffering from a disease or disorder or having a predisposition to develop such a disease or disorder as defined in the embodiments of the present invention, leads to in situ inhibition of the expression of IL-18 for use in the treatment of the disease or disorder as defined in any one of the preceding embodiments.

The present invention further discloses an expression vector comprising the coding sequence of a regulatory factor, which upon administration to a subject suffering from a disease or disorder or having a predisposition to develop such a disease or disorder as disclosed in any one of the preceding embodiments, leads to in situ expression of said regulatory factor, which modulates upstream signaling pathways that control the expression of the IL-18 inhibitor as disclosed in any one of the preceding embodiments, particularly said regulatory factor induces the cellular expression of IL-18 inhibitor for use in the treatment of the disease or disorder as disclosed in any one of the preceding embodiments.

In particular, said expression vector as disclosed in any one of the preceding embodiments for use in the treatment of the disease or disorder as defined in any one of the preceding embodiment is administered to a subject suffering from such a disease or disorder as disclosed in any one of the preceding embodiments, or having a predisposition to develop such a disease or disorder, alone or in combination with the IL-18 inhibitor as disclosed in any one of the preceding embodiments, the Interleukin-18 Binding Protein (IL-18BP) as disclosed in any one of the preceding embodiments or the pharmaceutical composition as disclosed in any one of the preceding embodiments.

The present invention further discloses an expression vector comprising the coding sequence of IL-18BP as disclosed in any one of the preceding embodiments, which upon administration to a subject suffering from a disease or disorder or having a predisposition to develop such a disease or disorder as defined in the preceding embodiments, leads to in situ expression of IL-18BP for use in the treatment of the disease or disorder as defined in any one of the preceding embodiments.

The present invention further discloses an expression vector comprising the coding sequence of a regulatory factor, which upon administration to a subject suffering from a disease or disorder or having a predisposition to develop such a disease or disorder as defined in any one of the preceding embodiments, leads to in situ expression of said regulatory factor, which modulates upstream signaling pathways that control the expression of the IL-18BP as disclosed in any one of the preceding embodiments, particularly said regulatory factor induces the cellular expression of IL-18BP for use in the treatment of the disease or disorder as defined in any one of the preceding embodiments.

In particular, said expression vector as disclosed in any one of the preceding embodiments for use in the treatment of the disease or disorder as defined in any one of the preceding embodiments is administered to a subject suffering from such a disease or disorder as defined in any one of the preceding embodiments, or having a predisposition to develop such a disease or disorder, alone or in combination with the IL-18 inhibitor as disclosed in any one of the preceding embodiments, the Interleukin-18 Binding Protein (IL-18BP) as disclosed in any one of the preceding embodiments or the pharmaceutical composition as disclosed in any one of the preceding embodiments.

Yet another object of the present invention is to provide the IL-18 inhibitor, particularly the IL-18BP, particularly the antagonistic free IL-18 specific antibody, or the pharmaceutical composition comprising the IL-18 inhibitor, particularly the IL-18BP, particularly the antagonistic free IL-18 specific antibody, or the expression vector, for use as disclosed in any one of the preceding embodiments, wherein they are administered to a subject in a prophylactically and/or therapeutically effective amount by systemic, intranasal, intraocular, intravitral, eye drops, buccal, oral, transmucosal, intratracheal, intravenous, subcutaneous, intraurinary tract, intrarectal, intravaginal, sublingual, intrabronchial, intrapulmonary, transdermal or intramuscular administration, in particular broncho-pulmonary administration. In particular, said subject is a mammal, particularly said subject is a human.

The present invention further relates to a method for treating the disease or disorder as defined in any one of the preceding embodiments in a subject suffering from such a disease or disorder, or having a predisposition to develop such a disease or disorder as defined in any one of the preceding embodiments, comprising administering to said subject a therapeutically or prophylactically effective amount of the IL-18 inhibitor, particularly the IL-18BP, particularly the antagonistic free IL-18 specific antibody, or the pharmaceutical composition comprising the IL-18 inhibitor, particularly the IL-18BP, particularly the antagonistic free IL-18 specific antibody, or the expression vector, as disclosed in any one of the preceding embodiments, The present invention further relates to a method of determining the amount of free IL-18 in a sample or in situ comprising detecting the specific binding of the free IL-18 specific binding molecule of any one of the preceding embodiments to free IL-18 protein in the sample or in situ which includes the steps of:
  a) bringing a sample or a specific body part or body area suspected to contain free IL-18 into contact with of the free IL-18 specific binding molecule of any one of the preceding embodiments, which specifically binds to free IL-18, but not to IL-18 bound in a complex and functions as the capturing molecule for free IL-18;
  b) allowing the free IL-18 specific binding molecule to bind to free IL-18;
  c) detecting the binding of IL-18 to the free IL-18 specific binding molecule and determining the amount of free IL-18 in the sample.

In another embodiment, the invention provides a method of diagnosing the diseases or disorder as defined in any one of the preceding embodiments in a patient comprising detecting the specific binding of the free IL-18 specific binding molecule of any one of the preceding embodiments to free IL-18 protein in a sample or in situ which includes the steps of:
  a) bringing a sample or a specific body part or body area suspected to contain free IL-18 into contact with of the free IL-18 specific binding molecule of any one of the preceding embodiments, which specifically binds to free IL-18, but not to IL-18 bound in a complex and functions as the capturing molecule for free IL-18;
  b) allowing the free IL-18 specific binding molecule to bind to free IL-18;

c) detecting the binding of IL-18 to the free IL-18 specific binding molecule and determining the amount of free IL-18 in the sample.
d) comparing the amount of free IL-18 in the sample of the subject suffering from the diseases or disorder as defined in any one of the preceding embodiments to the amount in the sample of a healthy subject.

In still another embodiment, the invention provides a method for diagnosing a predisposition to the diseases or disorder as defined in any one of the preceding embodiments in a patient comprising detecting the specific binding of the free IL-18 specific binding molecule of any one of the preceding embodiments to free IL-18 protein in a sample or in situ which includes the steps of:
a) bringing a sample or a specific body part or body area suspected to contain free IL-18 into contact with of the free IL-18 specific binding molecule of any one of the preceding embodiments, which specifically binds to free IL-18, but not to IL-18 bound in a complex and functions as the capturing molecule for free IL-18;
b) allowing the free IL-18 specific binding molecule to bind to free IL-18;
c) detecting the binding of IL-18 to the free IL-18 specific binding molecule and determining the amount of free IL-18 in the sample.
d) comparing the amount of free IL-18 in the sample of the patient suffering from the diseases or disorder as defined in any one of the preceding embodiments to the amount in the sample of a healthy patient;
wherein an increase in the amount of said free-IL-18 in the sample compared to a normal control value obtained from a healthy patient indicates that said patient is suffering from or is at risk of developing a disease or disorder as defined in any one of the preceding embodiments.

Further comprised herein is a method for monitoring minimal residual disease in a patient following treatment with the IL-18 inhibitor, the pharmaceutical composition, or the expression vector of any one of the preceding embodiments, wherein said method comprises:
a) bringing a sample or a specific body part or body area suspected to contain free IL-18 into contact with of the free IL-18 specific binding molecule of any one of the preceding embodiments, which specifically binds to free IL-18, but not to IL-18 bound in a complex and functions as the capturing molecule for free IL-18;
b) allowing the free IL-18 specific binding molecule to bind to free IL-18;
c) detecting the binding of IL-18 to the free IL-18 specific binding molecule and determining the amount of free IL-18 in the sample.
d) comparing the amount of free IL-18 in the sample of the patient suffering from the diseases or disorder as defined in any one of the preceding embodiments to the amount in the sample of a healthy patient;
wherein an increase in the amount of said free-IL-18 in the sample compared to a normal control value obtained from a healthy patient indicates that said patient is still suffering from a minimal residual disease.

The invention further relates to a method for predicting responsiveness of a patient to a treatment with the IL-18 inhibitor, the pharmaceutical composition, or the expression vector of any one of the preceding embodiments, wherein said method comprises:
a) bringing a sample or a specific body part or body area suspected to contain free IL-18 into contact with of the free IL-18 specific binding molecule of any one of the preceding embodiments, which specifically binds to free IL-18, but not to IL-18 bound in a complex and functions as the capturing molecule for free IL-18;
b) allowing the free IL-18 specific binding molecule to bind to free IL-18;
c) detecting the binding of IL-18 to the free IL-18 specific binding molecule and determining the amount of free IL-18 in the sample.
d) comparing the amount of free IL-18 in the sample of the patient suffering from the diseases or disorder as defined in any one of the preceding embodiments to the amount in the sample of a healthy patient;
wherein a decrease in the amount of said free-IL-18 in the sample indicates that said patient has a high potential of being responsive to the treatment.

Any of the methods may comprise the additional step of using in step a) an IL-18BP specific binding molecule, which binds to a different site of IL-18BP than the capturing molecule, particularly wherein one of said molecules binds to the IL-18 binding site of IL-18BP.

Further, any of the above methods may further comprise the additional step of determining in the sample the presence of free IL-18BP by using in step a) an IL-18BP specific capturing molecule and an IL-18BP specific detection molecule, which binds to a different site of IL-18BP than the capturing molecule, particularly, wherein one of said IL-18BP specific molecules binds to the IL-18 binding site of IL-18BP, by determining in step c) the amount of free and total IL-18 and of free and total IL-18BP bound to the capturing molecule in the sample; and by comparing in step d) the amount of free and/or total IL-18 and free and/or total IL-18BP in the sample of the patient suffering from the diseases or disorder as defined in any one of the preceding embodiments to the amount in the sample of a healthy patient.

The capturing molecule used in any of the above methods may be the free IL-18 specific binding molecule according to any one of the preceding embodiments, particularly the IL-18 BP as described herein or the free IL-binding antibody according to the invention and as described herein.

The sample used in any of the above methods may be a sample selected from the group consisting of bronchoalveolar lavage fluid (BALF) circulation fluids, secretion fluids, biopsyand homogenized tissue, particularly serum, urine, tear, saliva, bile, sweat, exhalation, expiration, sputum, bronchoalveolar fluid, sebum, cellular, gland, mucosa and tissue secretion etc.

In one embodiment, the amount of free IL-18 in the sample of a subject, particularly a human, suffering from any of the diseases disclosed herein are ≥5 pg/mL and up to 10000 pg/mL or higher. In particular, said elevated levels of free IL-18 in a sample form a diseased patient or subject are in the range of ≥5 pg/mL to 10000 pg/mL, particularly in the range of 100 pg/mL to 10000 pg/mL, particularly in the range of 200 pg/mL to 10000 pg/mL, particularly in the range of 300 pg/mL to 10000 pg/mL, particularly in the range of 400 pg/mL to 10000 pg/mL, particularly in the range of 500 pg/mL to 10000 pg/mL, particularly in the range of 600 pg/mL to 10000 pg/mL, particularly in the range of 700 pg/mL to 10000 pg/mL, particularly in the range of 800 pg/mL to 10000 pg/mL, particularly in the range of 900 pg/mL to 10000 pg/mL, particularly in the range of 1000 to 10000 pg/mL, particularly in the range of 1500 pg/mL to 10000 pg/mL, particularly in the range of 2000 pg/mL to 10000 pg/mL, particularly in the range of 3000 pg/mL to 10000 pg/mL, particularly in the range of 4000 pg/mL to 10000 pg/mL, particularly in the range of 5000 pg/mL to 10000 pg/mL. The amount of free IL-18 in serum of healthy subject, particularly a healthy human is ≤5 pg/mL, particularly ≤4 pg/mL, particularly ≤1 pg/mL, particularly ≤0.5 pg/m, particularly below detection level.

In particular, the amount of free IL-18 in isolated sample of a subject, particularly a human, suffering from any of the diseases disclosed herein are ≥5 pg/mL and, particularly, up to 10000 pg/mL, whereas the amount of free IL-18 in sample of a healthy subject, particularly a healthy human, is ≤4 pg/mL.

In another embodiment of the invention, a set of biomarkers is provided for use in any of the above detection method for further specifying the diseases or disorder as defined in any one of the preceding embodiments, for diagnosing a predisposition to the disease or disorder as defined in any one of the preceding embodiments, for monitoring minimal residual disease in a subject, or for predicting responsiveness of a subject to a treatment with IL-18 inhibitor, the pharmaceutical composition, or the expression vector of any one of the preceding embodiments comprising determining a biomarker profile and correlating the obtained profile with a specific disease or disorder.

In particular, the biomarker may be used in a method for diagnosis of the diseases or disorder as defined in any one of the preceding embodiments, for diagnosing a predisposition to the disease or disorder as defined in any one of the preceding embodiments or for monitoring minimal residual disease in a subject, or for predicting responsiveness of a subject to a treatment with IL-18 inhibitor as disclosed in any one of the preceding embodiments, the IL-18BP as disclosed in any one of the preceding embodiments or the pharmaceutical composition comprising IL-18 inhibitor as disclosed in any one of the preceding embodiments comprising the steps of:
a) obtaining a biomarker profile of a subject to be tested by taking a sample of a body fluid from said subject;
b) obtaining a biomarker profile of a healthy reference population;
c) obtaining a biomarker profile from a population which suffers from said disease or disorder and
d) comparing the biomarker profile obtained in step a) with the profile obtained in step b) and step c).

Yet another object of the present invention is to provide a set of biomarkers for use in the diagnosis of the diseases or disorder as defined in any one of the preceding embodiments, for use in the diagnosing a predisposition to the disease or disorder as defined in any one of the preceding embodiments or for use in monitoring minimal residual disease in a subject, or for predicting responsiveness of a subject to a treatment with the IL-18 inhibitor as disclosed in any one of the preceding embodiments, the IL-18BP as disclosed in any one of the preceding embodiments or the pharmaceutical composition comprising IL-18 inhibitor as disclosed in any one of the preceding embodiments, comprising a) IL-18, IL-18BP, IL-13, IL-17A, IL-8, IL-1β, IL-2, IL-12, IL-4, IL-6, INF-γ, TNF-α, VEGF, EGF, HB-EGF, TGF-α, MMP-9, MMP-12, myeloperoxidase, calprotectin measured by immunoassays, TGF-β, Tissue inhibitor of metalloproteinases (TIMP-1), hepatocyte growth factor (HGF), hypoxia induced factor 1 alpha (HIF-1α), von Willebrand factor (vWF), EN-RAGE, S-RAGE, surfactant protein D, HsCRP, fibrinogen, endothelial microparticles, and b) gases comprising NO, CO, alkanes, pentanes, ethanes measured by exhaled air composition.

Yet another object of the present invention is to provide a pharmaceutical kit comprising IL-18 inhibitor as disclosed in any one of the preceding embodiments, Interleukin-18 Binding Protein (IL-18BP) as disclosed in any one of the preceding embodiments or a pharmaceutical composition comprising IL-18 inhibitor as disclosed in any one of the preceding embodiments and a pharmaceutically acceptable carrier and/or excipient according to the present invention in separate unit dosage forms, said forms being suitable for administration in effective amounts.

In one embodiment, the present invention provides a diagnostic kit for detecting free IL-18, comprising the free IL-18 specific binding molecule of any one of the preceding embodiments as the capturing molecule, and a second IL-18 specific binding molecule as the detection molecule and, optionally, a second IL-18 specific capturing molecule, wherein the detection molecule binds to different sites of IL-18 than the capturing molecule.

In another embodiment, a diagnostic kit is provided for detecting total IL-18 or total IL-18BP, comprising a first IL-18BP specific binding molecule, which does not bind to the IL-18 binding site of IL-18BP and a second IL-18 specific binding molecule, which does not bind to the IL-18BP binding site of IL-18.

Also comprised herein is a diagnostic kit for detecting free IL-18BP, comprising a first IL-18BP specific binding molecule as the capturing molecule and second IL-18 specific binding molecule as the detection molecule, wherein said detection molecule binds to a different site of IL-18BP than the capturing molecule.

In one embodiment, the diagnostic kit incorporates a combination of some or all the binding molecules contained in the above defined diagnostic kits.

It is yet another object of the present invention to provide a diagnostic kit for detecting free IL-18, comprising an IL-18-specific antibody as disclosed in any one of the preceding embodiments as capturing antibody or the IL-18BP as alternative capturing molecule, and a second IL-18 specific detection antibody or an IL-18-specific antibody as disclosed in any one of the preceding embodiments as detection antibody and a second IL-18 specific capturing antibody, wherein the detection antibody bind to different sites of IL-18 than the capturing molecule.

Yet another object of the present invention is to provide a diagnostic kit for detecting total IL-18 or total IL-18BP, comprising a first monoclonal IL-18BP specific antibody which does not bind to the IL-18 binding site of IL-18BP and a second IL-18 specific antibody, which does not bind to the IL-18BP binding site of IL-18.

It is yet another object of the present invention to provide a diagnostic kit for detecting free IL-18BP, comprising a first monoclonal IL-18BP specific capturing antibody and an IL-18BP specific detection antibody, which binds to a different site of IL-18BP than the capturing antibody.

In another embodiment, the present invention provides a diagnostic kit, which comprises all diagnostic kits as disclosed in any one of the preceding embodiments.

The present invention now provides IL-18BP, for use in the treatment of an IL-18 associated disease or disorder in a subject suffering from such a disease or disorder or having a predisposition to develop such a disease or disorder, by administering to said subject a therapeutically effective amount of at least one IL-18BP.

IL-18BP is understood within the scope of the present invention to also include muteins of IL-18BP, functional parts or derivatives of IL-18BP, circularly permuted derivatives of IL-18BP, fused proteins comprising IL-18BP, isoforms of IL-18BP or salts thereof.

IL-18BP may be provided as such or in form of a composition, particularly a pharmaceutical composition. Said compositions may comprise additional medicinal agents, pharmaceutical agents, carriers, buffers, dispersing agents, diluents, co-therapeutic agents such as anti-inflammatory, bronchodilatory, antihistamine, decongestant or anti-tussive drug substances and the like depending on the intended use and application.

Thus, the present invention provides IL-18BP or a pharmaceutical composition comprising IL-18BP and a pharmaceutically acceptable carrier and/or excipient for use in the treatment of an IL-18 associated disease or disorder in a subject suffering from such a disease or disorder or having a predisposition to develop such a disease or disorder.

Further provided is an IL-18BP or a pharmaceutical composition comprising IL-18BP and a pharmaceutically acceptable carrier and/or excipient according to the present invention, for treatment of an IL-18 associated disease or disorder in a subject in need of such a treatment, wherein the IL-18 associated disease or disorder is caused by excess expression of IL-18 in specific tissues and/or body compartments, which leads to an IL-18/IL-18BP imbalance in said tissues and/or compartments. For example, the enhanced expression of IL-18 as described herein leads to elevated levels of IL-18 in lung, serum, sputum, broncho-alveolar lavage fluid (BALF) or circulation of said subject compared to healthy control subjects, in particular the levels of IL-18 in sputum and/or in serum are elevated.

The IL-18 associated disease or disorder as described herein in various embodiments of the present invention is caused by excess expression of IL-18. Accordingly, the enhanced expression of IL-18 as described herein leads to elevated levels of IL-18 in lung, serum, sputum, broncho-alveolar lavage fluid (BALF) and/or circulation of a subject suffering from such a disease or disorder or having a predisposition to develop such a disease or disorder, compared to healthy control subjects, especially IL-18 levels in sputum and/or serum are elevated. Further, the elevated levels of IL-18 lead to an IL-18/IL-18BP imbalance in a subject suffering from such a disease or disorder.

In a specific embodiment, the present invention provides IL-18BP or a pharmaceutical composition comprising IL-18BP and a pharmaceutically acceptable carrier and/or excipient for use in compensation of an IL-18/IL-18BP imbalance in a subject suffering a IL-18 associated disease or disorder as described in the various embodiments of the present invention or having a predisposition for such a disease or disorder, by trapping the excess of IL-18. In particular IL-18BP reduces the levels of IL-18 compared to an untreated subject.

In a further embodiment, the present invention provides IL-18BP or a pharmaceutical composition comprising IL-18BP and a pharmaceutically acceptable carrier and/or excipient for use in the treatment of IL-18 associated disease or disorder according to the present invention, wherein IL-18BP leads to an inhibition of the expression of IL-18. In particular IL-18BP reduces the levels of IL-18 towards those of an untreated subject.

The present invention further provides IL-18BP or a pharmaceutical composition comprising IL-18BP and a pharmaceutically acceptable carrier and/or excipient for the use in the treatment of IL-18 induced local and systemic manifestations of inflammation.

The present invention further provides IL-18BP or a pharmaceutical composition comprising IL-18BP and a pharmaceutically acceptable carrier and/or excipient for the use in the treatment of IL-18 induced local and systemic manifestations of inflammation and associated comorbidities such as emphysema, tissue inflammation, tissue destruction, lung resection, disappearance of the vasculature, mucous metaplasia, cardiac hypertrophy, decrease of VEGF in the lung tissue, pulmonary vessel loss, vessel muscularization, collagen deposition, aberrant elastin layers in the lung, fibrotic airway remodeling, airspace enlargement, chronic remodeling of the airways and pulmonary vessels and/or decreased pulmonary function.

In another aspect of the present invention, the increased levels of IL-18 as disclosed by the present invention, trigger an enhanced expression of IFN-γ, IL-13 or IL-17A in subjects suffering from said IL-18 associated disease or disorder compared to healthy control subjects. The present invention, thus, provides IL-18BP or a pharmaceutical composition comprising IL-18BP and a pharmaceutically acceptable carrier and/or excipient for modulating, particularly for reducing, the expression and/or production of IFN-γ, IL-13 or IL-17A in a subject.

In certain embodiments of the present invention, IL-18BP or a pharmaceutical composition comprising IL-18BP and a pharmaceutically acceptable carrier and/or excipient lead to inhibition of IL-18 binding to the IL-18 Receptor (IL-18R), particularly IL-18 binding to the IL-18 Receptor-α (IL-18Rα).

The manifestation of IL-18 associated disease or disorder is triggered by a Th1 cytokine response and/or a Th2 cytokine response. The IL-18BP or a pharmaceutical composition comprising IL-18BP and a pharmaceutically acceptable carrier and/or excipient of the present invention thus leads to inhibition of Th1 cytokine response and/or Th2 cytokine response.

In certain embodiments of the present invention, IL-18BP or a pharmaceutical composition comprising IL-18BP and a pharmaceutically acceptable carrier and/or excipient leads to modulation of IL-18-dependent downstream signaling pathways, e.g. like pathways which regulate TNF-alpha, IL-1beta, IL-8, macrophage inflammatory protein-alpha (MIP-alpha), IL-12, IL-15 and nitric oxide production and/or release. In particular, said signaling pathways are inhibited.

In one embodiment of the present invention, IL-18BP or a pharmaceutical composition comprising IL-18BP and a pharmaceutically acceptable carrier and/or excipient prevents caspase activation. In particular, said caspase is caspase-1.

In one embodiment the present invention provides IL-18BP or a pharmaceutical composition comprising IL-18BP and a pharmaceutically acceptable carrier and/or excipient for use in the treatment of IL-18-associated disease, such as chronic obstructive pulmonary disease (COPD), heart disease and diabetes type 2.

In one embodiment the present invention provides IL-18BP or a pharmaceutical composition comprising IL-18BP and a pharmaceutically acceptable carrier and/or excipient for use in the treatment of IL-18-associated disease, such as chronic obstructive pulmonary disease (COPD), transfusion-related lung injury, bronchopulmonary dysplasia (BPD), acute respiratory distress syndrome (ARDS), Adult Still's disease, juvenile Still's disease, interstitial lung disease (ILD), idiopathic pulmonary fibrosis, cystic fibrosis, pulmonary arterial hypertension, asthma, bronchiectasis, heart failure, amyotrophic lateral sclerosis (ALS), dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behçet's disease, conjunctivitis, allergic conjunctivitis, dermatitis of eyelid, diabetes type 2, non-alcoholic fatty liver disease (NAFLD), steato hepatitis, solid organ and hematologic transplantation, ischemia reperfusion injury, familial Mediterranean fever, tumor necrosis factor receptor 1-associated periodic syndromes, cryopyrin-associated periodic fever syndromes, hyper-IgD syndromes, gout, Schnitzler syndrome, Wegener's granulomatosis also called granulomatosis with polyangitis (GPA), Hashimoto's thyroiditis, Crohn's disease, ulcerative colitis, immunoglobulin-4 (IgG4)-related diseases and stem cell therapies.

In a particular embodiment, the present invention provides IL-18BP or a pharmaceutical composition comprising IL-18BP and a pharmaceutically acceptable carrier and/or excipient for use in the treatment of IL-18-associated lung disease or disorder, heart disease or disorder or diabetes mellitus type 2 as defined herein.

More particular, said IL-18 associated disease or disorder to be treated is manifested in the lung of the subject and may lead to the development of chronic obstructive pulmonary disease (COPD) associated with systemic manifestations of inflammation and associated comorbidities such as emphysema, tissue inflammation, tissue destruction, lung resection, disappearance of the vasculature, mucous metaplasia, cardiac hypertrophy, decrease of VEGF in the lung tissue, pulmonary vessel loss, pulmonary vessel muscularization, collagen deposition in the lung, aberrant elastin layers in the lung, fibrotic airway remodeling, airspace enlargement, chronic remodeling of the airways and pulmonary vessels and/or decreased pulmonary function. In particular, said manifestation is smoke-induced pulmonary inflammation. In a specific embodiment, the present invention provides IL-18BP or a pharmaceutical composition comprising IL-18BP and a pharmaceutically acceptable carrier and/or excipient according to the present invention for use in the treatment of chronic obstructive pulmonary disease (COPD).

The observed IL-18/IL-18BP imbalance in a subject and the resulting disease or disorder as described herein, such as COPD may be caused by smoking or second-hand smoke exposure, in particular tobacco smoke exposure and/or a viral infection. In particular, cigarette smoke exposure may lead to the development of smoke-induced pulmonary emphysema and/or inflammation.

In another aspect of the present invention, the IL-18 associated disease or disorder to be treated is induced by long-term exposure to air pollution.

The present invention, thus, further provides IL-18BP or a pharmaceutical composition comprising IL-18BP and a pharmaceutically acceptable carrier and/or excipient, for treating IL-18 induced airway and vascular remodeling, thus, preventing COPD disease manifestation and progression.

In one aspect of the present invention, alveolar macrophages are an important source of increased IL-18 level. Thus, the IL-18BP or a pharmaceutical composition comprising IL-18BP and a pharmaceutically acceptable carrier and/or excipient, as provided by the present invention, reduces the expression and/or production of IL-18 by alveolar macrophages.

The present invention further provides IL-18BP or a pharmaceutical composition comprising IL-18BP and a pharmaceutically acceptable carrier and/or excipient for preventing and/or inhibiting a smoke-induced form of cell death of lung tissue cells and/or epithelial cells affected by the IL-18 associated disease or disorder as described herein. In particular, said smoke-induced form of cell death is apoptosis.

In one embodiment of the present invention, the pharmaceutical composition of the invention and as disclosed herein in the various embodiments is administered prophylactically.

In another embodiment of the present invention, the pharmaceutical composition of the invention and as disclosed herein in the various embodiments is administered therapeutically.

In one embodiment of the present invention, the pharmaceutical composition of the invention and as disclosed herein in the various embodiments is administered to a subject suffering from IL-18 associated disease or disorder, or having a predisposition to develop such a disease or disorder by systemic, intranasal, intraocular, intravitral, eye drops, buccal, oral, transmucosal, intratracheal, intravenous, subcutaneous, intraurinary tract, intrarectal, intravaginal, sublingual, intrabronchial, intrapulmonary, transdermal or intramuscular administration. In particular, the pharmaceutical composition of the invention and as disclosed herein in the various embodiments is administered by broncho-pulmonary administration.

The pharmaceutical composition of the invention and as disclosed herein in the various embodiments may be provided as a liquid, liquid spray, microspheres, semisolid, gel, or powder for transmucosal administration, e.g. intranasal, buccal, oral transmucosal, intratracheal, intraurinary tract, intravaginal, sublingual, intrabronchial, intrapulmonary and/or transdermal administration. Further, the composition may be in a solid dosage form for buccal, oral transmucosal and/or sublingual administration. Intranasal, buccal, oral intratracheal, intraurinary tract, intravaginal, transmucosal and sublingual administrations lead to the disintegration of the composition as described herein in an oral cavity at body temperature and optionally may adhere to the body tissue of the oral cavity. Additionally, the composition as disclosed herein further may include one or more excipient, diluent, binder, lubricant, glidant, disintegrant, desensitizing agent, emulsifier, mucosal adhesive, solubilizer, suspension agent, viscosity modifier, ionic tonicity agent, buffer, carrier, surfactant, flavor, or mixture thereof.

In a specific aspect of the present invention, the composition is formulated as a parenteral, intravenous, tablet, pill, bioadhesive patch, drops, sponge, film, lozenge, hard candy, wafer, sphere, lollipop, disc-shaped structure, suppository or spray.

Transmucosal administration is generally rapid because of the rich vascular supply to the mucosa and the lack of a stratum corneum in the epidermis. Such drug transport typically provides a rapid rise in blood concentrations, and similarly avoids the enterohepatic circulation and immediate destruction by gastric acid or partial first-pass effects of gut wall and hepatic metabolism. Drugs typically need to have prolonged exposure to a mucosal surface for significant drug absorption to occur.

The transmucosal routes can also be more effective than the oral route in that these routes can provide for relatively faster absorption and onset of therapeutic action. Further, the transmucosal routes can be preferred for use in treating patients who have difficulty in swallowing tablets, capsules, or other oral solids, or those who have disease-compromised intestinal absorption. Accordingly, there are many advantages to transmucosal administration of IL-18BP or a pharmaceutical composition comprising IL-18BP and a pharmaceutically acceptable carrier and/or excipient.

In either of the intranasal or buccal routes, drug absorption can be delayed or prolonged, or uptake may be almost as rapid as if an intravenous bolus were administered.

Because of the high permeability of the rich blood supply, the sublingual route can provide a rapid onset of action.

The intranasal compositions can be administered by any appropriate method according to their form. A composition including microspheres or a powder can be administered using a nasal insufflator device. Examples of these devices are well known to those of skill in the art, and include commercial powder systems such as Fisons Lomudal System. An insufflator produces a finely divided cloud of the dry powder or microspheres. The insufflator is preferably provided with a mechanism to ensure administration of a substantially fixed amount of the composition. The powder or microspheres can be used directly with an insufflator, which is provided with a bottle or container for the powder or microspheres. Alternatively, the powder or microspheres can be filled into a capsule such as a gelatin capsule, or other single dose device adapted for nasal administration. The insufflator preferably has a mechanism to break open the capsule or other device. Further, the composition can provide an initial rapid release of the active ingredient followed by a sustained release of the active ingredient, for example, by providing more than one type of microsphere or powder. Further, alternative methods suitable for administering a composition to the nasal cavity will be well known by the person of ordinary skill in the art. Any suitable method may be used. For a more detailed description of suitable methods reference is made to EP2112923, EP1635783, EP1648406, EP2112923 (the entire contents of which are incorporated by reference herein).

In one embodiment of the present invention, the pharmaceutical composition of the invention and as disclosed herein in the various embodiments is may be further administered intranasally, i.e. by inhalation and, thus, may be formulated in a form suitable for intranasal administration, i.e. as an aerosol, dry powder formulation or a liquid preparation.

Examples of suitable pharmaceutical carriers, excipients and/or diluents are well known in the art and include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulation are aqueous or non-aqueous solutions, suspensions, dry powder formulations, emulsions or oils. Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, fish-liver oil, another marine oil, or a lipid from milk or eggs.

The present invention also relates to transpulmonary administration by inhalation of the pharmaceutical composition of the invention and as disclosed herein in the various embodiments is in dry powder, gaseous or volatile formulations into systemic circulation via the respiratory tract. Absorption is virtually as rapid as the formulation can be delivered into the alveoli of the lungs, since the alveolar and vascular epithelial membranes are quite permeable, blood flow is abundant and there is a very large surface for adsorption. For instance, aerosols my be delivered from pressure-packaged, metered-dose inhalers (MDIs).

The pharmaceutical composition of the invention and as disclosed herein in the various embodiments is will generally be administered in a mixture with a suitable pharmaceutical excipient, diluent or carrier selected with regard to the chosen means of inhalation and standard pharmaceutical practice.

In another embodiment of the invention, the IL-18BP formulation or the formulation of a pharmaceutical composition comprising IL-18BP is a dry powder, optionally together with at least one particulate pharmaceutically acceptable carrier, which may be one or more materials known as pharmaceutically acceptable carriers, preferably chosen from materials known as carriers in dry powder inhalation compositions, for example saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. An especially preferred carrier is lactose, for example lactose monohydrate or anhydrous lactose. The dry powder may be contained as unit doses in capsules of, for example, gelatin or plastic, or in blisters (e.g. of aluminium or plastic), for use in a dry powder inhalation device, which may be a single dose or multiple dose device, preferably in dosage units together with the carrier in amounts to bring the total weight of powder per capsule to from 5 mg to 50 mg. Alternatively, the dry powder may be contained in a reservoir in a multi-dose dry powder inhalation (MDDPI) device adapted to deliver.

Any other therapeutically efficacious route of administration can be used, for example absorption through epithelial or endothelial tissues or by gene therapy wherein a DNA molecule encoding the active agent is administered to the patient (e.g. via an expression vector), which causes the active agent to be expressed and secreted in vivo.

In the body, expression of IL-18BP can be induced by modulating upstream signaling pathways, which control the expression of IL-18BP. For instance, IL-18BP is specifically induced by IFN-gamma as part of a negative feedback loop that regulates the induction of IFN-gamma by IL-18. Other known factors which are reported to regulate IL-18BP expression are IL-18, IL-27, IFN-alpha and STAT1.

Thus, in one embodiment of the present invention, cellular expression of IL-18BP is indirectly induced by modification of one or more upstream signaling pathways, which control the expression of IL-18BP. In particular, expression of IL-18BP is indirectly induced by modification of at least one upstream signaling pathway.

The invention further relates to an expression vector comprising the coding sequence of IL-18BP in the preparation of a medicament for the treatment of IL-18 associated disease or disorder as described herein in a subject suffering from such a disease or disorder or having a predisposition to develop such a disease or disorder.

In a specific embodiment, the present invention relates to an expression vector comprising the coding sequence of a regulatory factor, which modulates upstream signaling pathways that regulate the expression of IL-18BP. Thus, said regulatory factor induces the expression of IL-18BP by modulating at least one upstream signaling pathway.

The invention further relates to an expression vector comprising the coding sequence of a regulatory factor, which modulates upstream signaling pathways that regulate the expression of IL-18BP in the preparation of a medicament for the treatment of IL-18 associated disease or disorder as described herein in a subject suffering from such a disease or disorder or having a predisposition to develop such a disease or disorder.

The invention further relates to an expression vector comprising the coding sequence of a regulatory factor, which induces the expression of IL-18BP for the treatment of IL-18 associated disease or disorder as described herein in a subject suffering from such a disease or disorder or having a predisposition to develop such a disease or disorder. In particular it relates to an expression vector comprising the coding sequence of a regulatory factor, which induces the expression of IL-18BP in the lung for the treatment of IL-18 associated disease or disorder as described herein in a subject suffering from such a disease or disorder or having a predisposition to develop such a disease or disorder.

Optionally the present invention provides a second expression vector comprising the coding sequence of a second naturally occurring proinflammatory cytokine inhibitor or a regulatory factor which modulates at least one upstream signaling pathway that regulates the expression of said proinflammatory cytokines. In particular, said regulatory factor induces the expression of said cytokine inhibitor.

In particular, the expression of IL-18 is modulated by RNA interference (RNAi) or an IL-18 antisense expressing vector. More particular, the expression of IL-18 is modulated by RNA interference (RNAi), wherein the expression of IL-18 is downregulated by post transcriptional gene silencing (PTGS). In particular, the expression of IL-18 is downregulated in the lung of the subject suffering from the disease or disorder as disclosed herein. The mechanism of RNA interference comprises any post transcriptional gene silencing event, particularly any post transcriptional gene silencing event induced by microRNA (miRNA) or small interfering RNA (sRNA). MicroRNAs (miRNAs) and small interfering RNAs (siRNAs) can be expressed by the expression vector according to the invention and as described herein.

A gene therapeutical approach may thus be used for treating an IL-18 associated disease or disorder as described herein and as disclosed in the various embodiments. Accordingly, the expression of IL-18BP occurs in situ, hence, directly neutralizing IL-18 in the tissue or cells affected by said disease or disorder. In particular, the expression of IL-18BP as disclosed herein is induced in the lung.

The pharmaceutical composition of the invention and as disclosed herein in the various embodiments may be used for treatment of an IL-18 associated disease or disorder as described herein in the various embodiments in human and veterinary medicine for treating humans and animals, including avians, non-human primates, dogs, cats, pigs, goats, sheep, cattle, horses, mice, rats and rabbits.

In a specific embodiment, the present invention provides the pharmaceutical composition of the invention as disclosed herein in the various embodiments for use in the treatment of IL-18 associated disease or disorder as described herein in the various embodiments, wherein the subject is a mammal, in particular the subject is a human.

In another specific embodiment, the pharmaceutical composition of the invention as disclosed herein in the various embodiments is administered in a therapeutically effective amount with a suitable dose of at least a second proinflammatory cytokine inhibitor. In particular said inhibitor is specific for IL-1, IL-6, IL-13, IL-17A, IFN-$\gamma$ or TNF$\alpha$.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well known conventional methods. Suitable carriers may comprise any material which, when combined with the biologically active compound of the invention, retains the biological activity.

Efforts have been made in the art to chemically modify the barrier properties of skin to permit the penetration of certain agents, enhance the effectiveness of the agent being delivered, enhance delivery times, reduce the dosages delivered, reduce the side effects from various delivery methods, reduce patient reactions, and so forth.

In this regard, penetration enhancers have been used to increase the permeability of the dermal surface to drugs, and are often proton accepting solvents such as dimethyl sulfoxide (DMSO) and dimethylacetamide. Other penetration enhancers that have been studied and reported as effective include 2-pyrrolidine, N,N-diethyl-m-toluamide (Deet), 1-dodecal-azacycloheptane-2-one, N,N-dimethylformamide, N-methyl-2-pyrrolidine, calcium thioglycolate, hexanol, fatty acids and esters, pyrrolidone derivatives, derivatives of 1,3-dioxanes and 1,3-dioxolanes, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 1-azacycloheptan-2-one-2-dodecylacetic acid, and aminoalcohol derivatives, including derivatives of 1,3-dioxanes, among others.

Preparations for transmucosal administration may include sterile aqueous or non-aqueous solutions, suspensions, dry powder formulations and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Transmucosal vehicles may include sodium chloride solution, Ringer's dextrose, dextrose and sodium chloride, lactated Ringer's, or fixed oils. Preservatives and other additives may also be present including, for example, antimicrobials, anti-oxidants, chelating agents, and inert gases and the like. In addition, the pharmaceutical composition of the present invention might comprise proteinaceous carriers, like, e.g., serum albumin or immunoglobulin, preferably of human origin.

The pharmaceutical composition of the invention as disclosed herein in the various embodiments may be administered topically to body surfaces and, thus, be formulated in a form suitable for topical administration. Suitable topical formulations include gels, ointments, creams, lotions, drops and the like. For topical administration, the pharmaceutical composition of the invention as disclosed herein in the various embodiments is prepared and applied as a solution, suspension, or emulsion in a physiologically acceptable diluent with or without a pharmaceutical carrier.

The pharmaceutical composition of the invention and as disclosed herein in the various embodiments may also be administered as controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

Further examples for suitable formulations are provided in WO 2006/085983, the entire contents of which are incorporated by reference herein. For example, the pharmaceutical composition of the invention and as disclosed herein in the various embodiments is of the present invention may be provided as liposomal formulations. The technology for forming liposomal suspensions is well known in the art. The lipid layer employed can be of any conventional composition and can either contain cholesterol or can be cholesterol-free. The liposomes can be reduced in size, as through the use of standard sonication and homogenization techniques. Liposomal formulations containing the pharmaceutical composition of the invention as disclosed herein in the various embodiments can be lyophilized to produce a lyophilizate which can be reconstituted with a pharmaceutically acceptable carrier, such as water, to regenerate a liposomal suspension. The pharmaceutical composition of the invention as disclosed herein in the various embodiments can be administered to the subject at a suitable dose. The dosage regimen will be determined by the attending physician and clinical factors. As is well known in the medical arts, dosages for any one subject depend upon many factors, including the subject's size, body surface area, age, the particular compound to be administered, sex, time and route of administration, general health, and other drugs being administered concurrently.

Furthermore, it is envisaged that the pharmaceutical composition of the invention might comprise further biologically active agents, depending on the intended use of the pharmaceutical composition. These further biologically active agents may be e.g. antibodies, antibody fragments, hormones, growth factors, enzymes, binding molecules, cytokines, chemokines, nucleic acid molecules and drugs. In a preferred embodiment, the pharmaceutical composition of the present invention is to be co-administered with long-acting beta-adrenoceptor agonist (LABA), long-acting muscarinic antagonists (LAMA), steroids, corticosteroid, glucocorticoid and glucocorticoid agonists phosphodiesterase inhibitors, kinase inhibitors, cytokine and chemokine inhibitors or antagonists or protease inhibitors or combinations thereof.

The dosage of the pharmaceutical composition of the invention as disclosed herein in the various embodiments will depend on the condition being treated, the particular composition used, and other clinical factors such as weight, size and condition of the subject, body surface area, the particular compound or composition to be administered, other drugs being administered concurrently, and the route of administration.

The pharmaceutical composition of the invention as disclosed herein in the various embodiments may be administered in combination with other biologically active substances and procedures for the treatment of symptoms associated with IL-18 associated disease, such as chronic obstructive pulmonary disease (COPD), transfusion-related lung injury, bronchopulmonary dysplasia (BPD), acute respiratory distress syndrome (ARDS), Adult Still's disease, juvenile Still's disease, interstitial lung disease (ILD), idiopathic pulmonary fibrosis, cystic fibrosis, pulmonary arterial hypertension, asthma, bronchiectasis, heart failure, amyotrophic lateral sclerosis (ALS), dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behçet's disease, conjunctivitis, allergic conjunctivitis, dermatitis of eyelid, diabetes type 2, non-alcoholic fatty liver disease (NAFLD), steato hepatitis, solid organ and hematologic transplantation, ischemia reperfusion injury, familial Mediterranean fever, tumor necrosis factor receptor 1-associated periodic syndromes, cryopyrin-associated periodic fever syndromes, hyper-IgD syndromes, gout, Schnitzler syndrome, Wegener's granulomatosis also called granulomatosis with polyangitis (GPA), Hashimoto's thyroiditis, Crohn's disease, ulcerative colitis, immunoglobulin-4 (IgG4)-related diseases and stem cell therapies. The other biologically active substances may be part of the same composition already comprising the composition according to the invention, in form of a mixture, wherein the composition of the invention and the other biologically active substance are intermixed in or with the same pharmaceutically acceptable solvent and/or carrier or may be provided separately as part of a separate compositions, which may be offered separately or together in form of a kit of parts.

The pharmaceutical composition of the invention as disclosed herein in the various embodiments may be administered concomitantly with the other biologically active substance or substances, intermittently or sequentially. For example, the composition according to the invention may be administered simultaneously with a first additional biologically active substance or sequentially after or before administration of said composition. If an application scheme is chosen where more than one additional biologically active substance are administered and at least one composition according to the invention, the compounds or substances may be partially administered simultaneously, partially sequentially in various combinations.

It is thus another object of the present invention to provide for mixtures of the pharmaceutical composition of the invention as disclosed herein in the various embodiments, optionally comprising one or more further biologically active substances in a therapeutically or prophylactically effective amount, as well as to methods of using such a composition according to the invention, or mixtures thereof for the prevention and/or therapeutic treatment and/or alleviation of the effects of chronic obstructive pulmonary disease (COPD), heart disease and diabetes type 2.

It is thus another object of the present invention to provide for mixtures of the pharmaceutical composition of the invention as disclosed herein in the various embodiments, optionally comprising, one or more further biologically active substances in a therapeutically or prophylactically effective amount, as well as to methods of using such a composition according to the invention, or mixtures thereof for the prevention and/or therapeutic treatment and/or alleviation of the effects of chronic obstructive pulmonary disease (COPD), transfusion-related lung injury, bronchopulmonary dysplasia (BPD), acute respiratory distress syndrome (ARDS), Adult Still's disease, juvenile Still's disease, interstitial lung disease (ILD), idiopathic pulmonary fibrosis, cystic fibrosis, pulmonary arterial hypertension, asthma, bronchiectasis, heart failure, amyotrophic lateral sclerosis (ALS), dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behçet's disease, conjunctivitis, allergic conjunctivitis, dermatitis of eyelid, diabetes type 2, non-alcoholic fatty liver disease (NAFLD), steato hepatitis, solid organ and hematologic transplantation, ischemia reperfusion injury, familial Mediterranean fever, tumor necrosis factor receptor 1-associated periodic syndromes, cryopyrin-associated periodic fever syndromes, hyper-IgD syndromes, gout, Schnitzler syndrome, Wegener's granulomatosis also called granulomatosis with polyangitis (GPA), Hashimoto's thyroiditis, Crohn's disease, ulcerative colitis, immunoglobulin-4 (IgG4)-related diseases and stem cell therapies.

The other biologically active substance or compound may exert its biological effect by the same or a similar mechanism as the composition according to the invention or by an unrelated mechanism of action or by a multiplicity of related and/or unrelated mechanisms of action.

Generally, the other biologically active compound may include antibodies raised against and binding to INF-gamma, IL-17A, IL-13, IL-1beta, IL-6, IL-2, IL-4, IL-12, TNF-alpha In particular, the mixture according to the invention may comprise IL-18BP (IL-18BP) or a pharmaceutical composition comprising IL-18BP (IL-18BP) and a pharmaceutically acceptable carrier and/or excipient according to the invention and as described herein.

Suitable dosages of the pharmaceutical composition of the invention as disclosed herein in the various embodiments will vary depending upon the condition, age and species of the subject, and can be readily determined by those skilled in the art. The total daily dosages of the employed in both veterinary and human medicine will suitably be in the range 0.01-2000 mg/kg body-weight, preferably from 0.1-1000 mg/kg body-weight, preferably from 1-100 mg/kg and these may be administered as single or divided doses, and in addition, the upper limit can also be exceeded when this is found to be indicated. Such dosage will be adjusted to the individual requirements in each particular case including the specific compound(s) being administered, the route of administration, the condition being treated, as well as the subject being treated. However, the compounds can also be administered as depot preparations (implants, slow-release formulations, etc.) weekly, monthly or at even longer intervals. In such cases the dosage will be much higher than the daily one and has to be adapted to the administration form, the body weight and the concrete indication. The appropriate dosage can be determined by conducting conventional model tests, preferably animal models. An effective dose of active ingredient(s) depends at least on the nature of the condition being treated, toxicity, whether the compound(s) is being used prophylactic ally or against an active infection or condition, the method of delivery, and the pharmaceutical formulation, and will be determined by the clinician using conventional dose escalation studies. It can be expected to be from about 0.01 mg to about 1 g/kg body weight per day. For example, for topical delivery the daily candidate dose for an adult human of approximately 70 kg body weight will range from about 1 mg to about 500 mg, generally between about 5 mg and about 40 mg, and may take the form of single or multiple doses or administration sites. For intranasal delivery the candidate dose can be expected to be from about 0.01 mg to about 1 g/kg body weight per day.

Further, functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, as described in WO 92/13095, for example.

Therefore, in another embodiment of the present invention, IL-18BP is PEGylated.

In still another embodiment of the invention, IL-18BP is a fused protein comprising all or part of an IL-18BP, which is fused to all or part of an immunoglobulin.

In a further embodiment of the invention, the IL-18BP is PEGylated, fused to all or part of an immunoglobulin, preferably to the constant region of an immunoglobulin, and wherein the fused protein is still capable of binding to IL-18. More specifically, the immunoglobulin may be of the IgG1 or IgG2 isotype.

The person skilled in the art will understand that the resulting fusion protein retains the biological activity of IL-18BP, in particular the binding to IL-18. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met) (SEQ ID NO: 9), for example, or a 13-amino acid linker sequence comprising Glu-Phe-Gly-Ala-Gly-Leu-Val-Leu-Gly-Gly-Gln-Phe-Met (SEQ ID NO: 8) introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

Preferably, it is fused to heavy chain regions, like the CH2 and CH3 domains of human IgG1, for example. The generation of specific fusion proteins comprising IL-18BP and a portion of an immunoglobulin are described in example 11 of WP99/09063, for example. Other isoforms of Ig molecules are also suitable for the generation of fusion proteins according to the present invention, such as isoforms IgG2 or IgG4, or other Ig classes, like IgM or IgA, for example. Fusion proteins may be monomeric or multimeric, hetero or homomultimeric.

In certain further embodiments, the present invention provides a method for treating a subject suffering or having a predisposition to develop a disease or disorder associated with excess expression of IL-18 as described herein in various embodiments of the present invention, comprising administering to said subject a therapeutically effective amount of the pharmaceutical composition of the invention as disclosed herein in the various embodiments.

Serological assays are well known in the art and have become a useful tool for the detection of antigens in body fluids, such as serum, bronchial alveolar lavage (BAL) fluid and sputum. However, until now no functional diagnostic assay for the detection of IL-18 by specific antibodies exists. Thus, there is a specific need for a diagnostic method for the detection of IL-18 in body fluid, particularly in serum.

The present invention thus discloses methods and kits for the detection and diagnosis of IL-18-associated diseases or conditions as described herein, for diagnosing a predisposition to an IL18-associated disease or condition as described herein or for monitoring minimal residual disease in a subject or for predicting responsiveness of a subject to a treatment with the pharmaceutical composition of the invention as disclosed herein in the various embodiments is and as described herein before. These methods include known immunological methods commonly used for detecting or quantifying substances in biological samples or in an in situ condition.

In one embodiment the present invention further discloses a method for diagnosis of IL-18-associated disease as described herein, or for diagnosing a predisposition to an IL18-associated disease as described herein, or for monitoring minimal residual disease in a subject or for predicting responsiveness of a subject to a treatment with IL-18BP or a pharmaceutical composition comprising IL-18BP (IL-18BP) and a pharmaceutically acceptable carrier and/or excipient according to any one of the preceding embodiments, comprising the steps:
  a) obtaining a sample of body fluid from a subject suffering from such a disease;
  b) testing said sample for the presence of IL-18 by using the IL-18BP as disclosed herein or the IL-18-specific antibody according to the present invention as capturing molecule;
  c) determining the amount of IL-18 bound to the capturing molecule in the sample;
  d) comparing the amount of IL-18 in the sample of the subject suffering from such a disease to the amount in the sample of a healthy subject.

The amount of free IL-18 in isolated serum of a subject, particularly a human, suffering from said disease ranges from 5 to 10000 pg/mL, particularly in the range of 100 to 10000 pg/mL, particularly in the range of 200 to 10000 pg/mL, particularly in the range of 300 to 10000 pg/mL, particularly in the range of 400 to 10000 pg/mL, particularly in the range of 500 to 10000 pg/mL, particularly in the range of 600 to 10000 pg/mL, particularly in the range of 700 to 10000 pg/mL, particularly in the range of 800 to 10000 pg/mL, particularly in the range of 900 to 10000 pg/mL, particularly in the range of 1000 to 10000 pg/mL, particularly in the range of 1500 to 10000 pg/mL, particularly in the range of 2000 to 10000 pg/mL, particularly in the range of 3000 to 10000 pg/mL, particularly in the range of 4000 to 10000 pg/mL, particularly in the range of 5000 to 10000 pg/mL. The amount of free IL-18 in serum of healthy subject, particularly a healthy human is $\leq 40$ pg/mL, particularly $\leq 30$ pg/mL, particularly $\leq 25$ pg/mL, particularly $\leq 20$ pg/mL, particularly $\leq 10$ pg/mL, particularly $\leq 5$ pg/mL, particularly $\leq 1$ pg/mL, particularly $\leq 0.5$ pg/mL. Thus, a subject having a detectable IL-18 concentration in the serum between 5 to 10000 pg/mL suffers from the IL-18-associated disease as disclosed herein. The amount of IL-18 in serum and other body fluids can be determined by the diagnostic method as disclosed herein by using a linear standard curve, which is calculated for predefined IL-18 concentrations within the range of 5 to 200 pg/mL.

Diagnosis of an IL-18-associated disease or condition or of a predisposition to an IL-18-associated disease or condition as described herein in a subject may be achieved by detecting the binding of IL-18BP as disclosed herein to IL-18 or the immunospecific binding of a monoclonal antibody or an active fragment thereof as disclosed herein to an epitope of IL-18 in a sample or in situ, which includes bringing the sample or a specific body part or body area suspected to contain the IL-18 antigen into contact with IL-18BP and/or an antibody which binds an epitope of the IL-18 protein or a fragment thereof, allowing the IL-18BP or the antibody to bind to the IL-18 antigen to form an immunological complex, detecting the formation of the immunological complex and correlating the presence or absence of the immunological complex with the presence or absence of IL-18 antigen in the sample or specific body part or area, optionally comparing the amount of said immunological complex to a normal control value, wherein an increase in the amount of said aggregate compared to a normal control value indicates that said subject is suffering from or is at risk of developing an IL-18-associated disease or condition.

Monitoring minimal residual disease in a subject following treatment with IL-18BP or a pharmaceutical composition comprising IL-18BP and a pharmaceutically acceptable carrier and/or excipient according to any one of the preceding embodiments and as described herein before may be achieved by detecting the binding of IL-18BP as disclosed herein to IL-18 or the immunospecific binding of a monoclonal antibody or an active fragment thereof as disclosed herein to an epitope of the IL-18 protein or a fragment thereof in a sample or in situ, which includes bringing the sample or a specific body part or body area suspected to contain the IL-18 antigen into contact with the IL-18BP and/or the antibody as disclosed herein which binds an epitope of the IL-18 protein or a fragment thereof, allowing the IL-18BP and/or the antibody to bind to the IL-18 antigen to form an immunological complex, detecting the formation of the immunological complex and correlating the presence or absence of the immunological complex with the presence or absence of IL-18 antigen in the sample or specific body part or area, optionally comparing the amount of said immunological complex to a normal control value, wherein an increase in the amount of said aggregate compared to a normal control value indicates that said subject may still suffer from a minimal residual disease.

Predicting responsiveness of a subject to a treatment with the pharmaceutical composition of the invention as disclosed herein in the various embodiments may be achieved by detecting the binding of IL-18BP as disclosed herein to IL-18 or the immunospecific binding of a monoclonal antibody or an active fragment thereof as disclosed herein to an epitope of the IL-18 protein or a fragment thereof in a sample or in situ, which includes bringing the sample or a specific body part or body area suspected to contain the IL-18 antigen into contact with the IL-18BP and/or the antibody which binds an epitope of the IL-18 protein or a fragment thereof, allowing the IL-18BP and/or antibody to bind to the IL-18 antigen to form an immunological complex, detecting the formation of the immunological complex and correlating the presence or absence of the immunological complex with the presence or absence of IL-18 antigen in the sample or specific body part or area, optionally comparing the amount of said immunological complex before and after onset of the treatment, wherein an decrease in the amount of said aggregate indicates that said subject has a high potential of being responsive to the treatment.

Biological samples that may be used in the diagnosis of an IL-18-associated disease or condition as described herein, for diagnosing a predisposition to an IL-18-associated disease or condition or for monitoring minimal residual disease as described herein in a subject or for predicting responsiveness of a subject to a treatment with the pharmaceutical composition of the invention as disclosed herein in the various embodiments are, for example, fluids such as serum, plasma, saliva, gastric secretions, mucus, cerebrospinal fluid, lymphatic fluid and the like or tissue or cell samples obtained from an organism such as neural, brain, lung, cardiac or vascular tissue. For determining the presence or absence of the IL-18 antigen, particularly of free IL-18 antigen, in a sample any immunoassay known to those skilled in the art may be used. (See Harlow and Lane, Antibodies: A Laboratory Manual (Cold Spring Harbor Laboratory, New York 1988 555-612) may be used such as, for example, assays which utilize indirect detection methods using secondary reagents for detection, ELISA's and immunoprecipitation and agglutination assays. A detailed description of these assays is, for example, given in WO96/13590 to Maertens and Stuyver, Zrein et al. (1998) and WO96/29605.

For in situ diagnosis, the IL-18BP as disclosed herein and/or the IL-18-specific antibody or any active and functional part thereof as disclosed herein may be administered to the organism to be diagnosed by methods known in the art such as, for example, intravenous, intranasal, intraperitoneal, intracerebral, intraarterial injection such that a specific binding between the IL-18BP and/or the specific antibody with an eptitopic region on the IL-18 antigen may occur. The IL-18-IL-BP/antigen or antibody/antigen complex may be detected through a label attached to the antibody or a functional fragment thereof.

The immunoassays used in diagnostic applications or in applications for diagnosing a predisposition to an IL-18-associated disease or condition as described herein or for monitoring minimal residual disease in a subject or for predicting responsiveness of a subject to a treatment with the pharmaceutical composition of the invention as disclosed herein in the various embodiments is typically relying on labelled antigens, antibodies, or secondary reagents for detection. These proteins or reagents can be labelled with compounds generally known to those skilled in the art including enzymes, radioisotopes, and fluorescent, luminescent and chromogenic substances including colored particles, such as colloidal gold and latex beads. Of these, radioactive labelling can be used for almost all types of assays and with most variations. Enzyme-conjugated labels are particularly useful when radioactivity must be avoided or when quick results are needed. Fluorochromes, although requiring expensive equipment for their use, provide a very sensitive method of detection. Antibodies useful in these assays include monoclonal antibodies, polyclonal antibodies, and affinity purified polyclonal antibodies.

Alternatively, the antibody may be labelled indirectly by reaction with labelled substances that have an affinity for immunoglobulin, such as protein A or G or second antibodies. The antibody may be conjugated with a second substance and detected with a labelled third substance having an affinity for the second substance conjugated to the antibody. For example, the antibody may be conjugated to biotin and the antibody-biotin conjugate detected using labelled avidin or streptavidin. Similarly, the antibody may be conjugated to a hapten and the antibody-hapten conjugate detected using labelled anti-hapten antibody.

Those of ordinary skill in the art will know of these and other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1-31), and Schurs, A. H. W. M., et al. 1977 (Clin. Chim Acta 81:1-40). Coupling techniques mentioned in the latter are the glutaraldehyde method, the periodate method, the dimaleimide method, and others, all of which are incorporated by reference herein.

Current immunoassays utilize a double antibody method for detecting the presence of an analyte, wherein the capture antibody is labeled indirectly by reactivity with a second antibody that has been labeled with a detectable label. The second antibody is preferably one that binds to antibodies of the animal from which the monoclonal antibody is derived. In other words, if the monoclonal antibody is a mouse antibody, then the labeled, second antibody is an anti-mouse antibody. For the monoclonal antibody to be used in the assay described below, this label is preferably an antibody-coated bead, particularly a magnetic bead. For the polyclonal antibody to be employed in the immunoassay described herein, the label is preferably a detectable molecule such as a radioactive, fluorescent or an electrochemiluminescent substance.

An alternative double antibody system, often referred to as fast format systems because they are adapted to rapid determinations of the presence of an analyte, may also be employed within the scope of the present invention. The system requires high affinity between the antibody and the analyte. According to one embodiment of the present invention, the presence of the IL-18 antigen is determined using a pair of antibodies, each specific for IL-18 antigen. One of said pairs of antibodies is referred to herein as a "detector antibody" and the other of said pair of antibodies is referred to herein as a "capture antibody". The monoclonal antibody of the present invention can be used as either a capture antibody or a detector antibody. The monoclonal antibody of the present invention can also be used as both capture and detector antibody, together in a single assay. One embodiment of the present invention thus uses the double antibody sandwich method for detecting IL-18 antigen in a sample of biological fluid. In this method, the analyte (IL-18 antigen) is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Exemplary solid phase substances include, but are not limited to, microtiter plates, test tubes of polystyrene, magnetic, plastic or glass beads and slides which are well known in the field of radioimmunoassay and enzyme immunoassay. Methods for coupling antibodies to solid phases are also well known to those skilled in the art. More recently, a number of porous material such as nylon, nitrocellulose, cellulose acetate, glass fibers and other porous polymers have been employed as solid supports.

The present invention also relates to a diagnostic kit for detecting IL-18 antigen in a biological sample. Moreover, the present invention relates to the latter diagnostic kit which, in addition to a composition as defined above, also comprises a detection reagent as defined above. The term "diagnostic kit" refers in general to any diagnostic kit known in the art. More specifically, the latter term refers to a diagnostic kit as described in Zrein et al. (1998).

It is still another object of the present invention to provide novel immunoprobes and test kits for detection and diagnosis of IL-18-associated diseases and conditions as described herein comprising IL-18BP as disclosed herein before or specific IL-18BP antibodies as disclosed herein before. For immunoprobes, the IL-18BP or the antibodies are directly or indirectly attached to a suitable reporter molecule, e.g., an enzyme or a radionuclide. The test kit includes a container holding the IL-18BP and/or one or more antibodies and instructions for using the IL-18BP and/or the antibodies for the purpose of binding to IL-18 antigen to form an immunological complex and detecting the formation of the immunological complex such that presence or absence of the immunological complex correlates with presence or absence of IL-18 antigen.

In accordance with the above, the invention also provides a pharmaceutical kit comprising the pharmaceutical composition of the invention as disclosed herein in the various embodiments in separate unit dosage forms, said forms being suitable for administration in effective amounts. Such a kit suitably further comprises one or more inhalation devices for administration of the pharmaceutical composition of the invention as disclosed herein in the various embodiments. For example, the kit may comprise one or more dry powder inhalation devices adapted to deliver dry powder from a capsule, together with capsules containing a dry powder comprising a dosage unit of the pharmaceutical composition of the invention as disclosed herein in the various embodiments. In another example, the kit may comprise a multi-dose dry powder inhalation device containing in the reservoir thereof a dry powder comprising a multidose dry powder inhalation device containing in the reservoir thereof a dry powder comprising the pharmaceutical composition of the invention as disclosed herein in the various embodiments.

DEFINITIONS

The technical terms and expressions used within the scope of this application are generally to be given the meaning commonly applied to them in the pertinent art if not otherwise indicated herein below.

As used in this specification and the appended embodiments, the singular forms "a", "an", and "the" include plural referents unless the context clearly dictates otherwise. Thus, for example, reference to "a compound" includes one or more compounds.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effects attributed to the disease. The term "treatment" as used herein covers any treatment of a disease in a subject and includes: (a) preventing a disease, i.e. related to an undesired immune response from occurring in a subject which may be predisposed to the disease; (b) inhibiting the disease, i.e. arresting its development; or (c) relieving the disease, i.e. causing regression of the disease (d) reversing the disease symptoms, i.e. leading to recovery of damaged tissue.

The expression "IL-18 Binding Protein (IL-18BP)" as used herein includes the full-length protein, a mutein, fragment, peptide, functional derivative, functional fragment, fraction, circularly permuted derivative, fused protein, isoform or a salt thereof.

The term "free IL-18" as used herein means monomeric, soluble and non-complexed interleulin-18 protein.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as [kappa] and [lambda] light chains. Heavy chains are classified as [micro], [Delta], [gamma], [alpha], or [epsilon], and define the antibody's isotype as IgM, IgD, IgG, IgA, and IgE, respectively. Within light and heavy chains, the variable and constant regions are joined by a "J" region of about 12 2 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR.2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol, 196:901-917 (1987); Chothia et al. Nature 342:878-883 (1989).

The terms "antibody" or "antibodies" as used herein are art recognized term and are understood to refer to molecules or active fragments of molecules that bind to known antigens, particularly to immunoglobulin molecules and to immunologically active portions of immunoglobulin molecules, i.e. molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

The term "Antibody" refers for the purpose of the present invention to an intact immunoglobulin or to an antigen-binding portion thereof that competes with the intact antibody for specific binding. In particular, "Antibodies" are intended within the scope of the present invention to include monoclonal, polyclonal, chimeric, single chain, bispecific or bi-effective, simianized, human and humanized antibodies.

Examples of Antigen-binding portions include, inter alia, Fab, Fab', F(ab')2, scFv, dAb and Fv fragments, including the products of an Fab immunoglobulin expression library and epitope-binding fragments of any of the antibodies and fragments mentioned above. Further examples of Antigen-binding portions include complementarity determining region (CDR) fragments, diabodies and polypeptides that contain at least a portion of an immunoglobulin that is sufficient to confer specific antigen binding to the polypeptide.

Such active fragments can be derived from an antibody of the present invention by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. ct al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin. In one embodiment, certain amino acids in the framework and constant domains of the heavy and light chains have been mutated so as to avoid or abrogate an immune response in humans. In an alternative embodiment, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

In still another embodiment of the invention, a "humanized antibody" refers to a type of engineered antibody having its CDRs derived from a non-human donor immunoglobulin inserted into the a human antibody "scaffold" being derived from one (or more) human immunoglobulin(s). In addition, framework support residues may be altered to preserve binding affinity. Methods to obtain "humanized antibodies" are well known to those of ordinary skill in the art. (see, e.g., Queen et al., Proc. Natl Acad Sci USA, 86:10029-10032 (1989), Hodgson et al., Bio/Technology, 9:421 (1991)).

A "humanized antibody" may also be obtained by a novel genetic engineering approach that enables production of affinity-matured humanlike polyclonal antibodies in large animals such as, for example, rabbits (see, e.g., U.S. Pat. No. 7,129,084).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody. For the purpose of the present invention, "monoclonal antibody" is also to be understood to comprise antibodies that are produced by a mother clone which has not yet reached full monoclonality.

The term "CDRs" refers to the hypervariable region of an antibody. The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions are based on sequence variability and are the most commonly used (Kabat et al., Sequences of Proteins of Immunological Interest, 5th Ed. Public Health Service, National Institutes of Health, Bethesda, Md. (1991)).

The letters "HC" and "LC" preceding the term "CDR" refer, respectively, to a CDR of a heavy chain and a light chain. Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991).

"Functionally equivalent antibody" is understood within the scope of the present invention to refer to an antibody which substantially shares at least one major functional property with an antibody, for example functional properties herein described including, but not limited to: binding specificity to the free IL-18 protein. The antibodies can be of any class such as IgG, IgM, or IgA, etc or any subclass such as IgG1, IgG2a, etc and other subclasses described herein or known in the art, but particularly of the IgG4 class. Further, the antibodies can be produced by any method, such as phage display, or produced in any organism or cell line, including bacteria, insect, mammal or other type of cell or cell line which produces antibodies with desired characteristics, such as humanized antibodies. Antibodies can also be formed by combining a Fab portion and an Fc region from different species.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164(1991).

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of host cells such as a prokaryotic cell, for example, *E. coli*. In another embodiment, the host cell is a eukaryotic cell, for example, a protist cell, an animal cell, a plant cell, plants or a fungal cell. In an embodiment, the host cell is a mammalian cell including, but not limited to, CHO, COS, NS0, SP2, PER.C6, or a fungal cell, such as *Saccharomyces cerevisiae*, or an insect cell, such as Sf9. In another embodiment, cells producing human antibodies can be grown in bioreactors or for plants in green houses and fields (see, for example, in: Riechmann L, et al (1988). *Nature* 332 (6162): 332-323; Queen C, et al. (December 1989). *Proc Natl Acad Sci USA*. 86 (24): 10029-33; Kashmiri S V, et al. (May 2005). *Methods* 36 (1): 25-34; Hou S, et al (July 2008). *J Biochem* 144 (1): 115-20). in host.

A "patient" or "subject" for the purposes of the present invention is used interchangeably and meant to include both humans and other animals, particularly mammals, and other organisms. Thus, the methods are applicable to both human therapy and veterinary applications. In the preferred embodiment the patient or subject is a mammal, and in the most preferred embodiment the patient or subject is a human.

The expressions "pharmaceutical composition" and "therapeutical composition" are used herein interchangeably in the widest sense. They are meant to refer, for the purposes of the present invention, to a therapeutically effective amount of the active ingredient, i.e. the IL-18BP and, optionally, a pharmaceutically acceptable carrier or diluent.

It embraces compositions that are suitable for the curative treatment, the control, the amelioration, an improvement of the condition or the prevention of a disease or disorder in a human being or a non-human animal. Thus, it embraces pharmaceutical compositions for the use in the area of human or veterinary medicine. Such a "therapeutic composition" is characterized in that it embraces at least one IL-18BP compound or a physiologically acceptable salt thereof, and optionally a carrier or excipient whereby the salt and the carrier and excipient are tolerated by the target organism that is treated therewith.

A "therapeutically effective amount" refers to that amount which provides a therapeutic effect for a given condition and administration regimen. In particular, "therapeutically effective amount" means an amount that is effective to prevent, reverse, alleviate or ameliorate symptoms of the disease or prolong the survival of the subject being treated, which may be a human or non-human animal. Determination of a therapeutically effective amount is within the skill of the person skilled in the art. In particular, in the present case a "therapeutically or prophylactically effective amount" refers to the amount of protein or peptide, mutein, functional derivative, fraction, circularly permuted derivative, fused protein, isoform or a salt thereof, and compound or pharmaceutical composition which, when administered to a human or animal, leads to a therapeutic or prophylactic effect in said human or animal. The effective amount is readily determined by one of skill in the art following routine procedures. The therapeutically effective amount or dosage of a compound according to this invention can vary within wide limits and may be determined in a manner known in the relevant art. The dosage can vary within wide limits and will, of course, have to be adjusted to the individual requirements in each particular case.

The term "transmucosal" administration refers to various administration routes wherein the compound is absorbed by the mucosa of any part of the body. Transmucosal administration comprises, but is not limited to, i.e. intranasal, buccal, oral transmucosal, intratracheal, intraurinary tract, intrarectal, intravaginal, sublingual, intrabronchial, intrapulmonary and transdermal administration.

The definition "pharmaceutically acceptable" is meant to encompass any carrier, excipient, diluent or vehicle, which does not interfere with effectiveness of the biological activity of the active ingredient and that is not toxic to the host to which it is administered.

The term "fused protein" refers to a polypeptide comprising an IL-18BP, or a viral IL-18BP, or a mutein or fragment thereof, fused with another protein, which, e. g., has an extended residence time in body fluids. An IL-18BP or a viral IL-18BP may thus be fused to another protein, polypeptide or the like, e. g., an immunoglobulin or a fragment thereof.

These isoforms, muteins, fused proteins or functional derivatives retain the biological activity of IL-18BP, in particular the binding to IL-18, and preferably have essentially at least an activity similar to IL-18BP. Ideally, such proteins have a biological activity which is even increased in comparison to unmodified IL-18BP. Preferred active fractions have an activity which is better than the activity of IL-18BP, or which have further advantages, like a better stability or a lower toxicity or immunogenicity, or they are easier to produce in large quantities, or easier to purify.

The term "interleukin-18 binding protein" comprises also an IL-18BP mutein, functional derivative, fraction, biologically active peptide, circularly permuted derivative, fused protein, isoform and a salt thereof.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, high throughput mutagenesis, DNA shuffling, protein evolution techniques, or any other known technique suitable therefore.

Any such mutein preferably has a sequence of amino acids sufficiently duplicative of that of an IL-18BP, or sufficiently duplicative of a viral IL-18BP, such as to have substantially similar activity to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e. g. to a simple sandwich competition assay to determine whether or not it binds to an appropriately labeled IL-18, such as radioimmunoassay or ELISA assay.

Muteins of IL-18BP polypeptides or muteins of viral IL-18BPs, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-18BP polypeptides or proteins or viral IL-18BPs, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e. g. under thirty, and preferably under ten, and do not remove or displace amino acids which are critical to a functional conformation, e. g., cysteine residues. Proteins and muteins produced by such deletions and/or insertions come within the purview of the present invention.

"Functional derivatives" as used herein cover derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do-not destroy the activity of the protein which is substantially similar to the activity of IL-18BP, or viral IL-18BPs, and do not confer toxic properties on compositions containing it.

These derivatives may, for example, include polyethylene glycol side-chains, which may mask antigen sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e. g. alkanol or carbocyclic aroyl groups) or O-acyl derivatives of free hydroxyl groups (for example that of seryl or threonyl residues) formed with acyl moieties.

As "functional fragment" of an IL-18BP, or a viral IL-18BP, mutein and fused protein, the present invention covers any fragment or precursors of the polypeptide chain of the IL-18BP protein molecule alone or together with associated molecules or residues linked thereto, e. g., sugar or phosphate residues, or aggregates of the protein molecule or the sugar residues by themselves, provided said fraction has substantially similar activity to IL-18BP.

The term "salts" herein refers to both salts of carboxyl groups and to acid addition salts of amino groups of the IL-18BP molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL-18BP, e. g. the ability to bind IL-18.

"Isoforms" of IL-18BP are proteins capable of binding IL-18 or fragment thereof, which may be produced by alternative splicing.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

The expression "abnormal levels of free IL-18" refers to increased or decreased levels of IL-18 compared to the values detected in body fluids of a healthy control subject. In particular, these abnormal levels mean increased values of IL-18. In particular, said abnormal level of free IL-18 in the body fluids exceeds the level in body fluids of a healthy control subject by 5%, 10%, 20%, 30%, 40%, 50%, 60%, 70%, 80%, 90%, 100%, or more than 100%. In certain embodiments of the invention the reference or control value is the normal, non-pathologic base value for free IL-18 determined in the patient to be treated.

The expression "abnormal ratio of free IL-18/IL-18BP" refers to an increased ratio of IL-18 to IL-18BP compared to values found in body fluids of a healthy control subject. In particular, said abnormal ratio of free IL-18 to IL-18BP in the body fluids exceeds the ratio in body fluids of a healthy control subject by 1%, 2.5%, 5%, 10%, 20%, 30%, 40%, 50%, 60%, 70%, 80%, 90%, 100%, or more than 100%. In certain embodiments of the invention the reference or control value is the normal, non-pathologic base value for free IL-18 determined in the patient to be treated.

The expressions "gene silencing" and "post transcriptional gene silencing" mean the suppressive regulation of gene expression by mechanisms others than genetic modification. The silencing occurs by mRNA neutralization on the post transcriptional level, wherein mRNA translation is prevented to form an active gene product, which is in most cases a protein.

The term "predisposition" means the increased susceptibility of a subject for developing a specific disease. In the present case a subject is classified as predisposed if for instance elevated IL-18 level appear in the lung, serum, sputum, broncho-alveolar lavage fluid (BALF) or circulation.

The expressions "smoke", "smoke-induced", "cigarette smoke" or "cigarette smoke induced" refer to tobacco smoke.

"Alveolar macrophages" are a subtype of macrophages found in the pulmonary alveolus. They often contain granules of exogenous material that they have picked up from the respiratory surfaces. Such black granules are especially common in people, which are long-time exposed to fine dust, fine particles, e.g. like smoker or long-term city dwellers.

A "Th2 cytokine response" mediated by IL-4, IL-5, IL-6, IL-8, IL-10, IL-13, and/or IL-17A, particularly IL-4 and/or IL-8 and/or IL-17A, whereas a "Th1 cytokine response" is mediated by interferon-gamma (IFN-γ), IL-2, and tumor necrosis factor-alpha (TNF-α).

The expression "IL-18/IL-18BP imbalance" relates to the dysregulation of mutual interaction of IL-18 and IL-18BP, which finally leads to an elevated level of unbound IL-18.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a subject, or both, are reduced.

The terms "dysregulated" or "dysregulation," as used herein, refer to an impairment in a biological process which in turn may lead to deleterious physiological sequela, or abnormal expression of a gene, nucleic acid, protein, peptide, or other biological molecule. In the case where expression of a gene, nucleic acid, protein, peptide, or other biological molecule is dysregulated, the gene, nucleic acid, protein, peptide, or other biological molecule is expressed, processed, or maintained at levels that are outside what is considered the normal range for that of that gene, nucleic acid, protein, peptide, or other biological molecule as determined by a skilled artisan. Dysregulation of a gene, nucleic acid, protein, peptide, or other biological molecule in a mammal may be determined by measuring the level of a gene, nucleic acid, protein, peptide, or other biological molecule in the mammal and comparing the level measured in that mammal to level measured in a matched population known not to be experiencing dysregulation of that gene, nucleic acid, protein, peptide, or other biological molecule dysregulated. Alternatively, the level may be compared to one measured in the same individual at a different time.

The terms "heart disease" or "cardiovascular disease" as used herein comprises diseases and disorders that affect the heart muscle or the blood vessels of the heart and the body. Heart diseases may lead to cardiac failure and eventually are one of the most frequent causes of death in industrial societies. Examples for heart diseases induced by IL-18/IL-18BP imbalance comprise, but are not limited to obstructive heart disease, thrombolytic dysfunction, alcoholic cardiomyopathy, aortic valve prolapse, aortic valve stenosis, arrhythmias, cardiogenic shock, congenital heart disease, dilated cardiomyopathy, heart attack, heart failure, heart tumor, heart valve pulmonary stenosis, hypertrophic cardiomyopathy, idiopathic cardiomyopathy, ischemic heart disease, ischemic cardiomyopathy, mitral regurgitation, mitral valve prolapse, peripartum cardiomyopathy, stable angina.

The term "diabetes mellitus type 2" as used herein is the most common form of diabetes. This disease or disorder is characterized that either the body does not or only insufficiently produce the enzyme insulin or cells have defects in their response to insulin. Such defects are believed to involve the insulin receptor.

As used herein "endogenous" refers to any material from or produced inside an organism, cell, tissue or system. The term "exogenous" refers to any material introduced from or produced outside an organism, cell, tissue or system.

The term "expression" as used herein is defined as the transcription and/or translation of a particular nucleotide sequence driven by its promoter. The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well. The expression vector according to the present invention can be used in gene therapy for the treatment of the disease or disorder as disclosed herein. In particular, said expression vector is a viral vector. The viruses that can be used as a vehicle to deliver the expression vector is selected from the group of retrovirus, adenovirus, lentivirus, herpes simplex virus, vaccinia, pox virus, and adeno-associated virus.

The terms "inhibit", "neutralize" or "block" as used herein, have to be understood as synonyms which mean reducing a molecule, a reaction, an interaction, a gene expression, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The term "antisense expression vector" refers to an expression vector, which encodes for single-stranded or double-stranded RNA that is complementary to a messenger RNA (mRNA) strand and which inhibits translation of said mRNA into amino acids. The term antisense RNA comprises asRNA, siRNA, shRNA, microRNA.

The term "gene therapy" as used herein means the use of DNA, e.g. an expression vector, as a pharmaceutical agent to treat a disease as disclosed herein.

BRIEF DESCRIPTION OF THE FIGURES

FIG. 11: shows the amino acid sequences of the variable heavy chain (VH) and the variable light chain (VK) of antibodies produced by different clones (SEQ ID NOs: 81-152). The complementary determining regions CDR 1, CDR 2 and CDR 3 are identified by underlining the respective sequences as determined by the IMGT numbering system (Lefranc, M.-P. et al., Nucleic Acids Research, 27, 209-212 (1999)). From left to right, the first underlined sequence in each of the VH and VK sequences shown represents CDR1, the second underlined sequence represents CDR 2 and the third underlined sequence represents CDR 3. The variable domain is highlighted in BOLD.

SEQUENCES

Figure 1:
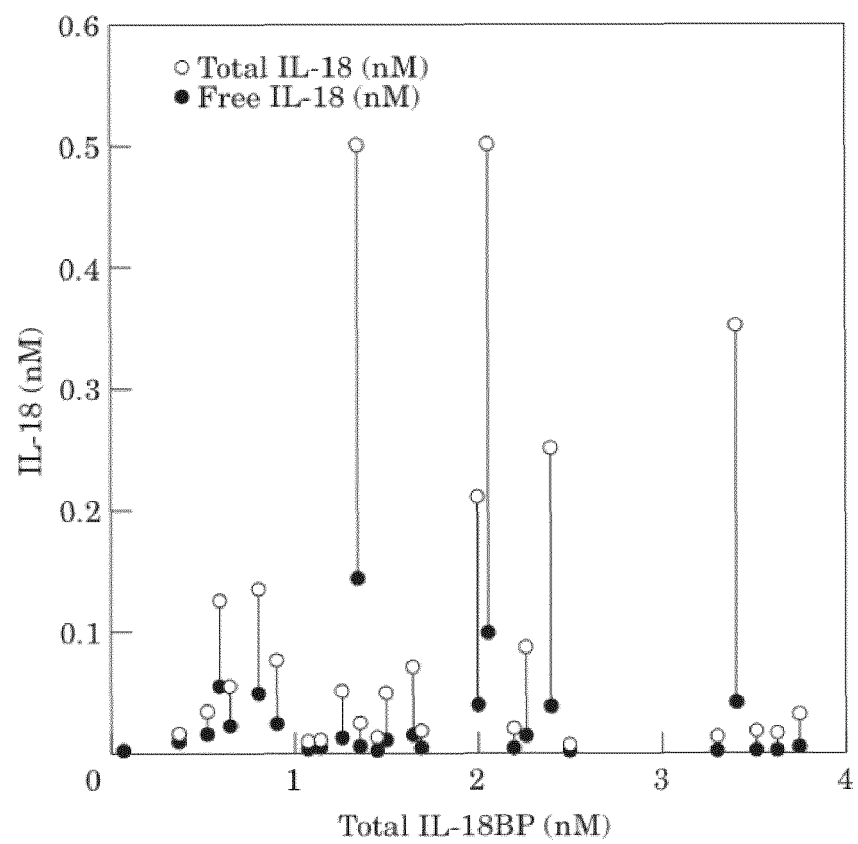
FIG. 1: Comparison of total and free IL-18 in individual sepsis patients. Adapted from Novick et al 2001. The level of free IL-18 (closed circles) in sera of sepsis patients upon admission was calculated based on the concentration of total IL-18 (open circles) and IL-18BPa, taking into account a 1:1 complex of IL-18 and IL-18BPa and a calculated KD of 400 pM. Each vertical line links total and free IL-18 in an individual serum sample. The above ELISA assays are performed with the pair of antibodies developed by Taniguchi et al 1997 1, namely antibodies 125-2H as primary/capture antibody and 159-12B as secondary/developing antibody.

```
SEQ ID NO 1: IL-18 Epitope 1:
Tyr-Phe-Gly-Lys-Leu-Glu-Ser-Lys-Leu-Ser-Val-Ile-
Arg-Asn SEQ ID NO 2: IL-18 Epitope 2:
Phe-Ile-Ile-Ser-Met-Tyr-Lys-Asp-Ser-Gln-Pro-Arg-
Gly-Met-Ala-Val-Thre-Ile-Ser-Val-Lys SEQ ID NO 3: IL-18 Epitope 3:
Glu-Met-Asn-Pro-Pro-Asp-Asn-Ile-Lys-Asp-Thr-Lys-
Ser-Asp-Ile-Ile-Phe
```

-continued

SEQ ID NO 4: IL-18 Epitope 4:
Tyr-Phe-Gly-Lys-Leu-Glu-Ser

SEQ ID NO 5: IL-18 Epitope 5:
Tyr-Lys-Asp-Ser-Gln-Pro-Arg-Gly-Met-Ala

SEQ ID NO 6: IL-18 Epitope 6:
Asp-Asn-Ile-Lys-Asp-Thr-Lys

SEQ ID NO 7: IL-18 Binding Protein (IL-18BP)

SEQ ID NO: 8: 13-amino acid Linker Sequence:
Glu-Phe-Gly-Ala-Gly-Leu-Val-Leu-Gly-Gly-Gln-Phe-Met SEQ ID NO: 9: Antibody 107C6 VH sequence SEQ ID NO: 10: Antibody 107C6 VK sequence SEQ ID NO: 11: Antibody 108F8 VH sequence SEQ ID NO: 12: Antibody 108F8 VK sequence SEQ ID NO: 13: Antibody 109A6 VH sequence SEQ ID NO: 14: Antibody 109A6 VK sequence SEQ ID NO: 15: Antibody 111A6 VH sequence SEQ ID NO: 16: Antibody 111A6 VK sequence 1

SEQ ID NO: 17: Antibody 111A6 VK sequence 2

SEQ ID NO: 18: Antibody 131B4 VH sequence

SEQ ID NO: 19: Antibody 131B4 VK sequence

SEQ ID NO: 20: Antibody 131E8 VH sequence 1

SEQ ID NO: 21: Antibody 131E8 VH sequence 2

SEQ ID NO: 22: Antibody 131E8 VK sequence

SEQ ID NO: 23: Antibody 132H4 VH sequence

SEQ ID NO: 24: Antibody 132H4 VK sequence

SEQ ID NO: 25: Antibody 133A6 VH sequence

SEQ ID NO: 26: Antibody 133A6 VK sequence

SEQ ID NO: 27: Antibody 107C6 VH sequence CDR1:
Gly Tyr Thr Phe Thr Asn Tyr Gly

SEQ ID NO: 28: Antibody 107C6 VH sequence CDR2:
Ile Asn Thr Tyr Ser Gly Val Pro

SEQ ID NO: 29: Antibody 107C6 VH sequence CDR3:
Ala Arg Glu Gly Tyr Ser Thr Thr Arg Ser Met Asp Tyr SEQ ID NO: 30: Antibody 107C6 VK sequence CDR1:
Gln Ser Leu Leu Asp Ser Arg Thr Arg Lys Asn Tyr SEQ ID NO: 31: Antibody 107C6 VK sequence CDR2:
Trp Ala Ser SEQ ID NO: 32: Antibody 107C6 VK sequence CDR3:
Lys Gln Ser Tyr Asn Leu Arg Thr SEQ ID NO: 33: Antibody 108F8 VH sequence CDR1:
Gly Tyr Thr Phe Thr Asn Tyr Gly SEQ ID NO: 34: Antibody 108F8 VH sequence CDR2:
Ile Asn Thr Tyr Ser Gly Val Pro -continued SEQ ID NO: 35: Antibody 108F8 VH sequence CDR3:
Ala Arg Glu Gly Tyr Ser Thr Thr Arg Ser Met Asp Tyr SEQ ID NO: 36: Antibody 108F8 VK sequence CDR1:
Gln Ser Leu Leu Asp Ser Arg Thr Arg Lys Asn Tyr SEQ ID NO: 37: Antibody 108F8 VK sequence CDR2:
Trp Ala Ser SEQ D NO: 38: Antibody 108F8 VK sequence CDR3:
Lys Gln Ser Tyr Asn Leu Arg Thr SEQ ID NO: 39: Antibody 109A6 VH sequence CDR1:
Gly Phe Lys Ile Lys Asp Thr Tyr SEQ ID NO: 40: Antibody 109A6 VH sequence CDR2:
Ile Asp Pro Ala Asn Gly Asn Thr SEQ ID NO: 41: Antibody 109A6 VH sequence CDR3:
Ala Gly Tyr Val Trp Phe Ala Tyr SEQ ID NO: 42: Antibody 109A6 VK sequence CDR1:
Gln Arg Leu Val His Ser Asn Gly Asn Thr Tyr SEQ ID NO: 43:: Antibody 109A6 VK sequence CDR2:
Thr Val Ser SEQ D NO: 44: Antibody 109A6 VK sequence CDR3:
Ser Gln Ser Thr Leu Val Pro Trp Thr SEQ ID NO: 45: Antibody 111A6 VH sequence CDR1:
Gly Phe Lys Ile Lys Asp Thr Tyr SEQ ID NO: 46 Antibody 111A6 VH sequence CDR2:
Ile Asp Pro Ala Asn Gly Asn Thr SEQ ID NO: 47: Antibody 111A6 VH sequence CDR3:
Ala Gly Tyr Val Trp Phe Ala Tyr SEQ ID NO: 48: Antibody 111A6 VK sequence 1 CDR1:
Ser Ser Val Ser Ser Ser Tyr SEQ ID NO: 49: Antibody 111A6 VK sequence 1 CDR2:
Ser Thr Ser SEQ ID NO 50: Antibody 111A6 VK sequence 1 CDR3:
Gln Gln Tyr Ser Gly Tyr Pro Leu Thr SEQ ID NO: 51: Antibody 111A6 VK sequence 2 CDR1:
Gln Arg Leu Val His Ser Asn Gly Asn Thr Tyr SEQ ID NO: 52: Antibody 111A6 VK sequence 2 CDR2:
Thr Val Ser SEQ ID NO: 53: Antibody 111A6 VK sequence 2 CDR2:
Ser Gln Ser Thr Leu Val Pro Trp Thr SEQ ID NO: 54: Antibody 131B4 VH sequence CDR1:
Gly Phe Lys Ile Lys Asp Thr Tyr SEQ ID NO: 55: Antibody 131B4 VH sequence CDR2:
Ile Asp Pro Ala Asn Gly Asn Thr SEQ ID NO: 56: Antibody 131B4 VH sequence CDR3:
Ala Gly Tyr Val Trp Phe Ala Tyr SEQ ID NO: 57: Antibody 131 B4 VK sequence CDR1:
Gln Ser Leu Val His Ser Asn Gly Asn Thr Tyr SEQ ID NO: 58: Antibody 131 B4 VK sequence CDR2:
Lys Val Ser SEQ ID NO: 59: Antibody 131B4 VK sequence CDR3:
Ser Gln Ser Ser Leu Val Pro Trp Thr SEQ ID NO: 60: Antibody 131E8 VH sequence 1 CDR1:
Gly Phe Ser Leu Pro Asn Tyr Gly SEQ ID NO: 61: Antibody 131E8 VH sequence 1 CDR2:
Ile Trp Ser Gly Gly Ser Thr -continued SEQ ID NO: 62: Antibody 131E8 VH sequence 1 CDR3:
Ala Arg Asn Phe Tyr Ser Lys Tyr Asp Tyr Ala Met
Asp Tyr SEQ ID NO: 63: Antibody 131 E8 VH sequence 2 CDR1:
Gly Tyr Thr Phe Thr Ser Tyr Trp SEQ ID NO: 64: Antibody 131E8 VH sequence 2 CDR2:
Ile Asn Pro Asn Ser Gly Ser Thr SEQ ID NO: 65: Antibody 131E8 VH sequence 2 CDR3:
Ala Arg Leu Gly Asp Tyr SEQ ID NO: 66: Antibody 131E8 VK sequence CDR1:
Ser Ser Val Ser Tyr SEQ ID NO: 67: Antibody 131 E8 VK sequence CDR2:
Asp Thr Ser SEQ ID NO: 68: Antibody 131E8 VK sequence CDR3:
Phe Gln Gly Ser Gly Tyr Pro Leu Thr SEQ ID NO: 69: Antibody 132H4 VH sequence CDR1:
Gly Phe Thr Phe Ser Asn Tyr Ala SEQ ID NO: 70: Antibody 132H4 VH sequence CDR2:
Ile Ser Ser Gly Gly Ala Asn Ile SEQ ID NO: 71: Antibody 132H4 VH sequence CDR3:
Ala Arg Gly Asp Tyr Phe Asn His Phe Trp Phe
Ala Tyr SEQ ID NO: 72: Antibody 132H4 VK sequence CDR1:
Gln Ser Ile Val His Ser Asn Gly Asn
Thr Tyr SEQ ID NO: 73: Antibody 132H4 VK sequence CDR2:
Lys Val Ser SEQ ID NO: 74: Antibody 132H4 VK sequence CDR3:
Phe Gln Gly Ser His Val Pro Trp Thr SEQ ID NO: 75: Antibody 133A6 VH sequence CDR1:
Gly Phe Thr Phe Ser Asn Tyr Ala SEQ ID NO: 76: Antibody 133A6 VH sequence CDR2:
Ile Ser Ser Gly Gly Gly Asn Ile SEQ ID NO: 77: Antibody 133A6 VH sequence CDR3:
Ala Arg Gly Asp Tyr Ser Asn Tyr Phe Trp Phe Ala
Tyr SEQ ID NO: 78: Antibody 133A6 VK sequence CDR1:
Gln Ser Ile Val His Ser Asn Gly Asn Thr Tyr SEQ ID NO: 79: Antibody 133A6 VK sequence CDR2:
Lys Val Ser SEQ ID NO: 80: Antibody 133A6 VK sequence CDR3:
Phe Gln Gly Ser His Val Pro Trp Thr

EXAMPLES

A. Detection of Free IL-18 Versus Complex IL-18/IL-18BP

1. Common Detection of IL-18 in Patients

Human IL-18 quantification in patients is performed with ELISA assays detecting total IL-18 (both free form and IL-18BP complex). The ELISA comprises commercially available antibodies (see Table 8 below). Most common ELISA assays are performed with the pair of anti-IL-18 antibodies developed by Taniguchi et al 1997 and sold by different suppliers, namely monoclonal mouse antibody 125-2H as primary/capture antibody and monoclonal rat 159-12B as secondary/developing antibody.

TABLE 8

Scientific publications reporting IL-18 quantifications in human patients

| References | Assay, disease | Antibodies and commercial source |
|---|---|---|
| Wong CK et al 2000 | IL-18 and IL-12 levels in plasma, Systemic Lupus Erythematosus | 1. Human IL-18 ELISA kit from MBL, #7620<br>2. Human IL-12 ELISA kit from R&D Systems, #DP400 |
| Park MC et al 2004 | IL-18 level in serum, Systemic Lupus Erythematosus | Human IL-18 ELISA kit from R&D Systems same as MBL kit #7620 |
| Novick D et al 2001 | IL-18 and IL-18BP in serum, Sepsis | 1. Two human IL-18 antibodies from R&D systems (mouse monoclonal biotinylated as capture # N/A and rabbit polyclonal ruthenylated as detection #N/A)<br>2. Two IL-18BP antibodies developed by Interpharm and Serono that are not commercially available, clone MAb No. 582.10 as capture antibody (see above, paragraph 2.2. IL-18BP detection in human serum and urine) and rabbit polyclonal antibody for detection |
| Novick D et al 2010 | IL-18 and IL-18BP levels in serum, Systemic Lupus Erythematosus | Same as Novick et al 2001, see previous row |
| Chen DY et al 2004 | IL-18 levels in serum, Adult Still's Disease | Human IL-18 ELISA kit from Bender MedSystems (now eBioscience) comprising 2 human IL-18 antibodies called BMS267/2MST:<br>1. Monoclonal capture antibody # N/A<br>2. Monoclonal detection antibody labeled with biotin # N/A and reaction revealed with streptavidin-HRP |

2. Estimations of Free IL-18 Levels

To date, there are no reports of measured levels of free IL-18. Estimations of free IL-18 are made by extrapolation using the calculation described by Novick et al 2004 (see below). The data compares levels of IL-18 and IL-18BP in human. In these studies, researchers used the pair of commercial monoclonal anti-IL-18 antibodies 125-2H and 159-12B, where antibody 125-2H is used for capture and is known to bind the IL-18/IL-18BP complex (Argiradi et al 2009). To calculate free IL-18 in patient sera, they applied the Law of Mass Action assuming that the binding of IL-18 antibodies is reversible. The calculation is performed as follow:

$$K_D = 0.4 \text{ nM} = ([IL\text{-}18] \times [IL\text{-}18BP])/[IL\text{-}18\text{-}IL\text{-}18\text{-}IL\text{-}BP]$$

or $$[IL\text{-}18] \text{ in nM} = (0.4 \times [IL\text{-}18\text{-}IL\text{-}18\text{-}IL\text{-}BP])/[IL\text{-}18BP]$$

Where:
IL-18-IL-18BP is a complex
Dissociation constant as calculated by Kim et al 2000, $K_D = 0.4$ nM Stoichiometry 1:1 in the complex IL-18-IL-18BP
Concentration of IL-18 is determined by electro-chemiluminescence
Concentration of IL-18BP is determined by ELISA It is important to note that the authors find large variations of free IL-18 versus the total IL-18 between patients that do not reflect the ratio of IL-18 versus IL-18BP. Interestingly, this IL18/IL-18BP ratio is not reported in the cited publications. Furthermore, anti-IL18 antibodies are not able to distinguish between free IL-18 and the complex form IL-18/IL-18BP. Finally, as described by Novick et al 2001, the anti-IL-18BP antibodies do not detect IL-18BP free form but total IL-18BP since they were reported not to block the interaction between IL-18BP and IL-18, respectively monoclonal antibodies 582.10 and 657.27. Consequently, the calculation of free IL-18 using the concentration of IL-18BP lacks accuracy. Even though encouraging, the data variation indicates that free IL-18 detection could be improved with a more appropriate assay combining antibodies specifically targeting the region of IL-18 that binds to IL-18BP.

3. Confirmation that Commonly Used Commercially Antibodies do not Detect Free IL-18

Eleven commercially available anti-IL-18 monoclonal antibodies were tested for their ability to prevent any IL-18 interaction with IL-18BP. The below data demonstrates that this is not the case and that none of the antibodies tested bind to the site of interaction between IL-18 and IL-18BP. Consequently, the detection of free IL-18 in human samples requires specific design and approaches targeting for example the IL-18 binding site/epitope to IL-18BP.

Figure 2:
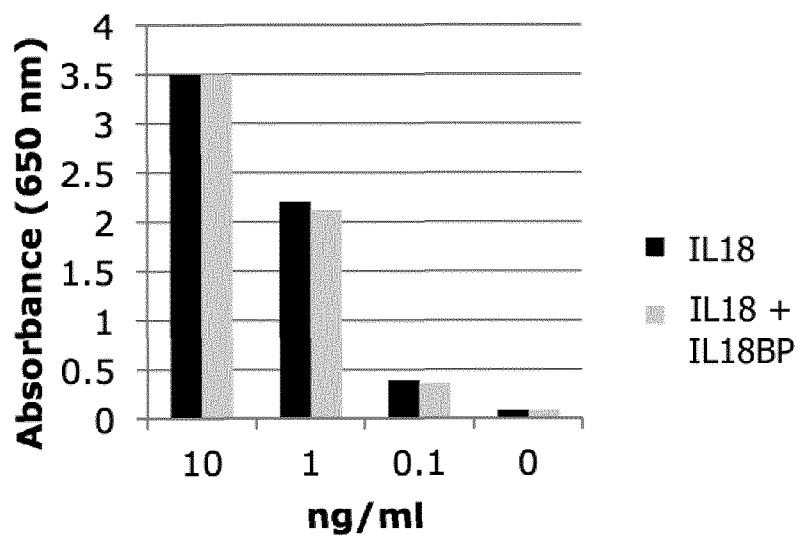
FIG. 2: Detection of total IL-18 with antibodies 125-2H and 159-12B. The data indicates that both antibodies quantify total IL-18.
Figure 2:
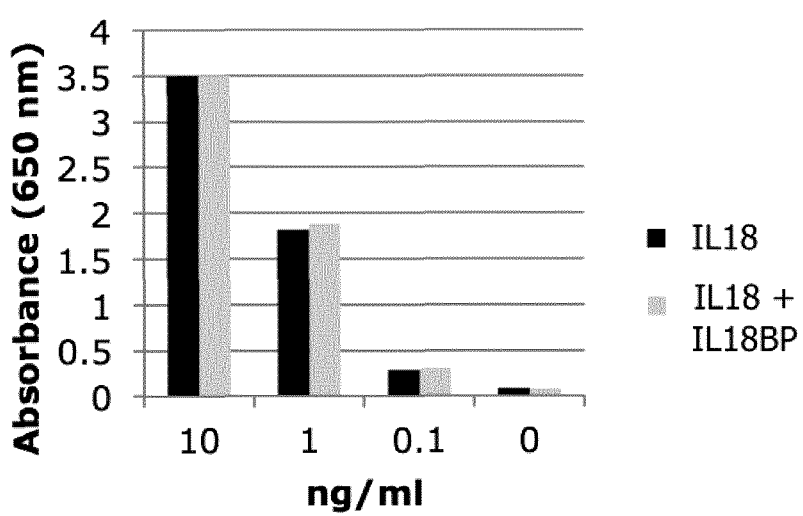
Figure 3:
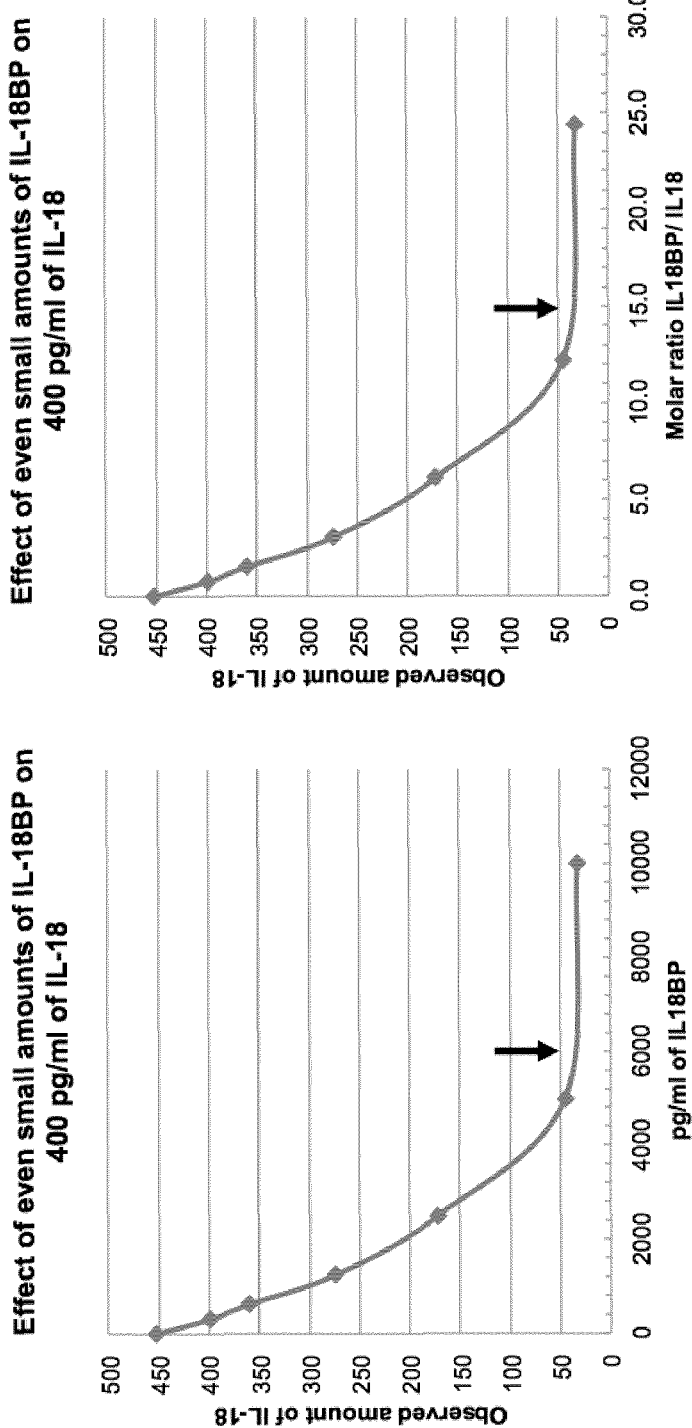
FIG. 3: Titration of 400 pg/ml IL-18 as a function of IL-18BP level
Figure 4:
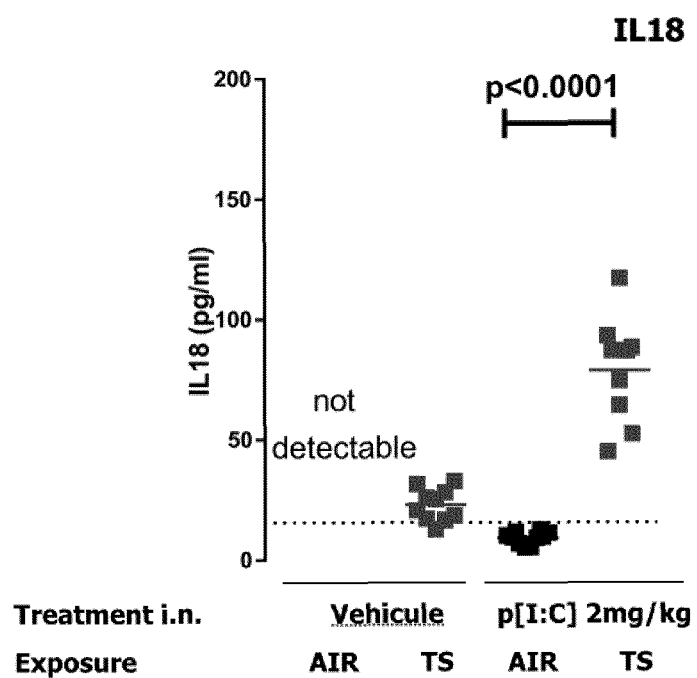
FIG. 4: Mouse IL-18 induction in the lung airway space at day 5 after 1) air exposure, 2) tobacco smoke (TS), 3) p[I:C] alone, 4) p[I:C] combined to tobacco smoke at day 4 (induction of exacerbation). Dotted line indicates lower limit of detection. Statistical analyses were performed using either the unpaired t-test.

The commonly used 125-2H and 159-12B antibodies were tested for both as capture and developing antibodies (see FIG. 2). The data indicates that both antibodies do not recognize the IL-18 epitope for IL-18BP and consequently provide only a quantification of total IL-18 (both forms free and complex to IL-18BP).

In parallel to antibodies 125-2H and 159-12G, nine other commercial monoclonal antibodies were tested for their potential to detect free IL-18 in the same conditions as above. As described above, such antibody will be valuable to detect free IL-18 in biological samples. The list of tested commercial antibodies is given in the table 9 below.

TABLE 9

Tested monoclonal anti-IL-18 antibodies

| Company | Antibody name |
| --- | --- |
| MBL International | D043-3, clone 25-2G |
|  | D-045-6 159-12B biotin |
| Santa Cruz | sc-13602 (1.51E3E1) |
| Biotechnologies | sc-133127 (E-8) |
| Abnova | MAB 1308, clone mxsghk-18 |
|  | MAB8223, clone SB116c1 |
|  | MAB8224, cone SB116b1 |
|  | MAB9935, clone 2 |
| Millipore | 04-1503 Anti-Interleukin 18 (clone CPTC-IL18-1) |
| Lifespan | LS-C137620 (clone 50008-2) |

The collected data indicates that none of the commercially available antibodies was able to distinguish the free IL-18 from its complex with IL-18BP.

4. ELISA Set Up to Detect Free IL-18

4.1. Capture of Free IL-18 with IL-18BP

Microplate wells are coated with an appropriate volume phosphate buffer saline solution containing recombinant human IL-18BP. Plates are incubated for a period of time at 4° C. and then stabilized with a blocking buffer containing bovine serum albumin or other appropriate blocking agents. Once the reaction is finished, microplates are sealed and stored at 4° C. until used for detection of free IL-18. Microplates can also be dried in a stabilizing solution allowing storage at room temperature and then be reconstituted by hydration when needed for assay.

As an example, for a final reaction volume of 100 µl, dispense first 80 µl of biotin/antibody conjugate. Samples or biological fluids containing free IL-18 are tested with the IL-18BP coated microplates. After that, 20 µl sample volume containing biological fluid or standard is dispensed per microplate well. Non-diluted or diluted biological fluid can be but is not restricted to serum, urine, tear, saliva, bile, sweat, exhalation or expiration, sputum, bronchoalveolar fluid, sebum, cellular, gland, mucosa or tissue secretion, biopsy, homogenized tissue. The free IL-18 standard concentrations range between 4.2 pg/ml to 3000 pg/ml. Standard and concentrations were prepared from commercially available recombinant human IL-18. The plates are sealed and then incubated under gentle shaking for free IL-18 capture. A suitable period of time is allowed for the reaction ranging from minutes to hours at room temperature, 37° C. or other temperatures that do not affect the stability of the samples and reagents. The microplate wells are the washed extensively with the appropriate buffer and then, 100 µl buffer developing mixture is added to each well. The developing mixture contains a streptavidin-conjugated enzyme such as peroxidase or alkaline phosphatase. The microplate wells are sealed and the reaction is allowed for a period of time at A suitable period of time ranging from minutes to hours at room temperature, 37° C. or other temperatures that do not affect the stability of the samples and reagents. The resulting reactions are then monitored with a microplate reader at an appropriate nanometer wavelength for absorbance or fluorescence of the produced reagent.

4.2. Capture of Free IL-18 with Anti-IL-18 Antibody

Microplate wells are coated with an appropriate volume phosphate buffer saline solution containing Antibody X. Plates are incubated for a period of time at 4° C. and then stabilized with a blocking buffer containing bovine serum albumin or other appropriate blocking agents. Once the reaction is finished, microplates are sealed and stored at 4° C. until used for detection of free IL-18. Microplates can also be dried in a stabilizing solution allowing storage at room temperature and then be reconstituted by hydration when needed for assay.

As an example, for a final reaction volume of 100 µl, dispense first 80 µl of biotin/antibody conjugate. Samples or biological fluids containing free IL-18 are tested with the IL-18BP coated microplates. After that, 20 µl sample volume containing biological fluid or standard is dispensed per microplate well. Non-diluted or diluted biological fluid can be but is not restricted to serum, urine, tear, saliva, bile, sweat, exhalation or expiration, sputum, bronchoalveolar fluid, sebum, cellular, gland, mucosa or tissue secretion, biopsy, homogenized tissue. The free IL-18 standard concentrations range between 4.2 pg/ml to 3000 pg/ml. Standard and concentrations were prepared from commercially available recombinant human IL-18. The plates are sealed and then incubated under gentle shaking for free IL-18 capture. A suitable period of time is allowed for the reaction ranging from minutes to hours at room temperature, 37° C. or other temperatures that do not affect the stability of the samples and reagents. The microplate wells are the washed extensively with the appropriate buffer and then, 100 µl buffer developing mixture is added to each well. The developing mixture contains a streptavidin-conjugated enzyme such as peroxidase or alkaline phosphatase. The microplate wells are sealed and the reaction is allowed for a period of time at A suitable period of time ranging from minutes to hours at room temperature, 37° C. or other temperatures that do not affect the stability of the samples and reagents. The resulting reactions are then monitored with a microplate reader at an appropriate nanometer wavelength for absorbance or fluorescence.

4.3. Titration of Free IL-18 as a Function of IL-18BP Level

A constant quantity of recombinant IL-18 was titrated as a function of different and well defined quantities of IL-18BP in order to understand when free IL-18 is not any more detectable. A PBS solution of 400 pg/mL IL-18 supplemented by 5% BSA was spiked with defined quantities of IL-18BP ranging from 0 to 10'000 pg/mL. The molar ratios were calculated according to the respective molecular weight of IL-18 and IL-18BP. The free IL-18 detection was performed with ELISA using IL-18BP for IL-18 as described above. The collected data presented in FIG. 1 indicates that 400 pg/mL IL-18 detection are near background detection level when IL-18BP concentration is equal or higher to 6000 pg/mL representing a molar ratio IL-18BP/IL-18 of ~15 fold higher IL-18BP. In contrast, when molar ratio is lower than 15, free IL-18 is easily detectable.

4.4. Revised Calculation of Dissociation Constant ($K_D$) Between Human IL-18 and IL-18BP 4.4.1 $K_D$ Calculation by Titration A $K_D$ of 400 pM is reported in the literature based on BIAcore measurements (Kim et al 2000[8]). However, due to the above results, the $K_D$ was revisited with the above ELISA set up. Titration of 10 pM IL-18 was performed with increasing concentrations of IL-18BP (60 pM-3 nM) in either a) healthy volunteer sera depleted in endogenous IL-18BP or b) PBS supplemented by 5% BSA. The free IL-18 ELISA in addition to commercially available assays for total IL-18 and total IL-18BP allows the determination of $K_D$ in solution which should reflect better the affinity of IL-18 to its binding protein in body fluids than data from solid-phase BIAcore method. Example of results are exposed in Table 10.

TABLE 10

Titration of IL-18 in serum or 5% BSA solution containing 1.87 nM IL-18BP

| Standard curve | | Final IL18 spiked ng/mL | IL-18 spiked into serum OD450 nm | IL-18 spiked into 5% BSA OD450 nm | | |
|---|---|---|---|---|---|---|
| pg/mL IL-18 | OD450 nm | | | | nM IL-18 | nM IL-18BP |
| 2000 | 2.894 | 24 | 0.474 | 1.151 | 1.3953 | 1.87 |
| 666.7 | 2.292 | 20 | 0.342 | 0.897 | 1.1628 | 1.87 |
| 222.2 | 0.875 | 16 | 0.286 | 0.735 | 0.9302 | 1.87 |
| 74.1 | 0.303 | 12 | 0.200 | 0.511 | 0.6977 | 1.87 |
| 24.7 | 0.114 | 8 | 0.157 | 0.348 | 0.4651 | 1.87 |
| 8.2 | 0.061 | 4 | 0.091 | 0.188 | 0.2326 | 1.87 |
| 2.7 | 0.042 | 2 | 0.065 | 0.155 | 0.1163 | 1.87 |
| 0 | 0.039 | 0 | 0.040 | 0.037 | 0 | 1.87 |

$K_D$ was calculated based on the following formula:

$K_D$=[free IL-18]×[free IL-18BP]/[IL-18/IL-18BP complex]

[free IL-18BP]=[total IL-18BP]−[free IL-18]

[IL-18/IL-18BP complex]=[total IL-18]−[free IL-18]

Result:

$K_D$=50 pM (Serum diluent); 35 pM (5% BSA diluent)

The titration result indicates a $K_D$ of respectively 50 pM in serum diluent and 35 pM in PBS supplemented by 5% BSA. In contrast to the previous estimations of the $K_D$ between human IL-18BP and IL-18, the newly calculated $K_D$ indicates that previous estimations of free IL-18 based on the $K_D$ of 400 pM reported by Kim et al 2000 are not accurate.

4.4.2 $K_D$ Estimation by BIAcore

Following the above $K_D$ results obtain by titration, we tested the binding affinity of IL-18BP to IL-18 with a simpler BIAcore setup consisting of binding IL-18BP to the BIAcore chip and then testing its affinity to IL-18. The method setup is the contrary of Kim et al 2000[8], who bound IL-18 to the BIAcore chip with a monoclonal antibody and then tested the affinity of the complex antibody-IL-18 to IL-18BP. Importantly, the new BIAcore setup collected data that are aligned completely to the above titration findings, i.e. a $K_D$ ranging between 20 and 30 pM. The data is presented in Table 11 below.

TABLE 11

New BIAcore estimation of human IL-18BP affinity to human IL-18

| $K_a$ ($10^{+5}$/Ms) | $K_d$ ($10^{-6}$ 1/s) | $K_D$ ($10^{-11}$ M) |
|---|---|---|
| 5.3 ± 1.2 | 13.3 ± 2.7 | 25.9 ± 4.8 |

4.5. Titration of Spiked IL-18 in Serum or 5% BSA Solution Containing IL-18BP

Human serum contains significant levels of endogenous as well as complexed IL-18 to IL-18BP, respectively at ng/mL and pg/mL levels. Both are detectable with commercially available antibodies. However, no commercially available assays are available to detect free IL-18. In order to verify the above ELISA setup for the detection of free IL-18, we spiked recombinant human IL-18 in human serum to find levels of detection. For this, nanograms of IL-18 were spiked in either serum containing endogenous 35 ng/mL IL-18BP or PBS solution supplemented by 5% BSA and 35 ng/mL IL-18BP. Resulting free IL-18 was monitored with the ELISA procedure described above. Results are presented in Table 12 below.

TABLE 12

Spiked IL-18 detection in serum or 5% BSA containing 35 ng/ml IL-18BP

| Standard curve | | IL-18 Titration | | |
|---|---|---|---|---|
| pg/mL IL-18 | OD450 nm | Final IL18 spiked ng/mL | IL-18 spiked into serum OD450 nm | IL-18 spiked into 5% BSA OD450 nm |
| 2000 | 3.171 | 100 | 3.5 | 3.5 |
| 666.7 | 1.388 | 80 | 3.5 | 3.5 |
| 222.2 | 0.477 | 70 | 2.37 | 3.5 |
| 74.1 | 0.183 | 60 | 0.99 | 3.37 |
| 24.7 | 0.085 | 50 | 0.68 | 2.05 |
| 8.2 | 0.050 | 40 | 0.46 | 1.17 |
| 2.7 | 0.043 | 30 | 0.298 | 0.75 |
| 0 | 0.043 | 20 | 0.185 | 0.44 |
| | | 10 | 0.11 | 0.16 |
| | | 5 | 0.06 | 0.09 |
| | | 2 | 0.05 | 0.07 |
| | | 0 | 0.04 | 0.04 |

5. Detection of Free IL-18 in Patients 5.1. Detection of Free IL-18 in Serum and Synovial Fluid from Patients Suffering from Different Inflammatory Diseases Samples coming from patients suffering of different inflammatory diseases were tested with the ELISA described above. For this, we selected different disease and stress conditions reported with higher levels of IL-18 such as rheumatoid arthritis, psoriasis, systemic lupus erythematosus and intensive care unit. To our knowledge, no free IL-18 has been identified in those patients, only by calculation with the Law of Mass Action and the $K_D$ of 400 pM reported by Kim et al 2000. According to the above data, it was expected that possible levels of free IL-18 will be difficult to detect due to the total IL-18 levels ranging in serum below or close to 1000 pg/mL as reported in scientific publications. Furthermore, we tested samples from healthy age-matched controls to verify the performance of our ELISA setup. As expected and contrary to the reported Law of Mass Action estimations, the levels of free IL-18 were not detectable neither in serum nor synovial fluid whereas total IL-18 and IL-18BP were (see Table 13).

TABLE 13

Detection of free IL-18 in patients from intensive care unit, with psoriasis, lupus and rheumatoid arthritis

| Patient # | Patient condition/ disease | Biological fluid | Total IL18 pg/ml | Free IL18 pg/ml | Calculated free IL-18 pg/ml $K_D = 4 \times 10^{-10}$M | IL-18BP ng/ml |
|---|---|---|---|---|---|---|
| 1 | Healthy | Serum | 209.7 | — | 40.4 | 29.7 |
| 2 | Healthy | Serum | 125.5 | — | 24.7 | 28.9 |
| 3 | Healthy | Serum | 189.7 | — | 28.2 | 40.6 |
| 4 | Healthy | Serum | 284.7 | — | 65.9 | 23.6 |
| 5 | Healthy | Serum | 227.2 | — | 55.5 | 22.0 |
| 6 | Healthy | Serum | 319.7 | — | 56.4 | 33.2 |
| 7 | Healthy | Serum | 145.5 | — | 26.4 | 32.0 |
| 8 | Healthy | Serum | 206.3 | — | 59.4 | 17.6 |
| 9 | Healthy | Serum | 323.0 | — | 56.5 | 33.5 |
| 10 | Healthy | Serum | 208.0 | — | 49.6 | 22.7 |
| 11 | Intensive care** | Serum | 1158.8 | — | 52 | 151.3 |
| 12 | Intensive care** | Serum | 3769.0 | — | 170.9 | 151.9 |
| 13 | Intensive care** | Serum | 623.8 | — | 27.9 | 151.3 |
| 14 | Intensive care** | Serum | 1978.8 | — | 104.7 | 128.0 |
| 15 | Intensive care | Serum | 611.3 | — | 66.9 | 57.9 |
| 16 | Intensive care | Serum | 434.7 | — | 34.3 | 82.7 |
| 17 | Psoriasis arthritis serum | Serum | 713.8 | — | 70.6 | 64.9 |
| 17 | Psoriasis arthritis synovial fluid | Synovial fluid | 533.0 | — | 78.1 | 41.5 |
| 18 | Lupus serum | Serum | 510.5 | — | 123.4 | 22.5 |
| 18 | Lupus synovial fluid | Synovial fluid | 820.5 | — | 158.9 | 30.0 |
| 19 | Lupus serum | Serum | 503.8 | — | 66.4 | 46.9 |
| 19 | Lupus synovial fluid | Synovial fluid | 236.3 | — | 24.9 | 60.1 |
| 20 | Rheumatoid arthritis | Plasma | 416.3 | — | 39.9 | 66.8 |
| 21 | Rheumatoid arthritis | Serum | 281.3 | — | 67.5 | 22.6 |
| 22 | Rheumatoid arthritis | Serum | 490.5 | — | 42.7 | 74.4 |
| 23 | Rheumatoid arthritis | Serum | 337.2 | — | 52.2 | 38.8 |
| 24 | Rheumatoid arthritis | Serum | 342.2 | — | 53.5 | 38.3 |
| 25 | Rheumatoid arthritis | Serum | 677.2 | — | 90.6 | 46.2 |
| 26 | Rheumatoid arthritis | Serum | 238.8 | — | 41 | 34.2 |
| 27 | Rheumatoid arthritis | Serum | 183.8 | — | 41 | 24.7 |
| 28 | Rheumatoid arthritis | Serum | 385.5 | — | 41.6 | 58.6 |
| 29 | Rheumatoid arthritis | Serum | 345.5 | — | 42.5 | 50.6 |

— not detectable, levels comparable to the background signal
**High IL-18BP levels not within standard curve 5.2. Detection of Free IL-18 in Serum from Patients Suffering from Adult Onset Still's Disease Following the results and in contrast to the above indications having reasonably low levels of total IL-18, we tested Adult onset Still's Disease patient samples which is known for its elevated levels of total IL-18 in serum (Kawashima et al 2001 and Chen et al 2004). As described by Kawashima et al 2001 and elsewhere, elevated total IL-18 serum levels correlate with Adult onset Still's Disease activity such as a) pyrexia, arthralgia, arthritis, cartilage damage, b) higher levels of Ferritin and c) liver enzymes (LDH). Thanks to the above ELISA set up, we report for the first time free IL-18 levels in Adult onset Still's Disease patients (see Table 14). As for the other tested indications, calculated free IL-18 levels do not correspond to the detected free IL-18 levels. The collected data indicates at least 70% of patients were positive to free IL-18.

The proposed approach to quantify free IL-18 by targeting IL-18 binding site to IL-18BP seems more appropriate and is demonstrated for the first time to be more accurate than extrapolated quantifications with the Law of Mass Action. In addition, the affinity of IL-18BP is higher than reported by Kim et al 2000 with a $K_D$ ranging near 50 pM in serum and 20-30 pM with a new BIAcore setup.

Finally, patients suffering of Adult onset Still's Disease were diagnosed as positive to free IL-18 for the first time with the ELISA approach and a set up is presented in the present invention. The data support earlier findings on total IL-18 for Adult onset Still's Disease as reported by Kawashima et al 2001 and Chen et al 2004 reporting high levels of total IL-18. For the first time, the new ELISA approach presented in this application demonstrates presence of free, not complexed and biologically active pro-inflammatory IL-18 in Adult onset Still's Disease patients.

TABLE 14

Detection of free IL-18 in ASD patient serum and synovial fluid

| Patient number | Sample collection date | Biological fluid | Total IL-18 pg/ml | Free IL-18 pg/ml | Calculated Free IL-18 pg/ml $K_D = 4 \times 10^{-10}$M | IL-18BP ng/ml |
|---|---|---|---|---|---|---|
| 1 |  | Serum | 6699 | 9.6 | 1366.5 | 32.6 |
| 1 |  | Synovial fluid | 439 | 15.8 | 439 | — |
| 2 |  | Serum | 713 | 22.5 | 564.3 | 2.0 |
| 3 |  | Serum | 106026 | 3.2* | 59030 | 50.4 |
| 4 |  | Serum | 225456 | 24.9 | 157207 | 68.1 |
| 5 |  | Serum | 175589 | 23.6 | 139614 | 36.1 |
| 6 |  | Serum | 35045 | 2.5* | 8908 | 45.6 |
| 7 |  | Serum | 17714 | 22.4 | 634.8 | 206.0 |
| 7 |  | Synovial fluid | 133325 | 21.3 | 11162 | 193.6 |
| 8 |  | Serum | 25020 | 21.1 | 1277.4 | 153.7 |
| 9 |  | Serum | 3625 | 24.9 | 394.7 | 60.8 |
| 10 | Feb. 17, 2006 | Serum | 11401 | 7.7 | 6062 | 11.3 |
| 10 | Jun. 11, 2007 | Serum | 79942 | 31.6 | 62035 | 19.1 |
| 10 | Apr. 6, 2009 | Serum | 37372 | 18.9 | 22252 | 19.2 |
| 10 | Aug. 6, 2010 | Serum | 185157 | 12.1 | 10566 | 282.9 |
| 10 | Jun. 6, 2012 | Serum | 131561 | 11.2 | 4091 | 341.2 |
| 11 | Jan. 3, 2006 | Serum | 150669 | 34.3 | 114012 | 37.2 |
| 11 | Apr. 4, 2007 | Serum | 106026 | 26.2 | 63543 | 45.2 |
| 11 | Oct. 20, 2008 | Serum | 225456 | 23.6 | 70633 | 163.0 |
| 11 | Apr. 21, 2010 | Serum | 175589 | 23.3 | 116583 | 59.8 |
| 12 | Jun. 2, 2009 | Serum | 3625 | 8.0 | 1633 | 10.5 |
| 13 | Mar. 10, 2010 | Serum | 439 | 4.8** | 151.2 | 13.7 |
| 14 | Jul. 17, 2009 | Serum | 133325 | 19.3 | 21118 | 144.4 |
| 15 | Jul. 24, 2006 | Serum | 35045 | 14.3 | 14628 | 29.3 |
| 16 | Apr. 25, 2007 | Serum | 17714 | 8.0 | 4075 | 36.6 |
| 16 | Jun. 10, 2010 | Serum | 25020 | 6.4 | 2592 | 82.4 |

*Level comparable to the background signal
**Level comparable to the lower limit of detection
— not detectable, level comparable to the background signal 6. Conclusions The data in both publications and the above experimental setup demonstrate that commercial monoclonal antibodies detect total IL-18 but not free IL-18. Furthermore, the most commonly used antibodies to quantify IL-18, namely 125-2H and 159-12B, are confirmed as well in detecting total IL-18.

The estimation of free IL-18 using the Law of Mass Action is an interesting approach. Nevertheless, the large error bars obtained do not support its use in clinical monitoring. Furthermore, the anti-IL-18BP antibodies detect total IL-18BP and not the free form. Consequently, the calculation of free IL-18 using the concentration of IL-18BP lacks accuracy.

B. IL-18BP Efficacy in COPD Exacerbation Mouse Model

The aim of the study was to determine the effect of IL-18BP, administered at three dose levels, by the subcutaneous route, on Polyinosinic:polycytidylic acid-induced exacerbation of tobacco-smoke induced pulmonary inflammation, in C57BL/6J mice. High level of dexamethasone, dosed orally, was included in the study as a reference agent.

1. General Methodology: Four-Day Exacerbation/Tobacco Smoke Mouse Model

Mice received either vehicle (PBS) or IL-18BP. IL-18BP was given subcutaneously to 3 groups of animals respectively at 1, 3 or 10 mg/kg 2 h prior to the initial tobacco smoke exposure from Day 1 to Day 4. Mice received orally either vehicle or dexamethasone (10 mg/kg) 1 h prior to each twice daily exposure. Mice received by intranasal administration either the vehicle or Polyinosinic:polycytidylic acid (2 mg/kg) 2 h prior to the initial air or tobacco smoke exposure on Day 4 to induce lung inflammation exacerbation. Tobacco smoke exposure was performed during the morning and afternoon as follow: Day 1 for 15 min, Day 2 for 25 min, Day 3 for 30 min and Day 4 for 30 min.

Animal groups and their respective treatment regimes are summarized in Table 1.

TABLE 15

Treatment regimes for tobacco smoke mouse model

| Exposure | Treatment s.c./oral | Treatment Code | n | Dose mg/kg | Challenge | Frequency |
|---|---|---|---|---|---|---|
| Air | Veh/Veh | A | 10 | —/— | Veh | Sub-cutaneous |
| TS | Veh/Veh | B | 10 | —/— | Veh | |
| Air | Veh/Veh | C | 10 | —/— | p[I:C] 2 mg/kg | 2 h prior to initial TS |
| TS | Veh/Veh | D | 10 | —/— | p[I:C] 2 mg/kg | on each day |
| TS | IL-18BP/Veh | E | 10 | 1/— | p[I:C] 2 mg/kg | Oral 1 h prior to each TS exposure on each day |
| TS | IL-18BP/Veh | F | 10 | 3/— | p[I:C] 2 mg/kg | |
| TS | IL-18BP/Veh | G | 10 | 10/— | p[I:C] 2 mg/kg | |
| TS | Veh/Dex | H | 10 | —/10 | p[I:C] 2 mg/kg | p[I:C] intranasal 2 h prior to TS exposure on day 4 |

TS: Tobacco smoke;
Veh: Vehicule;
Dex: Dexamethazone,
p[I:C]: Polyinosinic:polycytidylic acid Following the above treatments, animals were terminally anaesthetised on Day 5. After that, a blood sample was taken via the sub-clavian artery (plasma) and the animals were bronchoalveloar lavaged with 3×0.4 ml of PBS for further cellular and cytokine/mediator analysis. Bronchoalveolar lavage supernatants were stored at −80° C. for cytokine/mediator analysis. Cells recovered from the BALF were counted using the Sysmex cell counter. Finally, the collected data was statistically analyzed by Students t-test and ANOVA (Sidak's was used in the case of data passed normality test or Kruskal Wallis test if data did not pass normality test).

Figure 5:
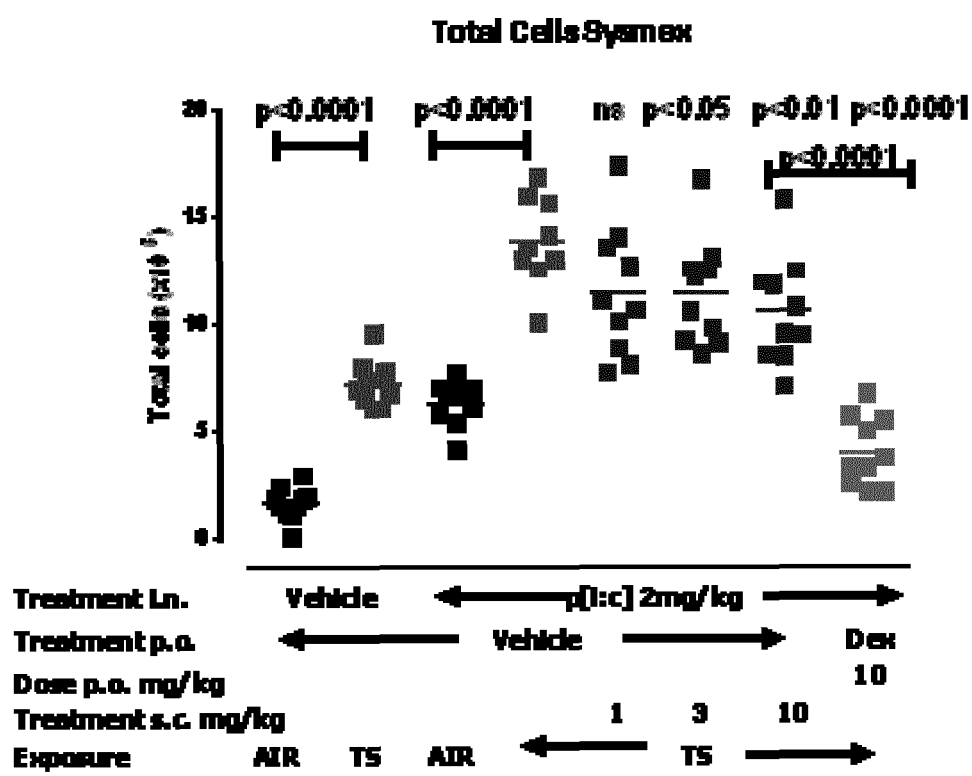
FIG. 5: Inhibition of total cell infiltration in the mouse lung airway space at day 5 after 1) air exposure, 2) tobacco smoke (TS), 3) p[I:C] alone, 4) p[I:C] combined to tobacco smoke at day 4 (induction of exacerbation), 5-7) p[I:C] combined to tobacco smoke at day 4 under IL-18BP treatment at either 1, 3 or 10 mg/kg, 8) dexamethasone treatment at 10 mg/kg. Statistical analyses were performed using either the unpaired t-test.

2. Confirmation of IL-18 Pathway Activation in the Four-Day Exacerbation/Tobacco Smoke Mouse Model Mouse IL-18 was tested in the BAL using a commercial ELISA in order to confirm the mouse model for IL-18 pathway activation. The collected data indicates a clear induction of IL-18 in the lung airway space (see FIG. 5). IL-18 is not detectable in the control (air only). Interestingly, IL-18 is expressed under smoke exposure but is not significantly induced under poly[I:C] alone (under the lower limit of detection). In contrast and as expected, the combination of smoke and poly[I:C] raises considerably IL-18 to much higher levels in the BAL than smoke or poly[I:C] alone.

Figure 6:
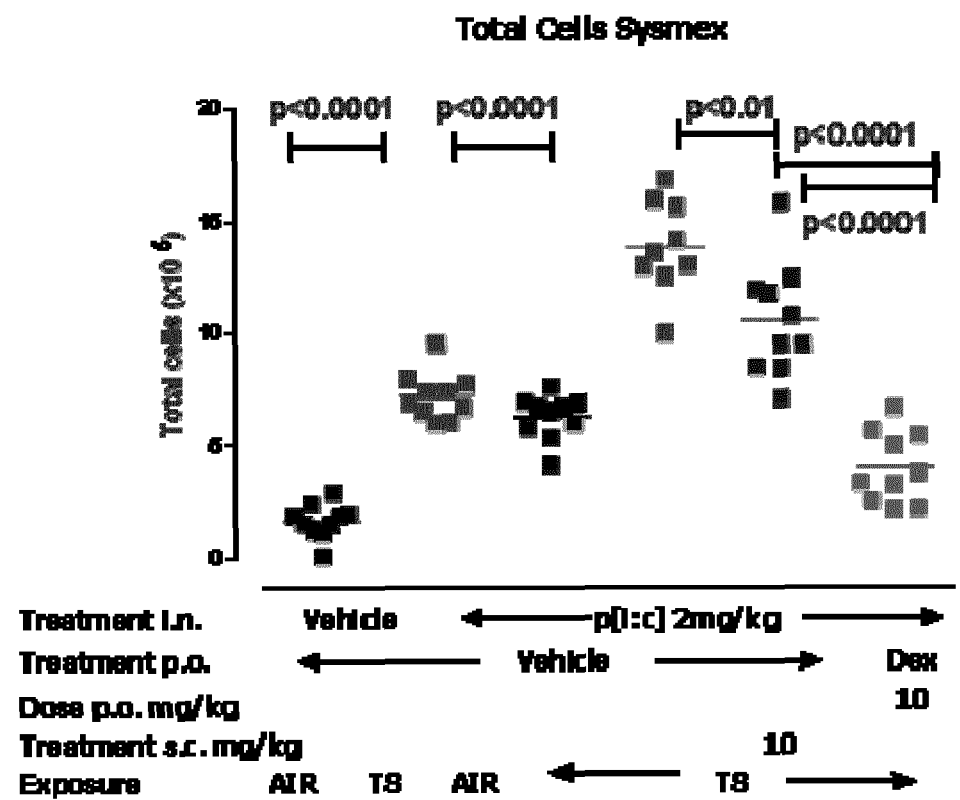
FIG. 6: Inhibition of total cell infiltration in the mouse lung airway space at day 5 after 1) air exposure, 2) tobacco smoke (TS), 3) p[I:C] alone, 4) p[I:C] combined to tobacco smoke at day 4 (induction of exacerbation), 5) p[I:C] combined to tobacco smoke at day 4 under IL-18BP treatment at 10 mg/kg, 6) dexamethasone treatment at 10 mg/kg. Statistical analyses were performed using ANOVA test (post-test Sidak's).

3. Exacerbated Inflammation Mitigation by IL-18BP in Exacerbation/Tobacco Smoke Mouse Model 3.1. Inhibition of Total Cell Infiltration and Exacerbated Inflammation in the Lung Airway Space by IL-18BP Mice treated by IL-18BP had a significant mitigation of total cell infiltration in the lung following induction of exacerbated inflammation. Doses of either 3 and 10 mg/kg indicated statistically valuable efficacy compared to the positive control dexamethasone (see FIG. 5). It is important to note that dexamethasone had no sign of efficacy at 3 mg/kg doses in the mouse model (data not shown), indicating that the high dexamethasone dose of 10 mg/kg is potentially inducing apoptosis in certain cell types such as macrophages, eosinophils and lymphocytes (data not shown). Similar observation was made with Roflumilast [3-(cyclopropylmethoxy)-N-(3,5-dichloropyridin-4-yl)-4-(difluoromethoxy) benzamide] in the mouse model where no hint of cell infiltration inhibition was observed with 2.5 mg/kg dose (data not shown). FIG. 6 shows clear and statistically relevant efficacy of IL-18BP at 10 mg/kg in exacerbated inflammation inhibition in the current mouse model.

3.2. Inhibition of Neutrophil Infiltration in the Lung Airway Space by IL-18BP

Figure 7:
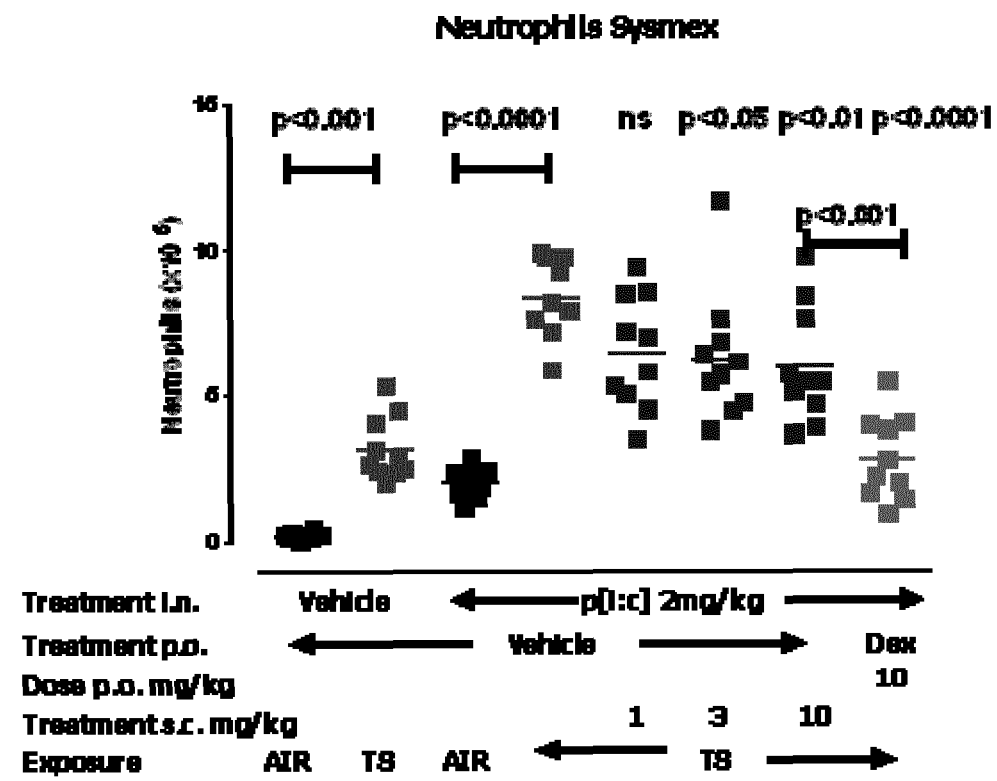
FIG. 7: Inhibition of neutrophil infiltration by IL-18BP. Neutrophil infiltration in the mouse lung airway space was monitored at day 5 after 1) air exposure, 2) tobacco smoke (TS), 3) p[I:C] alone, 4) p[I:C] combined to tobacco smoke at day 4 (induction of exacerbation), 5-7) p[I:C] combined to tobacco smoke at day 4 under IL-18BP treatment at either 1, 3 or 10 mg/kg, 8) dexamethasone treatment at 10 mg/kg. Statistical analyses were performed using ANOVA test (post-test Sidak's).
Figure 8:
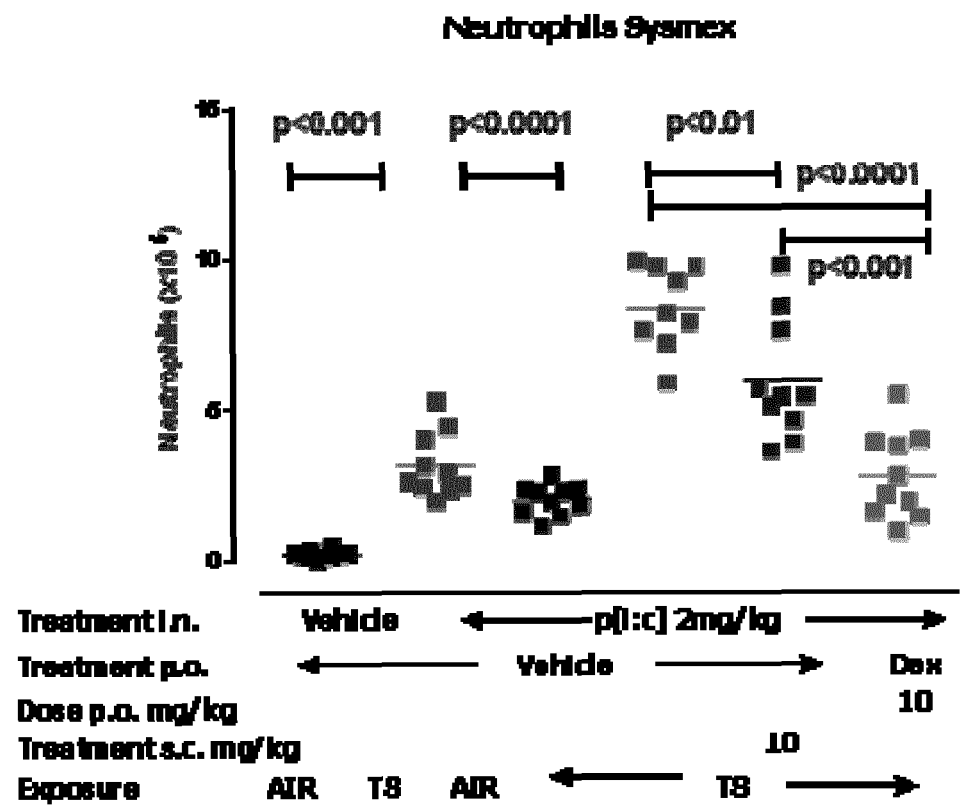
FIG. 8: Inhibition of neutrophil infiltration by IL-18BP. Neutrophil infiltration in the mouse lung airway space was monitored at day 5 after 1) air exposure, 2) tobacco smoke (TS), 3) p[I:C] alone, 4) p[I:C] combined to tobacco smoke at day 4 (induction of exacerbation), 5) p[I:C] combined to tobacco smoke at day 4 under IL-18BP treatment at 10 mg/kg, 6) dexamethasone treatment at 10 mg/kg. Statistical analyses were performed using ANOVA test (post-test Sidak's).

Neutrophil infiltration was inhibited by IL-18BP in tobacco smoke-exacerbated lungs. Doses of either 3 and 10 mg/kg IL-18BP indicated statistically valuable efficacy compared to the positive control dexamethasone (see FIG. 7). In the current mouse model conditions, IL-18BP 10 mg/kg dose seems to have the best statistical efficacy (see FIG. 8).

Figure 9:
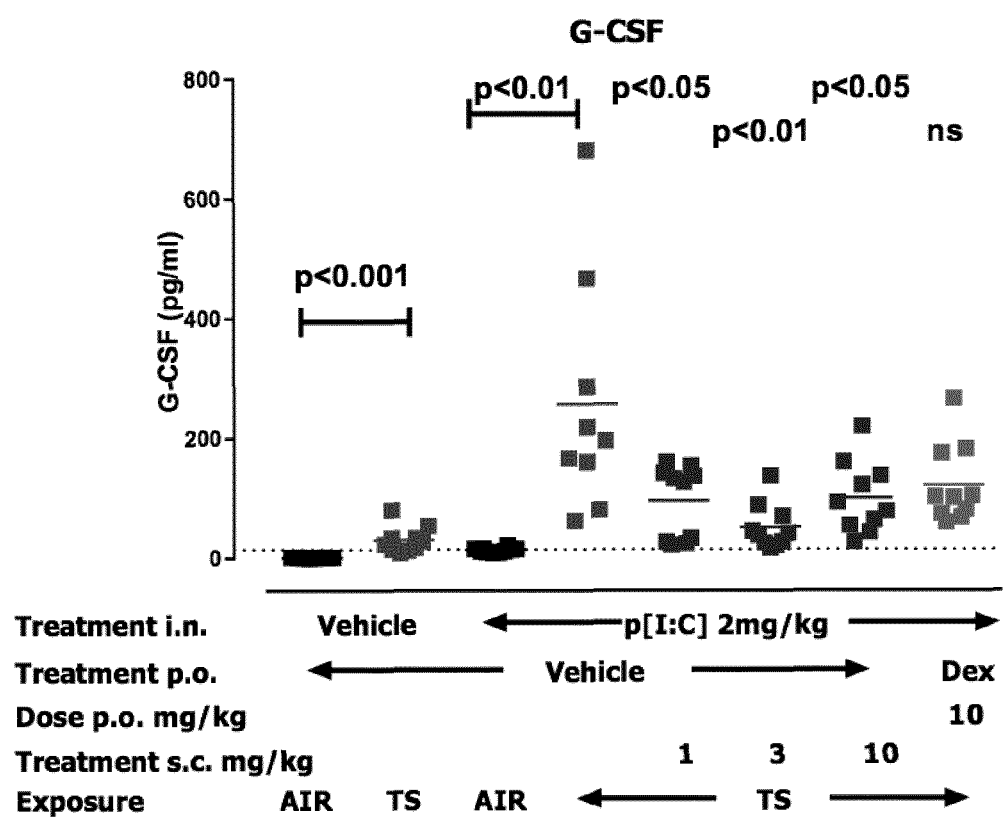
FIG. 9: Inhibition of G-CSF pathway by IL-18BP. The presence of G-CSF (pg/ml) was monitored in the mouse lung airway space by ELISA at day 5 after 1) air exposure, 2) tobacco smoke (TS), 3) p[I:C] alone, 4) p[I:C] combined to tobacco smoke at day 4 (induction of exacerbation), 5-7) p[I:C] combined to tobacco smoke at day 4 under IL-18BP treatment at either 1, 3 or 10 mg/kg, 8) dexamethasone treatment at 10 mg/kg. Dotted line indicates lower limit of detection. Statistical analyses were performed using Students t-test.

3.3. Inhibition of Granulocyte Colony-Stimulating Factor (G-CSF) Pathway in the Lung Airway Space by IL-18BP G-CSF is well acknowledged as key cytokine stimulating the survival, proliferation, differentiation, and function of neutrophil precursors and mature neutrophils. Consequently, mitigation of G-CSF pathway-induced by smoke-p[I:C] is an significant factor demonstrating an effect of IL-18BP on neutrophil recruitment in the mouse lung airway space. The presence of G-CSF in the BALF was monitored with a commercially available ELISA kit. FIG. 9 demonstrates that administration of IL-18BP mitigates G-CSF release in the lung airways, thereby confirming the inhibition of neutrophil infiltration. The three tested IL-18BP doses have a statistically relevant effect in the mouse model.

Figure 10:
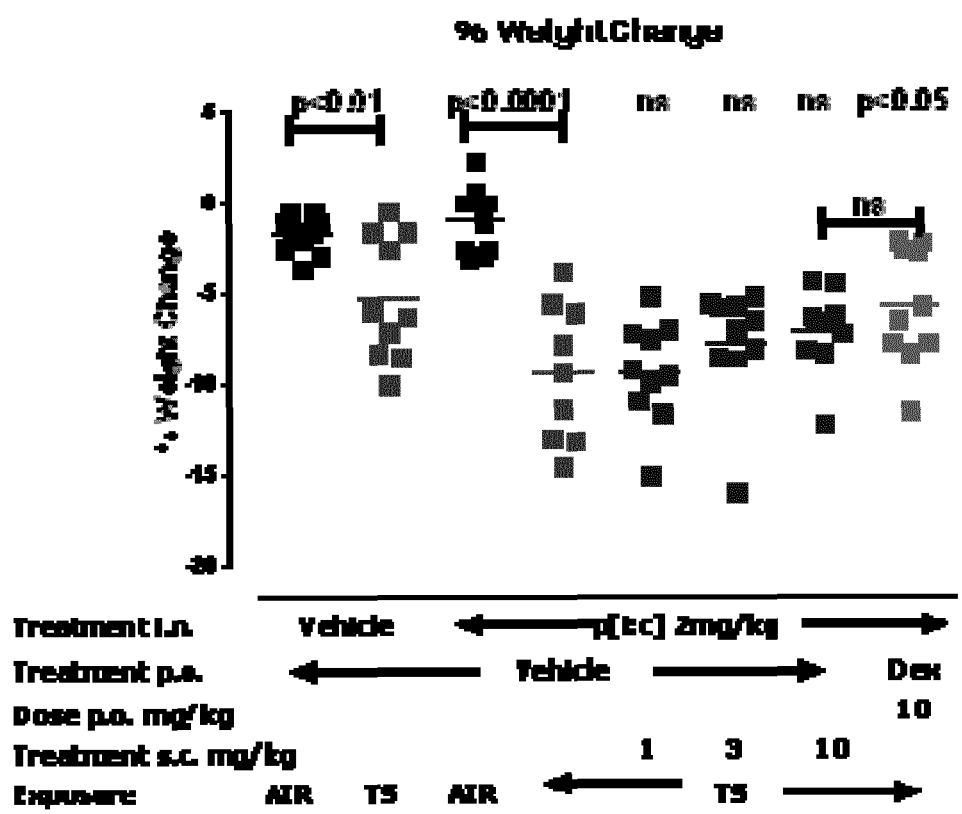
FIG. 10: Mitigation of weight loss by IL-18BP. Mouse weight loss was monitored at day 5 after 1) air exposure, 2) tobacco smoke (TS), 3) p[I:C] alone, 4) p[I:C] combined to tobacco smoke at day 4 (induction of exacerbation), 5) p[I:C] combined to tobacco smoke at day 4 under IL-18BP treatment at 10 mg/kg, 7) dexamethasone treatment at 10 mg/kg. Statistical analyses were performed using ANOVA test (post-test Sidak's).

3.4. IL-18BP Safety: Effect on Weight Loss in Exacerbation/Tobacco Smoke Mouse Model IL-18BP administration appeared to be well tolerated by exacerbation/tobacco smoke mouse model. As an example, weight loss was mitigated by IL-18BP even though both Students t-test and ANOVA statistical analyses were not significant (see FIG. 10). A large majority of mice receiving 3 and 10 mg/kg IL-18BP lost respectively 6-7% weight in contrast to the control exposed to tobacco smoke and p[I:C] that lost about 9%. Hence, weight loss alleviation data indicates that IL-18BP is not providing additional stress to the animal model. It is interesting to note that mice receiving only p[I:C] did not lose weight compared to mice receiving the combination of p[I:C] and tobacco smoke [see FIG. 8, treatment 3) and 4)].

C. Generation of Anti-IL-18 Monoclonal Antibodies

1. Mouse Immunization and Monoclonal Antibody Screening

Mice were vaccinated aginst human interleukin-18 using a technology allowing immunization with properly folded proteins. Prior to immunization, genetically modified mice were selected for major histocompatibility complexes supposedly sensitive to IL-18 surface area epitopes binding IL-18BP. Following immunization, B cells were isolated from spleen and hybridized following standard hybridoma technology. Hybridoma were sorted onto microplates and then tested for expression of monoclonal anti-IL-18 antibodies targeting IL-18 epitopes included in IL-18BP binding site. The screening was performed in 3 sequential and selective steps:

First step. Positive antibody screening attempt was performed with IL-18 attached to Luminex beads confirming cell expressing monoclonal anti-IL-18 antibodies.

Second step. Potential antibodies targeting IL-18 on IL-18BP binding site were rescreened in competition with IL-18BP. For this, monoclonal antibodies were bound to Luminex beads carrying IL-18. The complex was then exposed to biotinylated IL-18BP in order to identify interference to previously identified anti-IL-18 antibodies (see Table 1, Column #2). The second screening carried more than 300 positive antibody candidates (see Table 1, Column #3). The number of positive candidates was surprisingly high suggesting an excellent mouse immunization to the targeted epitope area. However, inhibitions were not sufficient due to diminished but still persistent fluorescence signals, thus indicating binding of IL-18BP to the complexed antibody IL-18. Nevertheless and importantly, such standard screening method reported elsewhere does not take into account a potential steric hindrance of the large antibody molecule (about 160 kDa) against the much smaller IL-18BP (about 18 kDa, peptide only).

Third step. A third screening program was undertaken with Luminex beads linked to IL-18BP and then complexed to interleukin-18, assuring the presentation of properly folded recombinant IL-18 to positive antibody candidates. The resulting screening was considerably more selective because most of the above antibodies still bound the Luminex-IL-18 beads thereby indicating that their previous inhibitory effect to IL-18BP was due to steric hindrance. Finally, a total of 12 antibodies were finally considered as targeting IL-18 on the IL-18BP protein due to their very low fluorescence signal after binding IL-18 in the presence of IL-18BP, namely clone #107C6, 108F8, 109A6, 111A6, 129C3, 131B4, 131E8, 131H1, 132C12, 132H4, 133A6 and 134B2 (see Table 16, Column #4, selected clones representing inhibition means of more than 500 fold compared to Column #2). The positive antibodies versus a set of negatives are presented in Table 16 below.

The collected data from third screening step (Table 16, Column #4) promoted further mRNA sequencing and clone dilution work to enrich positive monoclonal cells out of #107C6, 108F8, 109A6, 111A6, 129C3, 131B4, 131E8, 131H1, 132C12, 132H4, 133A6 and 134B2. All of these monoclonal antibodies were confirmed to bind to IL-18 on the IL-18BP binding site.

TABLE 16

Screening of monoclonal antibodies targeting IL-18 on the IL-18BP binding site

| Clone name | Column #1 Monoclonal antibodies binding on IL-18 | Column #2 IL-18BP binding on IL-18 previously complexed to monoclonal antibody Fluorescence intensity | Column #3 Monoclonal antibody binding on IL-18 previously complexed to IL-18BP |
|---|---|---|---|
| Examples of negative antibodies not following selection criteria | | | |
| 101D2 | 26 963 | 1 226 | 1 544 |
| 104H10 | 26 508 | 1 199 | 2 499 |
| 105A2 | 21 528 | 1 886 | 1 840 |
| 106H1 | 27 178 | 1 011 | 1 324 |
| 108F3 | 23 496 | 1 964 | 2 383 |
| 108G6 | 25 652 | 1 137 | 2 507 |
| 115E6 | 25 752 | 1 604 | 2 649 |
| 119E9 | 25 420 | 1 307 | 2 931 |
| Positive antibodies following selection criteria | | | |
| 107C6 | 26 250 | 1 389 | 33 |
| 108F8 | 25 126 | 1 292 | 45 |
| 109A6 | 25 848 | 913 | 33 |
| 111A6 | 25 855 | 1 398 | 42 |
| 131B4 | 24 838 | 1 656 | 41 |
| 131E8 | 25 411 | 1 389 | 36 |
| 131H1 | 24 806 | 1 026 | 24 |
| 132C12 | 24 541 | 1 515 | 48 |
| 132H4 | 23 839 | 1 488 | 28 |
| 133A6 | 23 273 | 1 631 | 25 |
| 134B2 | 24 278 | 1 261 | 48 |
| 129C3 | 25 412 | 760 | 44 |

REFERENCES

Argiriadi M A, Xiang T, Wu C, Ghayur T and Borhani D W. Unusual water-mediated antigenic recognition of the proinflammatory cytokine interleukin-18. *J Biol Chem* 2009; 284(36)24478-24489.

Azoulay E, Eddahibi S, Marcos E, Levame M, Harf A, Schlemmer B, Adnot S and Delclaux C. Granulocyte colony-stimulating factor enhances alpha-naphthylthiourea-induced pulmonary hypertension. *J Appl Physiol* 2003; 94:2027-2033.

Baron R M, Choi A J S, Owen C A and Choi A M K. Genetically manipulated mouse models of lung disease: potential and pitfalls. *Am J Physiol Lung Cell Mol Physiol* 2012; L485-L497.

Chen D Y, Lan J L, Lin F J and Hsieh T Y. Proinflammatory cytokine profiles in sera and pathological tissues of patients with active untreated adult onset Still's disease. *J Rheumatol* 2004; 31:2189-2198.

Chen D Y, Lan J L, Lin F J, Hsieh T Y and Wen M C. Predominance of Th1 cytokine in peripheral blood and pathological tissues of patients with active untreated adult onset Still's disease. *Ann Rheum Dis* 2004; 63(10):1300-1306.

Cunningham R E. Tissue disaggregation. *Methods Mol Biol* 1994; 34:225-228.

Daley E, Emson C, Guignabert C, de Waal Malefyt R, Louten J, Kurup V P, Hogaboam C, Taraseviciene-Stewart L, Voelkel N F, Rabinovitch M, et al. Pulmonary arterial remodeling induced by a Th2 immune response. *J Exp Med* 2008; 205:361-372.

Elias J A, Kang M J, Crothers K et al. Mechanistic heterogeneity in chronic obstructive pulmonary disease: insights from transgenic mice. *Proc Am Thorac Soc* 2006; 494-498.

Eltom S, Stevenson C S and Rastrick J. P2X7 Receptor and Caspase-1 Activation Are Central to Airway Inflammation Observed after Exposure to Tobacco Smoke *PLoS ONE* 2011; 6(9):e24097.

Hackett B P, Shimizu N and Gitlin J D. Clara cell secretory protein gene expression in bronchiolar epithelium. *Am J Physiol* 1992; 262:L399-L404.

Halbower A C, Mason R J, Abman S H and Tuder R M. Agarose infiltration improves morphology of cryostat sections of lung. *Lab Invest* 1994; 71: 149-153.

Hautamaki R D, Kobayashi D K, Senior R M and Shapiro S D. Requirement for macrophage elastase for cigarette smoke-induced emphysema in mice. *Science* 1997; 277: 2002-2004.

Hoshino T, Kawase Y, Okamoto M et al. IL-18-transgenic mice: in vivo evidence of a broad role for IL-18 in modulating immune function. *J Immunol* 2001; 7014-7018.

Hoshino T, Kato S, Oka N et al. Pulmonary inflammation and emphysema: role of the cytokines IL-18 and IL-13. *Am J Respir Crit Care Med* 2007; 49-62.

Helmut Fenner. Targeting IL-18 in Chronic Obstructive Pulmonary Disease: Background and rationale. Mar. 22, 2013 CONFIDENTIAL Page 19.

Hou S, Li B, Wang L, Qian W, Zhang D, Hong X, Wang H, Guo Y (July 2008). "Humanization of an anti-CD34 monoclonal antibody by complementarity-determining region grafting based on computer-assisted molecular modeling.". *J Biochem* 144 (1): 115-20

Imaoka H, Hoshino T, Takei S, Kinoshita T et al. Interleukin-18 production and pulmonary function in COPD. *Eur Respir J* 2008; 287-97.

Jaatinen T, Laine J. Isolation of mononuclear cells from human cord blood by Ficoll-Paque density gradient. *Curr Protoc Stem Cell Biol* 2007; Chapter 2:Unit 2A.1.

Kang M J, Lee C G, Lee J Y, Dela Cruz C S, Chen Z J, Enelow R, Elias J A. Cigarette smoke selectively enhances viral PAMP- and virus-induced pulmonary innate immune and remodeling responses in mice. *J Clin Invest* 2008; 118:2771-2784.

Kang M J, Homer R J, Gallo A et al. IL-18 is induced and IL-18 receptor alpha plays a critical role in the pathogenesis of cigarette smoke-induced pulmonary emphysema and inflammation. *J Immunol* 2007; 1948-1959.

Kang M J, Choi J M, Kim B H et al. IL-18 induces emphysema and airway and vascular remodeling via IFN-γ, IL-17A, and IL-13. *Am J Respir Crit Care Med* 2012; 1205-1217.

Kashmiri S V, De Pascalis R, Gonzales N R, Schlom J. (May 2005). "SDR grafting—a new approach to antibody humanization.". *Methods* 36 (1): 25-34

Kawashima, M. et al. Levels of interleukin-18 and its binding inhibitors in the blood circulation of patients with adult-onset Still's disease. *Arthritis Rheum* 2001; 44(3): 550-560.

Kim, S. H. et al. Structural requirements of six naturally occurring isoforms of the IL-18 binding protein to inhibit IL-18. *Proc Natl Acad Sci USA* 2000; 97(3):1190-1195.

Kratzer A, Salys J, Nold-Petry El al. Role of IL-18 in second hand smoke-induced emphysema. *Am J Respir Cell Mol Biol* 2013; 48(6):725-32.

Lee C G, Link H, Baluk P, Homer R J, Chapoval S, Bhandari V, Kang M J, Cohn L, Kim Y K, McDonald D M, et al. Vascular endothelial growth factor (VEGF) induces remodeling and enhances TH2-mediated sensitization and inflammation in the lung. *Nat Med* 2004; 10:1095-1103.

Lee C G, Hartl D, Lee G R, Koller B, Matsuura H, Da Silva C A, Sohn M H, Cohn L, Homer R J, Kozhich A A, et al. Role of breast regression protein 39 (BRP-39)/chitinase 3-like-1 in Th2 and IL-13-induced tissue responses and apoptosis. *J Exp Med* 2009; 206:1149-1166.

Liu J et al. Requirement for tumor necrosis factor-receptor 2 in alveolar chemokine expression depends upon the form of the ligand. *Am J Respir Cell Mol Biol* 2005; 33:463-469.

Londhe V A, Maisonet T M, Lopez B, Jeng J M, Li C, Minoo P. A subset of epithelial cells with CCSP promoter activity participates in alveolar development. *Am J Respir Cell Mol Biol* 2011; 44:804-812.

Loza M J, Watt R, Baribaud F, Barnathan E S and Rennard S I. Systemic inflammatory profile and response to anti-tumor necrosis factor therapy in chronic obstructive pulmonary disease. *Respir Res* 2012; 13:12.

Ma B, Kang M J, Lee C G, Chapoval S, Liu W, Chen Q, Coyle A J, Lora J M, Picarella D, Homer R J and Elias J A. Role of CCR5 in IFN-γ-induced and cigarette smoke-induced emphysema. *J Clin Invest* 2005; 115:3460-3472.

Nakajima T and Owen C. Interleukin-18: The Master Regulator Driving Destructive and Remodeling Processes in the Lungs of Patients with Chronic Obstructive Pulmonary Disease? *Am J Respir Crit Care Med* 2012; 1137-1138.

Novick D et al. A novel IL-18BP ELISA shows elevated serum IL-18BP in sepsis and extensive decrease of free IL-18. *Cytokine* 2001; 14, 334-342.

Novick D et al. High circulating levels of free interleukin-18 in patients with active SLE in the presence of elevated levels of interleukin-18 binding protein. *J Autoimmun* 2010; 34, 121-126.

Park M C, Park Y B and Lee S K. Elevated interleukin-18 levels correlated with disease activity in systemic lupus erythematosus. *Clin Rheumatol* 2004; 23, 225-229.

Petersen A M W, Penkowa M and Iversen M. Elevated Levels of IL-18 in Plasma and Skeletal Muscle in Chronic Obstructive Pulmonary Disease. *Lung* 2007; 161-171.

Queen C, Schneider W P, Selick H E, Payne P W, Landolfi N F, Duncan J F, Avdalovic N M, Levitt M, Junghans R P, Waldmann T A. (December 1989). "A humanized antibody that binds to the interleukin 2 receptor.". *Proc Natl Acad Sci USA*. 86 (24): 10029-33

Rastrick J M D, Stevenson C S, Eltom S, Grace M, Davies M, et al. Cigarette Smoke Induced Airway Inflammation Is Independent of NF-κB Signalling. *PLoS ONE* 2013; 8(1):e54128.

Ray P, Tang W, Wang P, Homer R, Kuhn C III, Flavell R A and Elias J A. Regulated overexpression of interleukin 11 in the lung: use to dissociate development-dependent and -independent phenotypes. *J Clin Invest* 1997; 100:2501-2511.

Reed L J and Muench H. A simple method of estimating 50% endpoints. *Am J Hyg* 1938; 27:493-497.

Riechmann L, Clark M, Waldmann H, Winter G (1988). "Reshaping human antibodies for therapy". *Nature* 332 (6162): 332-323

Rovina N, Dima E and Gerassimou C. Interleukin-18 in induced sputum: Association with lung function in chronic obstructive pulmonary disease. *Respiratory Medicine* 2009; 1056-1062.

Shapiro D S. Transgenic and gene-targeted mice as models for chronic obstructive pulmonary disease. *Eur J Respir* 2007; 375-378.

Taniguchi, M. et al. Characterization of anti-human interleukin-18 (IL-18)/interferon-gamma-inducing factor (IGIF) monoclonal antibodies and their application in the measurement of human IL-18 by ELISA. *J Immunol Methods* 1997; 206, 107-113.

Wang Z, Zheng, Zhu T Z, Homer R J, Riese R J, Chapman H A, Shapiro S D, and Elias J A. Interferon γ induction of pulmonary emphysema in the adult murine lung. *J Exp Med* 2000; 192: 1587-1600.

Wright J L, Cosio M and Churg A. Animal models of chronic obstructive disease. *Am J Physiol Lung Cell Mol Physiol* 2008; L1-L15.

Wong C K, Li E K, Ho C Y and Lam C W. Elevation of plasma interleukin-18 concentration is correlated with disease activity in systemic lupus erythematosus. *Rheumatology* (Oxford) 2000; 39:1078-1081.

Zhang J, Dong Z, Zhou R, Luo D, Wei H and Tian Z. Isolation of lymphocytes and their innate immune characterizations from liver, intestine, lung and uterus. Cell Mol Immunol 2005; 2:271-280.

Zheng T, Zhu Z, Wang Z, Homer R J, Ma B, Riese R, Chapman H, Shapiro S D and Elias J A. Inducible targeting of IL-13 to the adult lung causes matrix metalloproteinase- and cathepsin-dependent emphysema. *J Clin Invest* 2000; 106:1081-1093.

Zheng T et al. Role of cathepsin S-dependent epithelial cell apoptosis in IFN-gamma-induced alveolar remodeling and pulmonary emphysema. *J Immunol* 2005; 174:8106-8115.

Further Embodiments of the Invention

1. An IL-18 inhibitor for use in the treatment of an IL-18 associated disease or disorder in a subject diagnosed of having abnormal levels of free IL-18 and/or an abnormal ratio of free IL-18/IL-18BP in the body fluids compared to the levels in body fluids of a healthy control subject.
2. The IL-18 inhibitor for use according to embodiment 1, wherein said abnormal level of free IL-18 in the body fluids exceeds the level in body fluids of a healthy control subject by 5%, 10%, 20%, 30%, 40%, 50%, 60%, 70%, 80%, 90%, 100%, or more than 100%.
3. The IL-18 inhibitor for use in any one of the preceding embodiments, wherein the subject to be treated belongs to a group of subjects which have been determined to have elevated levels of free IL-18 and/or an abnormal ratio of free IL-18/IL-18BP (IL-18BP) in the body fluids, particularly serum, sputum, broncho-alveolar lavage fluid (BALF), synovial fluid and/or circulation compared to the levels in the body fluids of a healthy subject.
4. The IL-18 inhibitor for use in embodiments 2 or 3, wherein said elevated levels of free IL-18 in serum are in the range of 5 to 10000 pg/mL, whereas the amount of free IL-18 in serum of healthy subject, particularly a healthy human is ≤4 pg/mL.
5. The IL-18 inhibitor for use according to any one of the preceding embodiments, wherein said IL-18 associated disease or disorder is one selected from the group consisting of chronic obstructive pulmonary disease (COPD), transfusion-related lung injury, bronchopulmonary dysplasia (BPD), acute respiratory distress syndrome (ARDS), Adult Still's disease, juvenile Still's disease, interstitial lung disease (ILD), idiopathic pulmonary fibrosis, cystic fibrosis, pulmonary arterial hypertension, asthma, bronchiectasis, heart failure, amyotrophic lateral sclerosis (ALS), dry eye disease (DED), keratitis, corneal ulcer and abrasion, corneal neovascularization, pathological intraocular neovascularization, iritis, glaucoma, macular degeneration, Sjögren's syndrome, autoimmune uveitis, Behçet's disease, conjunctivitis, allergic conjunctivitis, dermatitis of eyelid, diabetes type 2, non-alcoholic fatty liver disease (NAFLD), steato hepatitis, solid organ and hematologic transplantation, ischemia reperfusion injury, familial Mediterranean fever, tumor necrosis factor receptor 1-associated periodic syndromes, cryopyrin-associated periodic fever syndromes, hyper-IgD syndromes, gout, Schnitzler syndrome, Wegener's granulomatosis also called granulomatosis with polyangitis (GPA), Hashimoto's thyroiditis, Crohn's disease, ulcerative colitis, immunoglobulin-4 (IgG4)-related diseases and stem cell therapies.
6. The IL-18 inhibitor for use according to any one of the preceding embodiments, wherein said IL-18 associated disease or disorder is induced by smoking or second-hand smoke exposure, in particular tobacco smoke exposure.
7. The IL-18 inhibitor for use according to any one of the preceding embodiments, wherein said IL-18 associated disease or disorder is induced by viral infection.
8. The IL-18 inhibitor for use according to any one of the preceding embodiments, wherein said IL-18 associated disease or disorder is an IL-18 induced systemic manifestation of inflammation and associated comorbidities selected from the group consisting of emphysema, tissue inflammation, tissue destruction, lung resection, disappearance of the vasculature, apoptosis of endothelial cells, mucos metaplasia, cardiac hypertrophy, decrease of VEGF in the lung tissue, pulmonary vessel loss, vessel muscularization, vascular remodeling, collagen deposition, aberrant elastin layers in the lung, fibrotic airway remodeling, airspace enlargement, chronic remodeling of the airways and pulmonary vessels and decreased pulmonary function.
9. The IL-18 inhibitor for use in any one of the preceding embodiments, wherein treatment comprises prevention, halting, alleviation or reversion of symptoms associated with said disease or disorder.
10. The IL-18 inhibitor for use in any one of the preceding embodiments, wherein IL-18 binding is restricted or inhibited, particularly binding of free IL-18 to IL-18R, but especially binding of free IL-18 to IL-18Rα.
11. The IL-18 inhibitor for use in any one of the preceding embodiments, wherein IL-18-dependent downstream signaling pathways are modified, particularly inhibited.
12. The IL-18 inhibitor for use in any one of the preceding embodiments, wherein increased expression of IFN-γ, IL-13 or IL-17A is modified, particularly inhibited, compared to untreated subjects suffering from said disease or disorder.
13. The IL-18 inhibitor for use in any one of the preceding embodiments, wherein the IL-18 inhibitor compensates the IL-18/IL-18BP imbalance by trapping and neutralizing the excess of free IL-18 in tissue and circulation.
14. An IL-18 specific antibody including any functionally equivalent antibody or parts thereof, which antibody or part thereof binds to IL-18 at the binding site of IL-18BP or in the vicinity of the binding site of IL-18BP.
15. The IL-18 specific antibody including any functionally equivalent antibody or parts thereof according to embodiment 14, which antibody of part thereof binds free IL-18 protein, but not IL-18/IL-18BP complexes.
16. The IL-18 specific antibody including any functionally equivalent antibody or parts thereof according to embodiment 14 or embodiment 15, wherein said antibody or part thereof sterically hinders or prevents the binding of IL-18BP to IL-18.
17. The IL-18 specific antibody including any functionally equivalent antibody or parts thereof according to embodiments 14 to 16, wherein said antibody or part thereof specifically binds to a single epitope, a combination of two epitopes or a combination of 3 epitopes comprised in a sequence selected from a group of sequences depicted in SEQ ID NO.: 1, SEQ ID NO: 2 and SEQ ID NO: 3.

18. The IL-18 specific antibody including any functionally equivalent antibody or parts thereof according to embodiment 17, wherein said epitope has a sequence which has 90%, 91%, 92%, 93%, 94%, 95%, 96%, 97%, 98%, 99%, 100% sequence identity to a sequence selected from a group of sequences depicted in SEQ ID NO: 4, SEQ ID NO: 5 and SEQ ID NO: 6.

19. The IL-18 specific antibody including any functionally equivalent antibody or parts thereof according to embodiment 18, wherein said epitope is selected from the group consisting of SEQ ID NO: 4, SEQ ID NO: 5 and SEQ ID NO: 6.

20. The IL-18 specific antibody including any functionally equivalent antibody or parts thereof according to any one of the preceding embodiments, wherein said antibody or part thereof is a monoclonal antibody or a polyclonal antibody.

21. The IL-18 specific antibody including any functionally equivalent antibody or parts thereof according to any one of the preceding embodiments, wherein said antibody or part thereof is a chimeric, single chain, bispecific, simianized, human and humanized antibody.

22. The IL-18 specific antibody including any functionally equivalent antibody or parts thereof according to any one of the preceding embodiments, wherein said antibody or part thereof binds to human IL-18.

23. The IL-18 specific antibody including any functionally equivalent antibody or parts thereof according to any one of the preceding embodiments, wherein binding of IL-18 to IL-18 receptor, particularly binding to IL-18Rα is reduced by at least 5%, particularly by at least 10%, particularly by at least 15%, particularly by at least 20%, particularly by at least 25%, particularly by at least 30%, particularly by at least 40%, particularly by at least 45%, particularly by at least 50%, particularly by at least 55%, particularly by at least 60%, particularly by at least 65%, particularly by at least 70, particularly by at least 75, particularly by at least 80, particularly by at least 85%, particularly by at least 90%, particularly by at least 95%, particularly by 100%.

24. The IL-18 specific antibody including any functionally equivalent antibody or parts thereof according to any one of the preceding embodiments, wherein said antibody or part thereof neutralizes free IL-18 by restricting or preventing IL-18 binding to IL-18 receptor (IL-18R), especially free IL-18 binding to IL-18Rα.

25. The IL-18 specific antibody including any functionally equivalent antibody or parts thereof according to any one of the preceding embodiments, wherein said antibody or parts thereof
a) specifically binds to a single epitope, a combination of two epitopes or a combination of 3 epitopes comprised in a sequence selected from a group of sequences depicted in SEQ ID NO:1, SEQ ID NO: 2 and SEQ ID NO: 3; and/or
b) specifically binds to an epitope, which has a sequence identity of 90%, 91%, 92%, 93%, 94%, 95%, 96%, 97%, 98%, 99% or 100% to the sequence depicted in SEQ ID NO: 4, SEQ ID NO:5 or SEQ ID NO: 6; and
c) specifically binds to IL-18 at the binding site of IL-18BP or in the vicinity of the binding site of IL-18BP; and
d) specifically binds to free IL-18 protein, but not IL-18/IL-18BP complexes; and e) sterically hinders the binding of IL-18BP to IL-18; and
f) reduces binding of IL-18 to IL-18 receptor, particularly binding to IL-18Rα by at least 5%, particularly by at least 10%, particularly by at least 15%, particularly by at least 20%, particularly by at least 25%, particularly by at least 30%, particularly by at least 40%, particularly by at least 45%, particularly by at least 50%, particularly by at least 55%, particularly by at least 60%, particularly by at least 65%, particularly by at least 70, particularly by at least 75, particularly by at least 80, particularly by at least 85%, particularly by at least 90%, particularly by at least 95%, particularly by 100%.

26. The IL-18 inhibitor for use according to any one of embodiments 1 to 13, wherein the inhibitor is an antibody, particularly an antibody specific for free IL-18, particularly an antagonistic antibody, which prevents binding of free IL-18 to IL-18 receptor, especially free IL-18 binding to IL-18Rα.

27. The IL-18 inhibitor for use according to embodiment 26, wherein said antibody is the antibody of any one of embodiments 14-25.

28. The IL-18 inhibitor for use according to any one of embodiments 1-13, wherein said abnormal levels of free IL-18 in the body fluids has been determined by use of an antibody according to any one of embodiments 14-25.

29. The IL-18 inhibitor for use according to any one of the embodiments 1 to 13, wherein the inhibitor is IL-18BP, particularly human IL-18BP (hIL-18BP), particularly IL-18BP including any functionally equivalent or parts thereof, particularly an IL-18BP as shown in SEQ ID NO: 7.

30. The IL-18 inhibitor for use in according to embodiments 26-29, which is a full-length protein or a mutein, functional derivative, functional fragment, biologically active peptide, fraction, circularly permuted derivative, fused protein, isoform or a salt thereof.

31. IL-18BP for use in the treatment of chronic obstructive pulmonary disease (COPD), heart disease, dry eye disease and/or diabetes type II.

32. The IL-18BP for use according to embodiment 31 for the treatment of chronic obstructive pulmonary disease (COPD).

33. The IL-18BP for use according to embodiment 31 for the treatment of heart disease.

34. The IL-18BP for use according to embodiment 31 for the treatment of dry eye disease.

35. The IL-18BP for use according to embodiment 31 for the treatment of diabetes type II.

36. The IL-18BP for use according to embodiments 31 to 35, wherein said disease or disorder is induced by smoking or second-hand smoke exposure, in particular tobacco smoke exposure.

37. The IL-18BP for use according to any one of the preceding embodiments, wherein said disease or disorder is induced by viral infection.

38. The IL-18BP for use according to any one of the preceding embodiments, wherein said disease or disorder is an IL-18 induced systemic manifestation of inflammation and associated comorbidities selected from the group consisting of emphysema, tissue inflammation, tissue destruction, lung resection, disappearance of the vasculature, mucos metaplasia, cardiac hypertrophy, decrease of VEGF in the lung tissue, pulmonary vessel loss, vessel muscularization, collagen deposition, aberrant elastin layers in the lung, fibrotic airway remodeling, airspace enlargement, chronic remodeling of the airways and pulmonary vessels and decreased pulmonary function.

39. The IL-18BP for use according to any one of the preceding embodiments, wherein IL-18 binding is restricted or inhibited, particularly binding of free IL-18 to IL-18R, but especially free IL-18 binding to IL-18Rα.

40. The IL-18BP for use according to any one of the preceding embodiments, wherein IL-18-dependent downstream signaling pathways are modified, particularly inhibited.

41. The IL-18BP for use according to any one of the preceding embodiments, wherein increased expression of IFN-γ, IL-13 or IL-17A is modified, particularly inhibited, compared to untreated subjects suffering from said disease or disorder.

42. The IL-18BP for use according to any one of the preceding embodiments, wherein the IL-18 inhibitor compensates the IL-18/IL-18BP imbalance by trapping the excess of free IL-18 in tissue and circulation.

43. The IL-18BP for use according to any one of the preceding embodiments, wherein treatment comprises prevention, halting, alleviation or reversion of symptoms associated with said disease or disorder.

44. A pharmaceutical composition for use in the treatment of the disease or disorder as defined in any one of embodiments 1-13 in a subject suffering from such a disease or disorder or having a predisposition to develop such a disease or disorder as defined in any one of embodiments 1-13, wherein said composition comprises the IL-18 inhibitor according to any one of embodiments 1-13 and 26-30, particularly in a prophylactically and/or therapeutically effective amount.

45. The pharmaceutical composition of embodiment 44, wherein said composition optionally further provides another inhibitor of a pro-inflammatory cytokine or functional fragment thereof, or a regulatory factor, which induces in-situ expression of said inhibitor of pro-inflammatory cytokine or functional fragment thereof, co-therapeutic agents such as anti-inflammatory, bronchodilatory, antihistamine, decongestant or anti-tussive drug substances.

46. The pharmaceutical composition of embodiment 44 or 45, comprising a pharmaceutically acceptable carrier and/or excipient.

47. A pharmaceutical composition for use in the treatment of the disease or disorder as defined in any one of embodiments 31 to 43 in a subject suffering from such a disease or disorder or having a predisposition to develop such a disease or disorder as defined in any one of embodiments 31 to 43, wherein said composition comprises the IL-18BP according to embodiments 31 to 43, particularly in a prophylactically and/or therapeutically effective amount.

48. The pharmaceutical composition of embodiment 47, wherein said composition optionally further provides another inhibitor of a pro-inflammatory cytokine or functional fragment thereof, or a regulatory factor, which induces in-situ expression of said inhibitor of pro-inflammatory cytokine or functional fragment thereof, co-therapeutic agents such as anti-inflammatory, bronchodilatory, antihistamine, decongestant or anti-tussive drug substances.

49. The pharmaceutical composition of embodiment 47 or 48, comprising a pharmaceutically acceptable carrier and/or excipient.

50. An expression vector comprising a coding sequence of the IL-18 inhibitor according to any one of embodiments 1-13 and 26-30, which upon administration to a subject suffering from a disease or disorder or having a predisposition to develop such a disease or disorder as defined in the preceding embodiments leads to in situ expression of IL-18 inhibitor for use in the treatment of the disease or disorder as defined in any one of embodiments 1-13.

51. An expression vector comprising an IL-18 antisense expressing vector, which upon administration to a subject suffering from a disease or disorder or having a predisposition to develop such a disease or disorder as defined in embodiments 1-13, leads to in situ inhibition of the expression of IL-18 for use in the treatment of the disease or disorder as defined in any one of embodiments 1-13.

52. The expression vector of embodiment 50 or 51 for use in the treatment of the disease or disorder as defined in any one of embodiments 1-13 and 26-43, wherein said expression vector is administered to a subject suffering from such a disease or disorder, or having a predisposition to develop such a disease or disorder, alone or in combination with the IL-18 inhibitor according to any one of embodiments 1-13 and 26-30, the IL-18BP according to embodiments 31-43 or the pharmaceutical composition according to any one of embodiments 44-49.

53. An expression vector comprising the coding sequence of IL-18BP according to embodiments 31-43, which upon administration to a subject suffering from a disease or disorder or having a predisposition to develop such a disease or disorder as defined in the preceding embodiments, leads to in situ expression of IL-18BP for use in the treatment of the disease or disorder as defined in any one of embodiments 31-43.

54. The expression vector of embodiment 53 for use in the treatment of the disease or disorder as defined in any one of embodiments 1-13 and 26-43, wherein said expression vector is administered to a subject suffering from such a disease or disorder, or having a predisposition to develop such a disease or disorder, alone or in combination with the IL-18 inhibitor according to any one of embodiments 1-13 and 26-30, the IL-18BP according to embodiments 31-43 or the pharmaceutical composition according to any one of embodiments 44-49.

55. The IL-18 inhibitor for use according to any one of embodiments 1-13 and 26-30, the IL-18BP for use according to any one of embodiments 31-43, the pharmaceutical composition for use according to any one of embodiments 44-49 or the expression vector for use according to any one of embodiments 50-54, comprising administering to a subject in need thereof a prophylactically and/or therapeutically effective amount of said IL-18 inhibitor, IL-18BP, pharmaceutical composition, or expression vector, particularly by systemic, intranasal, buccal, oral, transmucosal, intratracheal, intravenous, subcutaneous, intraurinary tract, intravaginal, sublingual, intrabronchial, intrapulmonary, transdermal or intramuscular administration, in particular broncho-pulmonary administration.

56. The IL-18 inhibitor, the IL-18BP, the pharmaceutical composition or the expression vector for use according to embodiment 55, wherein said subject is a mammal, particularly said subject is a human.

57. A method for treating the disease or disorder as defined in any one of embodiments 1-13 and 26-43 in a subject suffering from such a disease or disorder, or having a predisposition to develop such a disease or disorder, comprising administering to said subject a therapeutically or prophylactically effective amount of the IL-18 inhibitor according to any one of embodiments 1-13 and 26-30, the IL-18BP according to embodiments 31-43 or the pharmaceutical composition according to any one of embodiments 44-49 and/or the expression vector according to any one of embodiments 50-54, particularly by systemic, intranasal, buccal, oral, transmucosal, intratracheal, intravenous, subcutaneous, intraurinary tract, intravaginal, sublingual, intrabronchial, intrapulmonary, transdermal or intramuscular administration, in particular broncho-pulmonary administration.

58. A method for diagnosis of the diseases or disorder as defined in any one of embodiments 1-13 and 26-43, for diagnosing a predisposition to the disease or disorder as defined in any one of embodiments 1-13 and 26-43, for monitoring minimal residual disease in a subject, or for predicting responsiveness of a subject to a treatment with IL-18 inhibitor according to embodiments 1-13 and 26-30, the IL-18BP according to embodiments 31-43 or the pharmaceutical composition comprising IL-18 inhibitor according to embodiments 44-49, comprising the steps:
    a) obtaining a sample of body fluid, particularly serum from a subject;
    b) testing said sample for the presence of free IL-18 by using the IL-18 antibody of any one of embodiments 14-25 or the IL-18BP of any one of embodiments . . . as capturing molecule and/or testing the said sample for the presence of free IL-18BP by using a first monoclonal IL-18BP specific capturing antibody and an IL-18BP specific detection antibody, which binds to a different site of IL-18BP than the capturing antibody, particularly one of said antibodies binds to the IL-18 binding site of IL-18BP;
    c) determining the amount of free IL-18 and/or free IL-18BP bound to the capturing molecule in the sample;
    d) comparing the amount of free IL-18 and/or free IL-18BP in the sample of the subject suffering from such a disease to the amount in the sample of a healthy subject.

59. A method for diagnosis of the diseases or disorder as defined in any one of embodiments 1-13 and 26-43, for diagnosing a predisposition to the disease or disorder as defined in any one of embodiments 1-13 and 26-43, for monitoring minimal residual disease in a subject, or for predicting responsiveness of a subject to a treatment with IL-18 inhibitor according to embodiments 1-13 and 26-30, the IL-18BP according to embodiments 31-43 or the pharmaceutical composition comprising IL-18 inhibitor according to embodiments 44-49 and a pharmaceutically acceptable carrier and/or excipient according to any one of the preceding embodiments, comprising the steps:
    a) obtaining a sample of body fluid, particularly sputum and serum from a subject;
    b) testing said sample for the presence of free IL-18 by using the IL-18 antibody of embodiments 14-25 or the IL-18BP as capturing molecule and/or testing the said sample for the presence of free IL-18BP by using a first monoclonal IL-18BP specific capturing antibody and an IL-18BP specific detection antibody, which binds to a different site of IL-18BP than the capturing antibody, particularly one of said IL-18BP specific antibodies binds to the IL-18 binding site of IL-18BP;
    c) testing said sample for the presence of total IL-18 total and/or total IL-18BP by using a first monoclonal IL-18BP specific antibody which does not bind to the IL-18 binding site of IL-18BP and a second IL-18 specific antibody, which does not bind to the IL-18BP binding site of IL-18;
    d) determining the amount of free and total IL-18 and/or free and total IL-18BP bound to the capturing molecule in the sample;
    e) comparing the amount of free and/or total IL-18 and/or free and/or total IL-18BP in the sample of the subject suffering from such a disease to the amount in the sample of a healthy subject.

60. The method for diagnosis of any one of the preceding embodiments, wherein the amount of free IL-18 in isolated serum of a subject, particularly a human, suffering from said disease ranges from 5 to 10000 pg/mL, whereas the amount of free IL-18 in serum of healthy subject, particularly a healthy human is ≤4 pg/mL.

61. A set of biomarkers for use in the diagnosis of the diseases or disorder as defined in any one of embodiments 1-13 and 26-43, for use in diagnosing a predisposition to the disease or disorder as defined in any one of embodiments 1-13 and 26-43 or for use in monitoring minimal residual disease in a subject, or for predicting responsiveness of a subject to a treatment with IL-18 inhibitor according to embodiments 1-13 and 26-30, the IL-18BP according to embodiments 31-43 or the pharmaceutical composition comprising IL-18 inhibitor according to embodiments 44-49.

62. A method for diagnosis of the diseases or disorder as defined in any one of embodiments 1-13 and 26-43, for diagnosing a predisposition to the disease or disorder as defined in any one of embodiments 1-13 and 26-43 or for monitoring minimal residual disease in a subject, or for predicting responsiveness of a subject to a treatment with IL-18 inhibitor according to embodiments 1-13 and 26-30, the IL-18BP according to embodiments 31-43 or the pharmaceutical composition comprising IL-18 inhibitor according to embodiments 44-49, comprising the steps:
    e) obtaining a biomarker profile of a subject to be tested by taking a sample of a body fluid from said subject;
    f) obtaining a biomarker profile of a healthy reference population;
    g) obtaining a biomarker profile from a population which suffers from said disease or disorder and
    h) comparing the biomarker profile obtained in step a) with the profile obtained in step b) and step c).

63. A pharmaceutical kit comprising IL-18 inhibitor according to any one of embodiments 1-13 and 26-30, IL-18BP according to embodiments 31-43 or a pharmaceutical composition comprising IL-18 inhibitor according to embodiments 44-49 and a pharmaceutically acceptable carrier and/or excipient according to the invention in separate unit dosage forms, said forms being suitable for administration in effective amounts.

64. A diagnostic kit for detecting free IL-18, comprising an IL-18-specific antibody according to any one of embodiments 14-25 as capturing antibody or the IL-18BP as alternative capturing molecule, and a second IL-18 specific detection antibody or an IL-18-specific antibody according to any one of embodiments 14-25 as detection antibody and a second IL-18 specific capturing antibody, wherein the detection antibody bind to different sites of IL-18 than the capturing molecule.

65. A diagnostic kit for detecting total IL-18 or total IL-18BP, comprising a first monoclonal IL-18BP specific antibody which does not bind to the IL-18 binding site of IL-18BP and a second IL-18 specific antibody, which does not bind to the IL-18BP binding site of IL-18.

66. A diagnostic kit for detecting free IL-18BP, comprising a first monoclonal IL-18BP specific capturing antibody and an IL-18BP specific detection antibody, which binds to a different site of IL-18BP than the capturing antibody.

67. A diagnostic kit, which comprises all diagnostic kits of embodiments 64 to 66.

The invention claimed is:

1. A method of determining the amount of free IL-18 in a sample or in situ comprising detecting the specific binding of IL-18 binding protein (IL-18BP) to free IL-18 protein in the sample or in situ which includes the steps of:
   a) bringing a sample or a specific body part or body area suspected to contain free IL-18 into contact with the IL-18BP, which specifically binds to free IL-18, but not to IL-18 bound in a complex and functions as the capturing molecule for free IL-18;
   b) allowing the IL-18BP to bind to free IL-18;
   c) detecting the binding of IL-18 to the IL-18BP, and determining the amount of free IL-18 in the sample;
   wherein the IL-18 binding protein (IL-18BP) prevents binding of free IL-18 to IL-18 receptor; and
   wherein the IL-18BP is a full length IL-18BP or functional equivalent thereof.

2. The method of claim 1, wherein the IL-18 receptor is IL-18Rα.

3. The method of claim 1, wherein the IL-18BP is SEQ ID NO: 7 or a functional equivalent thereof.

4. The method of claim 1, wherein the IL-18BP is SEQ ID NO: 7.

5. The method of claim 1, wherein the IL-18BP is full length IL-18BP.

* * * * *

UNITED STATES PATENT AND TRADEMARK OFFICE
CERTIFICATE OF CORRECTION

PATENT NO. : 10,858,426 B2
APPLICATION NO. : 14/916917
DATED : December 8, 2020
INVENTOR(S) : Pfeifer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 days.

Signed and Sealed this
Twentieth Day of December, 2022

*Katherine Kelly Vidal*
Director of the United States Patent and Trademark Office

```
                         SEQUENCE LISTING

<160> NUMBER OF SEQ ID NOS: 152

<210> SEQ ID NO 1
<211> LENGTH: 14
<212> TYPE: PRT
<213> ORGANISM: Artificial Sequence
<220> FEATURE:
<223> OTHER INFORMATION: Epitope

<400> SEQUENCE: 1

Tyr Phe Gly Lys Leu Glu Ser Lys Leu Ser Val Ile Arg Asn
1               5                   10

<210> SEQ ID NO 2
<211> LENGTH: 22
<212> TYPE: PRT
<213> ORGANISM: Artificial Sequence
<220> FEATURE:
<223> OTHER INFORMATION: Epitope

<400> SEQUENCE: 2

Phe Ile Ile Ser Met Tyr Lys Asp Ser Gln Pro Arg Gly Met Ala Val
1               5                   10                  15

Thr Thr Ile Ser Val Lys
            20

<210> SEQ ID NO 3
<211> LENGTH: 17
<212> TYPE: PRT
<213> ORGANISM: Artificial Sequence
<220> FEATURE:
<223> OTHER INFORMATION: Epitope

<400> SEQUENCE: 3

Glu Met Asn Pro Pro Asp Asn Ile Lys Asp Thr Lys Ser Asp Ile Ile
1               5                   10                  15

Phe

<210> SEQ ID NO 4
<211> LENGTH: 7
<212> TYPE: PRT
<213> ORGANISM: Artificial Sequence
<220> FEATURE:
<223> OTHER INFORMATION: Epitope

<400> SEQUENCE: 4

Tyr Phe Gly Lys Leu Glu Ser
1               5

<210> SEQ ID NO 5
<211> LENGTH: 10
<212> TYPE: PRT
<213> ORGANISM: Artificial Sequence
<220> FEATURE:
<223> OTHER INFORMATION: Epitope

<400> SEQUENCE: 5

Tyr Lys Asp Ser Gln Pro Arg Gly Met Ala
1               5                   10
```

```
<210> SEQ ID NO 6
<211> LENGTH: 7
<212> TYPE: PRT
<213> ORGANISM: Artificial Sequence
<220> FEATURE:
<223> OTHER INFORMATION: Epitope

<400> SEQUENCE: 6

Asp Asn Ile Lys Asp Thr Lys
1               5

<210> SEQ ID NO 7
<211> LENGTH: 164
<212> TYPE: PRT
<213> ORGANISM: Artificial Sequence
<220> FEATURE:
<223> OTHER INFORMATION: IL-18 binding protein

<400> SEQUENCE: 7

Thr Pro Val Ser Gln Thr Thr Thr Ala Ala Thr Ala Ser Val Arg Ser
1               5                   10                  15

Thr Lys Asp Pro Cys Pro Ser Gln Pro Pro Val Phe Pro Ala Ala Lys
            20                  25                  30

Gln Cys Pro Ala Leu Glu Val Thr Trp Pro Glu Val Glu Val Pro Leu
        35                  40                  45

Asn Gly Thr Leu Ser Leu Ser Cys Val Ala Cys Ser Arg Phe Pro Asn
    50                  55                  60

Phe Ser Ile Leu Tyr Trp Leu Gly Asn Gly Ser Phe Ile Glu His Leu
65                  70                  75                  80

Pro Gly Arg Leu Trp Glu Gly Ser Thr Ser Arg Glu Arg Gly Ser Thr
                85                  90                  95

Gly Thr Gln Leu Cys Lys Ala Leu Val Leu Glu Gln Leu Thr Pro Ala
            100                 105                 110

Leu His Ser Thr Asn Phe Ser Cys Val Leu Val Asp Pro Glu Gln Val
        115                 120                 125

Val Gln Arg His Val Val Leu Ala Gln Leu Trp Ala Gly Leu Arg Ala
    130                 135                 140

Thr Leu Pro Pro Thr Gln Glu Ala Leu Pro Ser Ser His Ser Ser Pro
145                 150                 155                 160

Gln Gln Gln Gly

<210> SEQ ID NO 8
<211> LENGTH: 13
<212> TYPE: PRT
<213> ORGANISM: Artificial Sequence
<220> FEATURE:
<223> OTHER INFORMATION: Linker sequence

<400> SEQUENCE: 8

Glu Phe Gly Ala Gly Leu Val Leu Gly Gly Gln Phe Met
1               5                   10

<210> SEQ ID NO 9
<211> LENGTH: 120
<212> TYPE: PRT
<213> ORGANISM: Artificial Sequence
<220> FEATURE:
<223> OTHER INFORMATION: Antibody 107C6 VH sequence

<400> SEQUENCE: 9

Gln Ile Gln Leu Val Gln Ser Gly Pro Glu Leu Lys Lys Pro Gly Glu
1               5                   10                  15
```

Thr Val Lys Leu Ser Cys Arg Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Ser Gly Val Pro Thr Tyr Ala Asp Asp Phe
    50                  55                  60

Lys Gly Gln Phe Ala Phe Ser Leu Glu Thr Ser Ala Ala Thr Ala Phe
65                  70                  75                  80

Leu Gln Ile Asn Asn Leu Lys Asp Glu Asp Thr Ala Thr Tyr Phe Cys
                85                  90                  95

Ala Arg Glu Gly Tyr Ser Thr Arg Ser Met Asp Tyr Trp Gly Gln
            100                 105                 110

Gly Thr Ser Val Thr Val Ser Ser
            115                 120

<210> SEQ ID NO 10
<211> LENGTH: 112
<212> TYPE: PRT
<213> ORGANISM: Artificial Sequence
<220> FEATURE:
<223> OTHER INFORMATION: Antibody 107C6 VK sequence

<400> SEQUENCE: 10

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asp Ser
            20                  25                  30

Arg Thr Arg Lys Asn Tyr Leu Val Trp Tyr Gln Gln Lys Pro Gly Gln
            35                  40                  45

Ser Pro Lys Leu Leu Ile Tyr Trp Ala Ser Thr Arg Gly Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 11
<211> LENGTH: 120
<212> TYPE: PRT
<213> ORGANISM: Artificial Sequence
<220> FEATURE:
<223> OTHER INFORMATION: Antibody 108F8 VH sequence

<400> SEQUENCE: 11

Gln Ile Gln Leu Val Gln Ser Gly Pro Asp Ser Lys Lys Pro Gly Glu
1               5                   10                  15

Thr Val Lys Leu Ser Cys Arg Ala Ser Gly Tyr Thr Phe Thr Asn Tyr
            20                  25                  30

Gly Met Asn Trp Val Lys Gln Ala Pro Gly Lys Gly Leu Lys Trp Met
            35                  40                  45

Gly Trp Ile Asn Thr Tyr Ser Gly Val Pro Thr Tyr Ala Asp Asp Phe
    50                  55                  60

Lys Gly Gln Phe Ala Phe Ser Leu Glu Thr Ser Ala Ala Thr Ala Phe
65                  70                  75                  80

Leu Gln Ile Asn Asn Leu Lys Asp Glu Asp Thr Ala Thr Tyr Phe Cys

```
                    85                  90                  95

Ala Arg Glu Gly Tyr Ser Thr Thr Arg Ser Met Asp Tyr Trp Gly Gln
                100                 105                 110

Gly Thr Ser Val Thr Val Ser Ser
        115                 120

<210> SEQ ID NO 12
<211> LENGTH: 112
<212> TYPE: PRT
<213> ORGANISM: Artificial Sequence
<220> FEATURE:
<223> OTHER INFORMATION: Antibody 108F8 VK sequence

<400> SEQUENCE: 12

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asp Ser
                20                  25                  30

Arg Thr Arg Lys Asn Tyr Leu Val Trp Tyr Gln Lys Pro Gly Gln
            35                  40                  45

Ser Pro Lys Leu Leu Ile Tyr Trp Ala Ser Thr Arg Gly Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
                100                 105                 110

<210> SEQ ID NO 13
<211> LENGTH: 115
<212> TYPE: PRT
<213> ORGANISM: Artificial Sequence
<220> FEATURE:
<223> OTHER INFORMATION: Antibody 109A6 VH sequence

<400> SEQUENCE: 13

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
                20                  25                  30

Tyr Ile His Trp Val Ile Gln Arg Pro Ala Gln Gly Leu Glu Trp Ile
            35                  40                  45

Gly Arg Ile Asp Pro Ala Asn Gly Asn Thr Ile Tyr Gly Ser Lys Phe
    50                  55                  60

Gln Gly Lys Ala Thr Leu Thr Ala Asp Thr Ser Ser Asn Thr Ala Tyr
65                  70                  75                  80

Ile His Leu Ser Ser Leu Thr Ser Gly Asp Ser Ala Val Tyr Tyr Cys
                85                  90                  95

Ala Gly Tyr Val Trp Phe Ala Tyr Trp Gly Gln Gly Thr Leu Val Thr
                100                 105                 110

Val Ser Ala
        115

<210> SEQ ID NO 14
<211> LENGTH: 112
<212> TYPE: PRT
<213> ORGANISM: Artificial Sequence
<220> FEATURE:
```

<223> OTHER INFORMATION: Antibody 109A6 VK sequence

<400> SEQUENCE: 14

Asp Val Val Met Thr Gln Val Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Phe Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Leu Val Pro Trp Thr Phe Gly Gly Gly Thr Lys Leu Glu Ile Lys
            100                 105                 110

<210> SEQ ID NO 15
<211> LENGTH: 115
<212> TYPE: PRT
<213> ORGANISM: Artificial Sequence
<220> FEATURE:
<223> OTHER INFORMATION: Antibody 111A6 VH sequence

<400> SEQUENCE: 15

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Lys Ile Lys Asp Thr
            20                  25                  30

Tyr Ile His Trp Val Ile Gln Arg Pro Ala Gln Gly Leu Glu Trp Ile
        35                  40                  45

Gly Arg Ile Asp Pro Ala Asn Gly Asn Thr Ile Tyr Gly Ser Lys Phe
    50                  55                  60

Gln Gly Lys Ala Thr Leu Thr Ala Asp Thr Ser Ser Asn Thr Ala Tyr
65                  70                  75                  80

Ile His Leu Ser Ser Leu Thr Ser Gly Asp Ser Ala Val Tyr Tyr Cys
                85                  90                  95

Ala Gly Tyr Val Trp Phe Ala Tyr Trp Gly Gln Gly Thr Leu Val Thr
            100                 105                 110

Val Ser Ala
        115

<210> SEQ ID NO 16
<211> LENGTH: 108
<212> TYPE: PRT
<213> ORGANISM: Artificial Sequence
<220> FEATURE:
<223> OTHER INFORMATION: Antibody 111A6 VK sequence 1

<400> SEQUENCE: 16

Glu Asn Val Leu Thr Gln Ser Pro Ala Ile Met Ser Ala Ser Pro Gly
1               5                   10                  15

Glu Lys Val Thr Met Thr Cys Arg Ala Arg Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Thr Arg Phe Ser

```
                    50                  55                  60
Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
                 85                  90                  95

Leu Thr Phe Gly Ala Gly Thr Lys Leu Glu Leu Lys
            100                 105

<210> SEQ ID NO 17
<211> LENGTH: 112
<212> TYPE: PRT
<213> ORGANISM: Artificial Sequence
<220> FEATURE:
<223> OTHER INFORMATION: Antibody 111A6 VK sequence 2

<400> SEQUENCE: 17

Asp Val Val Met Thr Gln Val Pro Leu Ser Leu Pro Val Ser Leu Gly
 1               5                  10                  15

Asp Gln Ala Ser Ile Ser Cys Arg Ser Ser Gln Arg Leu Val His Ser
                20                  25                  30

Asn Gly Asn Thr Tyr Leu His Trp Phe Leu Gln Lys Pro Gly Gln Ser
            35                  40                  45

Pro Lys Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr Leu Val Pro Trp Thr Phe Gly Gly Gly Thr Lys Leu Glu Ile Lys
            100                 105                 110

<210> SEQ ID NO 18
<211> LENGTH: 115
<212> TYPE: PRT
<213> ORGANISM: Artificial Sequence
<220> FEATURE:
<223> OTHER INFORMATION: Antibody 131B4 VH sequence

<400> SEQUENCE: 18

Glu Val Gln Val Gln Gln Ser Gly Ala Glu Leu Val Lys Pro Gly Ala
 1               5                  10                  15

Ser Val Lys Leu Ser Cys Thr Ala Ser Gly Phe Lys Ile Lys Asp Thr
                20                  25                  30

Tyr Ile His Trp Leu Lys Gln Arg Pro Glu Gln Gly Leu Glu Trp Ile
            35                  40                  45

Gly Arg Ile Asp Pro Ala Asn Gly Asn Thr Ile Tyr Gly Ser Lys Phe
        50                  55                  60

Gln Gly Lys Ala Thr Ile Thr Ala Asp Thr Ser Ser Asn Thr Ala Tyr
 65                  70                  75                  80

Ile Gln Leu Ser Ser Leu Thr Ser Gly Asp Thr Ala Val Tyr Phe Cys
                 85                  90                  95

Ala Gly Tyr Val Trp Phe Ala Tyr Trp Gly Gln Gly Thr Leu Val Thr
            100                 105                 110

Val Ser Ala
        115

<210> SEQ ID NO 19
<211> LENGTH: 112
```

```
<212> TYPE: PRT
<213> ORGANISM: Artificial Sequence
<220> FEATURE:
<223> OTHER INFORMATION: Antibody 131B4 VK sequence

<400> SEQUENCE: 19

Asp Ala Val Leu Thr Gln Thr Pro Leu Ser Leu Pro Val Ser Leu Gly
1               5                   10                  15

Asp Gln Ala Ser Ile Ser Cys Thr Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asp Arg Phe Ser Gly Val Pro
    50                  55                  60

Asp Arg Phe Ser Gly Ser Gly Ser Gly Thr Asp Phe Thr Leu Met Ile
65                  70                  75                  80

Thr Arg Val Glu Ala Glu Asp Leu Gly Val Tyr Phe Cys Ser Gln Ser
                85                  90                  95

Ser Leu Val Pro Trp Thr Phe Gly Gly Gly Thr Lys Leu Glu Val Lys
            100                 105                 110

<210> SEQ ID NO 20
<211> LENGTH: 120
<212> TYPE: PRT
<213> ORGANISM: Artificial Sequence
<220> FEATURE:
<223> OTHER INFORMATION: Antibody 131E8 VH sequence 1

<400> SEQUENCE: 20

Gln Val Gln Leu Lys Gln Ser Arg Pro Gly Pro Val Gln Pro Ser Gln
1               5                   10                  15

Ser Leu Ser Ile Thr Cys Thr Val Ser Gly Phe Ser Leu Pro Asn Tyr
            20                  25                  30

Gly Val His Trp Val Arg Gln Pro Pro Gly Lys Gly Leu Glu Trp Leu
        35                  40                  45

Gly Val Ile Trp Ser Gly Gly Ser Thr Asp Tyr Asn Ala Ala Phe Lys
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Phe Tyr Ser Lys Tyr Asp Tyr Ala Met Asp Tyr Trp Gly Gln
            100                 105                 110

Gly Thr Ser Val Thr Val Ser Ser
        115                 120

<210> SEQ ID NO 21
<211> LENGTH: 113
<212> TYPE: PRT
<213> ORGANISM: Artificial Sequence
<220> FEATURE:
<223> OTHER INFORMATION: Antibody 131E8 VH sequence 2

<400> SEQUENCE: 21

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
```

```
                35                  40                  45
Gly Asn Ile Asn Pro Asn Ser Gly Ser Thr Asn Tyr Asn Glu Lys Phe
 50                      55                  60

Lys Gly Lys Ala Thr Leu Thr Val Asp Thr Ser Ser Thr Ala Tyr
 65                  70                  75                  80

Met Asp Leu Ser Ser Leu Thr Ser Glu Asp Ser Ala Val Tyr Tyr Cys
                 85                  90                  95

Ala Arg Leu Gly Asp Tyr Trp Gly Gln Gly Thr Thr Leu Thr Val Ser
             100                 105                 110

Ser

<210> SEQ ID NO 22
<211> LENGTH: 106
<212> TYPE: PRT
<213> ORGANISM: Artificial Sequence
<220> FEATURE:
<223> OTHER INFORMATION: Antibody 131E8 VK sequence

<400> SEQUENCE: 22

Glu Asn Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
                 20                  25                  30

His Trp Tyr Gln Gln Lys Ser Thr Ser Pro Lys Leu Trp Ile Tyr
             35                  40                  45

Asp Thr Ser Lys Leu Ala Ser Gly Val Pro Gly Arg Phe Ser Gly Ser
 50                      55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Leu Thr
                 85                  90                  95

Phe Gly Ser Gly Thr Lys Leu Glu Ile Lys
             100                 105

<210> SEQ ID NO 23
<211> LENGTH: 120
<212> TYPE: PRT
<213> ORGANISM: Artificial Sequence
<220> FEATURE:
<223> OTHER INFORMATION: Antibody 132H4 VH sequence

<400> SEQUENCE: 23

Glu Val Lys Leu Val Glu Ser Gly Gly Gly Leu Val Lys Pro Gly Gly
 1               5                  10                  15

Ser Leu Lys Leu Ser Cys Ala Ala Ser Gly Phe Thr Phe Ser Asn Tyr
                 20                  25                  30

Ala Met Ser Trp Val Arg Gln Asn Pro Ala Lys Arg Leu Glu Trp Val
             35                  40                  45

Ala Thr Ile Ser Ser Gly Gly Ala Asn Ile Tyr Tyr Pro Asp Ser Val
 50                      55                  60

Lys Gly Arg Phe Ile Ile Ser Arg Asp Asn Ala Arg Asn Thr Leu Tyr
 65                  70                  75                  80

Leu Gln Met Ser Ser Leu Arg Ser Glu Asp Thr Ala Met Tyr Tyr Cys
                 85                  90                  95

Ala Arg Gly Asp Tyr Phe Asn His Phe Trp Phe Ala Tyr Trp Gly Gln
             100                 105                 110

Gly Thr Leu Val Thr Val Ser Ala
```

115                120

<210> SEQ ID NO 24
<211> LENGTH: 112
<212> TYPE: PRT
<213> ORGANISM: Artificial Sequence
<220> FEATURE:
<223> OTHER INFORMATION: Antibody 132H4 VK sequence

<400> SEQUENCE: 24

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 25
<211> LENGTH: 120
<212> TYPE: PRT
<213> ORGANISM: Artificial Sequence
<220> FEATURE:
<223> OTHER INFORMATION: Antibody 133A6 VH sequence

<400> SEQUENCE: 25

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Thr Pro Ala Lys Arg Leu Glu Trp Val
        35                  40                  45

Thr Thr Ile Ser Ser Gly Gly Gly Asn Ile Tyr Tyr Thr Asp Ser Val
    50                  55                  60

Lys Gly Arg Phe Thr Val Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gly Asp Tyr Ser Asn Tyr Phe Trp Phe Ala Tyr Trp Gly Gln
            100                 105                 110

Gly Thr Leu Val Ser Val Ser Glu
        115                 120

<210> SEQ ID NO 26
<211> LENGTH: 112
<212> TYPE: PRT
<213> ORGANISM: Artificial Sequence
<220> FEATURE:
<223> OTHER INFORMATION: Antibody 133A6 VK sequence

<400> SEQUENCE: 26

Asp Val Leu Met Thr Gln Thr Pro Leu Ser Leu Pro Val Ser Leu Gly
1               5                   10                  15

```
Asp Gln Ala Ser Ile Ser Cys Arg Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110
```

<210> SEQ ID NO 27
<211> LENGTH: 8
<212> TYPE: PRT
<213> ORGANISM: Artificial Sequence
<220> FEATURE:
<223> OTHER INFORMATION: Antibody 107C6 VH sequence CDR1

<400> SEQUENCE: 27

```
Gly Tyr Thr Phe Thr Asn Tyr Gly
1               5
```

<210> SEQ ID NO 28
<211> LENGTH: 8
<212> TYPE: PRT
<213> ORGANISM: Artificial Sequence
<220> FEATURE:
<223> OTHER INFORMATION: Antibody 107C6 VH sequence CDR2

<400> SEQUENCE: 28

```
Ile Asn Thr Tyr Ser Gly Val Pro
1               5
```

<210> SEQ ID NO 29
<211> LENGTH: 13
<212> TYPE: PRT
<213> ORGANISM: Artificial Sequence
<220> FEATURE:
<223> OTHER INFORMATION: Antibody 107C6 VH sequence CDR3

<400> SEQUENCE: 29

```
Ala Arg Glu Gly Tyr Ser Thr Thr Arg Ser Met Asp Tyr
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Antibody 107C6 VK sequence CDR1

<400> SEQUENCE: 30

```
Gln Ser Leu Leu Asp Ser Arg Thr Arg Lys Asn Tyr
1               5                   10
```

<210> SEQ ID NO 31
<211> LENGTH: 3
<212> TYPE: PRT
<213> ORGANISM: Artificial Sequence
<220> FEATURE:
<223> OTHER INFORMATION: Antibody 107C6 VK sequence CDR2

```
<400> SEQUENCE: 31

Trp Ala Ser
1

<210> SEQ ID NO 32
<211> LENGTH: 8
<212> TYPE: PRT
<213> ORGANISM: Artificial Sequence
<220> FEATURE:
<223> OTHER INFORMATION: Antibody 107C6 VK sequence CDR3

<400> SEQUENCE: 32

Lys Gln Ser Tyr Asn Leu Arg Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Antibody 108F8 VH sequence CDR1

<400> SEQUENCE: 33

Gly Tyr Thr Phe Thr Asn Tyr Gly
1               5

<210> SEQ ID NO 34
<211> LENGTH: 8
<212> TYPE: PRT
<213> ORGANISM: Artificial Sequence
<220> FEATURE:
<223> OTHER INFORMATION: Antibody 108F8 VH sequence CDR2

<400> SEQUENCE: 34

Ile Asn Thr Tyr Ser Gly Val Pro
1               5

<210> SEQ ID NO 35
<211> LENGTH: 13
<212> TYPE: PRT
<213> ORGANISM: Artificial Sequence
<220> FEATURE:
<223> OTHER INFORMATION: Antibody 108F8 VH sequence CDR3

<400> SEQUENCE: 35

Ala Arg Glu Gly Tyr Ser Thr Thr Arg Ser Met Asp Tyr
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Antibody 108F8 VK sequence CDR1

<400> SEQUENCE: 36

Gln Ser Leu Leu Asp Ser Arg Thr Arg Lys Asn Tyr
1               5                   10

<210> SEQ ID NO 37
<211> LENGTH: 3
<212> TYPE: PRT
<213> ORGANISM: Artificial Sequence
<220> FEATURE:
<223> OTHER INFORMATION: Antibody 108F8 VK sequence CDR2

<400> SEQUENCE: 37
```

Trp Ala Ser
1

<210> SEQ ID NO 38
<211> LENGTH: 8
<212> TYPE: PRT
<213> ORGANISM: Artificial Sequence
<220> FEATURE:
<223> OTHER INFORMATION: Antibody 108F8 VK sequence CDR3

<400> SEQUENCE: 38

Lys Gln Ser Tyr Asn Leu Arg Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Antibody 109A6 VH sequence CDR1

<400> SEQUENCE: 39

Gly Phe Lys Ile Lys Asp Thr Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: Antibody 109A6 VH sequence CDR2

<400> SEQUENCE: 40

Ile Asp Pro Ala Asn Gly Asn Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Antibody 109A6 VH sequence CDR3

<400> SEQUENCE: 41

Ala Gly Tyr Val Trp Phe Ala Tyr
1               5

<210> SEQ ID NO 42
<211> LENGTH: 11
<212> TYPE: PRT
<213> ORGANISM: Artificial Sequence
<220> FEATURE:
<223> OTHER INFORMATION: Antibody 109A6 VK sequence CDR1

<400> SEQUENCE: 42

Gln Arg Leu Val His Ser Asn Gly Asn Thr Tyr
1               5                   10

<210> SEQ ID NO 43
<211> LENGTH: 3
<212> TYPE: PRT
<213> ORGANISM: Artificial Sequence
<220> FEATURE:
<223> OTHER INFORMATION: Antibody 109A6 VK sequence CDR2

<400> SEQUENCE: 43

Thr Val Ser
1

<210> SEQ ID NO 44
<211> LENGTH: 9
<212> TYPE: PRT
<213> ORGANISM: Artificial Sequence
<220> FEATURE:
<223> OTHER INFORMATION: Antibody 109A6 VK sequence CDR3

<400> SEQUENCE: 44

Ser Gln Ser Thr Leu Val Pro Trp Thr
1               5

<210> SEQ ID NO 45
<211> LENGTH: 8
<212> TYPE: PRT
<213> ORGANISM: Artificial Sequence
<220> FEATURE:
<223> OTHER INFORMATION: Antibody 111A6 VH sequence CDR1

<400> SEQUENCE: 45

Gly Phe Lys Ile Lys Asp Thr Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Antibody 111A6 VH sequence CDR2

<400> SEQUENCE: 46

Ile Asp Pro Ala Asn Gly Asn Thr
1               5

<210> SEQ ID NO 47
<211> LENGTH: 8
<212> TYPE: PRT
<213> ORGANISM: Artificial Sequence
<220> FEATURE:
<223> OTHER INFORMATION: Antibody 111A6 VH sequence CDR3

<400> SEQUENCE: 47

Ala Gly Tyr Val Trp Phe Ala Tyr
1               5

<210> SEQ ID NO 48
<211> LENGTH: 7
<212> TYPE: PRT
<213> ORGANISM: Artificial Sequence
<220> FEATURE:
<223> OTHER INFORMATION: Antibody 111A6 VK sequence 1 CDR1

<400> SEQUENCE: 48

Ser Ser Val Ser Ser Ser Tyr
1               5

<210> SEQ ID NO 49
<211> LENGTH: 3
<212> TYPE: PRT
<213> ORGANISM: Artificial Sequence
<220> FEATURE:
<223> OTHER INFORMATION: Antibody 111A6 VK sequence 1 CDR2

<400> SEQUENCE: 49

Ser Thr Ser

```
<210> SEQ ID NO 50
<211> LENGTH: 9
<212> TYPE: PRT
<213> ORGANISM: Artificial Sequence
<220> FEATURE:
<223> OTHER INFORMATION: Antibody 111A6 VK sequence 1 CDR3

<400> SEQUENCE: 50

Gln Gln Tyr Ser Gly Tyr Pro Leu Thr
1               5

<210> SEQ ID NO 51
<211> LENGTH: 11
<212> TYPE: PRT
<213> ORGANISM: Artificial Sequence
<220> FEATURE:
<223> OTHER INFORMATION: Antibody 111A6 VK sequence 2 CDR1

<400> SEQUENCE: 51

Gln Arg Leu Val His Ser Asn Gly Asn Thr Tyr
1               5                   10

<210> SEQ ID NO 52
<211> LENGTH: 3
<212> TYPE: PRT
<213> ORGANISM: Artificial Sequence
<220> FEATURE:
<223> OTHER INFORMATION: Antibody 111A6 VK sequence 2 CDR2

<400> SEQUENCE: 52

Thr Val Ser
1

<210> SEQ ID NO 53
<211> LENGTH: 9
<212> TYPE: PRT
<213> ORGANISM: Artificial Sequence
<220> FEATURE:
<223> OTHER INFORMATION: Antibody 111A6 VK sequence 2 CDR2

<400> SEQUENCE: 53

Ser Gln Ser Thr Leu Val Pro Trp Thr
1               5

<210> SEQ ID NO 54
<211> LENGTH: 8
<212> TYPE: PRT
<213> ORGANISM: Artificial Sequence
<220> FEATURE:
<223> OTHER INFORMATION: Antibody 131B4 VH sequence CDR1

<400> SEQUENCE: 54

Gly Phe Lys Ile Lys Asp Thr Tyr
1               5

<210> SEQ ID NO 55
<211> LENGTH: 8
<212> TYPE: PRT
<213> ORGANISM: Artificial Sequence
<220> FEATURE:
<223> OTHER INFORMATION: Antibody 131B4 VH sequence CDR2

<400> SEQUENCE: 55

Ile Asp Pro Ala Asn Gly Asn Thr
1               5
```

```
<210> SEQ ID NO 56
<211> LENGTH: 8
<212> TYPE: PRT
<213> ORGANISM: Artificial Sequence
<220> FEATURE:
<223> OTHER INFORMATION: Antibody 131B4 VH sequence CDR3

<400> SEQUENCE: 56

Ala Gly Tyr Val Trp Phe Ala Tyr
1               5

<210> SEQ ID NO 57
<211> LENGTH: 11
<212> TYPE: PRT
<213> ORGANISM: Artificial Sequence
<220> FEATURE:
<223> OTHER INFORMATION: Antibody 131B4 VK sequence CDR1

<400> SEQUENCE: 57

Gln Ser Leu Val His Ser Asn Gly Asn Thr Tyr
1               5                   10

<210> SEQ ID NO 58
<211> LENGTH: 3
<212> TYPE: PRT
<213> ORGANISM: Artificial Sequence
<220> FEATURE:
<223> OTHER INFORMATION: Antibody 131B4 VK sequence CDR2

<400> SEQUENCE: 58

Lys Val Ser
1

<210> SEQ ID NO 59
<211> LENGTH: 9
<212> TYPE: PRT
<213> ORGANISM: Artificial Sequence
<220> FEATURE:
<223> OTHER INFORMATION: Antibody 131B4 VK sequence CDR3

<400> SEQUENCE: 59

Ser Gln Ser Ser Leu Val Pro Trp Thr
1               5

<210> SEQ ID NO 60
<211> LENGTH: 8
<212> TYPE: PRT
<213> ORGANISM: Artificial Sequence
<220> FEATURE:
<223> OTHER INFORMATION: Antibody 131E8 VH sequence 1 CDR1

<400> SEQUENCE: 60

Gly Phe Ser Leu Pro Asn Tyr Gly
1               5

<210> SEQ ID NO 61
<211> LENGTH: 7
<212> TYPE: PRT
<213> ORGANISM: Artificial Sequence
<220> FEATURE:
<223> OTHER INFORMATION: Antibody 131E8 VH sequence 1 CDR2

<400> SEQUENCE: 61

Ile Trp Ser Gly Gly Ser Thr
1               5
```

```
<210> SEQ ID NO 62
<211> LENGTH: 14
<212> TYPE: PRT
<213> ORGANISM: Artificial Sequence
<220> FEATURE:
<223> OTHER INFORMATION: Antibody 131E8 VH sequence 1 CDR3

<400> SEQUENCE: 62

Ala Arg Asn Phe Tyr Ser Lys Tyr Asp Tyr Ala Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Antibody 131E8 VH sequence 2 CDR1

<400> SEQUENCE: 63

Gly Tyr Thr Phe Thr Ser Tyr Trp
1               5

<210> SEQ ID NO 64
<211> LENGTH: 8
<212> TYPE: PRT
<213> ORGANISM: Artificial Sequence
<220> FEATURE:
<223> OTHER INFORMATION: Antibody 131E8 VH sequence 2 CDR2

<400> SEQUENCE: 64

Ile Asn Pro Asn Ser Gly Ser Thr
1               5

<210> SEQ ID NO 65
<211> LENGTH: 6
<212> TYPE: PRT
<213> ORGANISM: Artificial Sequence
<220> FEATURE:
<223> OTHER INFORMATION: Antibody 131E8 VH sequence 2 CDR3

<400> SEQUENCE: 65

Ala Arg Leu Gly Asp Tyr
1               5

<210> SEQ ID NO 66
<211> LENGTH: 5
<212> TYPE: PRT
<213> ORGANISM: Artificial Sequence
<220> FEATURE:
<223> OTHER INFORMATION: Antibody 131E8 VK sequence CDR1

<400> SEQUENCE: 66

Ser Ser Val Ser Tyr
1               5

<210> SEQ ID NO 67
<211> LENGTH: 3
<212> TYPE: PRT
<213> ORGANISM: Artificial Sequence
<220> FEATURE:
<223> OTHER INFORMATION: Antibody 131E8 VK sequence CDR2

<400> SEQUENCE: 67

Asp Thr Ser
1
```

<210> SEQ ID NO 68
<211> LENGTH: 9
<212> TYPE: PRT
<213> ORGANISM: Artificial Sequence
<220> FEATURE:
<223> OTHER INFORMATION: Antibody 131E8 VK sequence CDR3

<400> SEQUENCE: 68

Phe Gln Gly Ser Gly Tyr Pro Leu Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Antibody 132H4 VH sequence CDR1

<400> SEQUENCE: 69

Gly Phe Thr Phe Ser Asn Tyr Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Antibody 132H4 VH sequence CDR2

<400> SEQUENCE: 70

Ile Ser Ser Gly Gly Ala Asn Ile
1               5

<210> SEQ ID NO 71
<211> LENGTH: 13
<212> TYPE: PRT
<213> ORGANISM: Artificial Sequence
<220> FEATURE:
<223> OTHER INFORMATION: Antibody 132H4 VH sequence CDR3

<400> SEQUENCE: 71

Ala Arg Gly Asp Tyr Phe Asn His Phe Trp Phe Ala Tyr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Antibody 132H4 VK sequence CDR1

<400> SEQUENCE: 72

Gln Ser Ile Val His Ser Asn Gly Asn Thr Tyr
1               5                   10

<210> SEQ ID NO 73
<211> LENGTH: 3
<212> TYPE: PRT
<213> ORGANISM: Artificial Sequence
<220> FEATURE:
<223> OTHER INFORMATION: Antibody 132H4 VK sequence CDR2

<400> SEQUENCE: 73

Lys Val Ser
1

<210> SEQ ID NO 74

```
<211> LENGTH: 9
<212> TYPE: PRT
<213> ORGANISM: Artificial Sequence
<220> FEATURE:
<223> OTHER INFORMATION: Antibody 132H4 VK sequence CDR3

<400> SEQUENCE: 74

Phe Gln Gly Ser His Val Pro Trp Thr
1               5

<210> SEQ ID NO 75
<211> LENGTH: 8
<212> TYPE: PRT
<213> ORGANISM: Artificial Sequence
<220> FEATURE:
<223> OTHER INFORMATION: Antibody 133A6 VH sequence CDR1

<400> SEQUENCE: 75

Gly Phe Thr Phe Ser Asn Tyr Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Antibody 133A6 VH sequence CDR2

<400> SEQUENCE: 76

Ile Ser Ser Gly Gly Gly Asn Ile
1               5

<210> SEQ ID NO 77
<211> LENGTH: 13
<212> TYPE: PRT
<213> ORGANISM: Artificial Sequence
<220> FEATURE:
<223> OTHER INFORMATION: Antibody 133A6 VH sequence CDR3

<400> SEQUENCE: 77

Ala Arg Gly Asp Tyr Ser Asn Tyr Phe Trp Phe Ala Tyr
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Antibody 133A6 VK sequence CDR1

<400> SEQUENCE: 78

Gln Ser Ile Val His Ser Asn Gly Asn Thr Tyr
1               5                   10

<210> SEQ ID NO 79
<211> LENGTH: 3
<212> TYPE: PRT
<213> ORGANISM: Artificial Sequence
<220> FEATURE:
<223> OTHER INFORMATION: Antibody 133A6 VK sequence CDR2

<400> SEQUENCE: 79

Lys Val Ser
1

<210> SEQ ID NO 80
<211> LENGTH: 9
```

```
<212> TYPE: PRT
<213> ORGANISM: Artificial Sequence
<220> FEATURE:
<223> OTHER INFORMATION: Antibody 133A6 VK sequence CDR3

<400> SEQUENCE: 80

Phe Gln Gly Ser His Val Pro Trp Thr
1               5

<210> SEQ ID NO 81
<211> LENGTH: 453
<212> TYPE: DNA
<213> ORGANISM: Artificial Sequence
<220> FEATURE:
<223> OTHER INFORMATION: Antibody 107C6 VH DNA sequence

<400> SEQUENCE: 81
atgggttggg tgtggacctt gccattcctg atggcagctg cccaaagtat ccaagcacag    60
atccagttgg tgcagtctgg tcctgaactg aagaagcctg gagagacagt caagctctcc   120
tgcagggctt ctggatatac attcacaaac tatggaatga actgggtgaa gcaggctcca   180
ggaaagggtt taaagtggat gggctggata aacacctact ctggagtgcc aacatatgct   240
gatgacttca aggacagttt gccttctct ttggaaacct ctgccgccac tgcctttttg    300
cagatcaaca acctcaaaga tgaggacacg gctacatatt tttgtgcaag agagggatat   360
agtactacca ggtctatgga ctactggggt caaggaacct cagtcaccgt ctcctcagcc   420
aaaacgacac ccccatctgt ctatccactg gcc                                453

<210> SEQ ID NO 82
<211> LENGTH: 151
<212> TYPE: PRT
<213> ORGANISM: Artificial Sequence
<220> FEATURE:
<223> OTHER INFORMATION: Antibody 107C6 VH sequence

<400> SEQUENCE: 82

Met Gly Trp Val Trp Thr Leu Pro Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Leu Ser Cys Arg Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Gln Phe Ala Phe Ser Leu Glu Thr Ser Ala Ala
                85                  90                  95

Thr Ala Phe Leu Gln Ile Asn Asn Leu Lys Asp Glu Asp Thr Ala Thr
            100                 105                 110

Tyr Phe Cys Ala Arg Glu Gly Tyr Ser Thr Thr Arg Ser Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala
145                 150

<210> SEQ ID NO 83
<211> LENGTH: 501
```

<212> TYPE: DNA
<213> ORGANISM: Artificial Sequence
<220> FEATURE:
<223> OTHER INFORMATION: Antibody 107C6 VK DNA sequence

<400> SEQUENCE: 83

| | | | | | |
|---|---|---|---|---|---|
| atggagtcac | agtctcaggt | tcttatattg | ctgctgctat | gggtatctgg | tacctgtggg | 60 |
| gacattgtga | tgtcacagtc | tccatcctcc | ctggctgtgt | cagcaggaga | gaaggtcact | 120 |
| atgagctgca | aatccagtca | gagtctgctc | gacagtagaa | cccgaaagaa | ctacttggtt | 180 |
| tggtaccagc | agaaaccagg | gcagtctcct | aaactgctga | tctactgggc | atccactagg | 240 |
| ggatctgggg | tccctgatcg | cttcacaggc | agtggatctg | gacagattt | cactctcacc | 300 |
| atcagcagtg | tgcaggctga | agacctggca | gtttattact | gcaaacaatc | ttataatctt | 360 |
| cggacgttcg | gtggaggcac | caagctggaa | atcaaacggg | ctgatgctgc | accaactgta | 420 |
| tccatcttcc | caccatccag | tgagcagtta | acatctggag | gtgcctcagt | cgtgtgcttc | 480 |
| ttgaacaact | tctaccccaa | a | | | | 501 |

<210> SEQ ID NO 84
<211> LENGTH: 167
<212> TYPE: PRT
<213> ORGANISM: Artificial Sequence
<220> FEATURE:
<223> OTHER INFORMATION: Antibody 107C6 VK sequence

<400> SEQUENCE: 84

Met Glu Ser Gln Ser Gln Val Leu Ile Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asp Ser Arg Thr Arg Lys Asn Tyr Leu Val Trp Tyr Gln Gln
    50                  55                  60

Lys Pro Gly Gln Ser Pro Lys Leu Leu Ile Tyr Trp Ala Ser Thr Arg
65                  70                  75                  80

Gly Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys
                165

<210> SEQ ID NO 85
<211> LENGTH: 456
<212> TYPE: DNA
<213> ORGANISM: Artificial Sequence
<220> FEATURE:
<223> OTHER INFORMATION: Antibody 108F8 VH sequence

<400> SEQUENCE: 85

| | | | | | |
|---|---|---|---|---|---|
| atgggttggg | tgtggacctt | gctattcctg | atggcagctg | cccaaagtat | ccaatcacag | 60 |

```
atccagttgg tgcagtctgg tcctgattcg aagaagcctg gagagacagt caagctctcc      120
tgcagggctt ctggatatac attcacaaac tatggaatga actgggtgaa gcaggctcca      180
ggaaagggtt taaagtggat gggctggata acacctactc tggagtgcc aacatatgct       240 gatgacttca agggacagtt tgccttctct ttggaaacct ctgccgccac tgccttttg       300 cagatcaaca acctcaaaga tgaggacacg gctacatatt tttgtgcaag agagggatat      360
agtactacca ggtctatgga ctactggggt caaggaacct cagtcaccgt ctcctcagcc      420
aaaacgacac ccccatctgt cttccccctg gcacct                                456
```

<210> SEQ ID NO 86
<211> LENGTH: 152
<212> TYPE: PRT
<213> ORGANISM: Artificial Sequence
<220> FEATURE:
<223> OTHER INFORMATION: Antibody 108F8 VH sequence

<400> SEQUENCE: 86

```
Met Gly Trp Val Trp Thr Leu Leu Phe Leu Met Ala Ala Ala Gln Ser
1               5                   10                  15

Ile Gln Ser Gln Ile Gln Leu Val Gln Ser Gly Pro Asp Ser Lys Lys
            20                  25                  30

Pro Gly Glu Thr Val Lys Leu Ser Cys Arg Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Gln Phe Ala Phe Ser Leu Glu Thr Ser Ala Ala
                85                  90                  95

Thr Ala Phe Leu Gln Ile Asn Asn Leu Lys Asp Glu Asp Thr Ala Thr
            100                 105                 110

Tyr Phe Cys Ala Arg Glu Gly Tyr Ser Thr Thr Arg Ser Met Asp Tyr
        115                 120                 125

Trp Gly Gln Gly Thr Ser Val Thr Val Ser Ser Ala Lys Thr Thr Pro
    130                 135                 140

Pro Ser Val Phe Pro Leu Ala Pro
145                 150
```

<210> SEQ ID NO 87
<211> LENGTH: 510
<212> TYPE: DNA
<213> ORGANISM: Artificial Sequence
<220> FEATURE:
<223> OTHER INFORMATION: Antibody 108F8 VK DNA sequence

<400> SEQUENCE: 87

```
atgggcttca agatgaagtc agtcgacctg gttcttatat tgctgctgct atgggtatct       60
ggtacctgtg gggacattgt gatgtcacag tctccatcct ccctggctgt gtcagcagga     120
gagaaggtca ctatgagctg caaatccagt cagagtctgc tcgacagtag aacccgaaag     180
aactacttgg tttggtacca gcagaaacca gggcagtctc ctaaactgct gatctactgg     240
gcatccacta ggggatctgg ggtccctgat cgcttcacag gcagtggatc tgggacagat     300
ttcactctca ccatcagcag tgtgcaggct gaagacctgg cagttttatta ctgcaaacaa     360 tcttataatc ttcggacgtt cggtggaggc accaagctgg aaatcaaacg ggctgatgct     420
```

```
gcaccaactg tatccatctt cccaccatcc agtgagcagt taacatctgg aggtgcctca    480
gtcgtgtgct tcttgaacaa cttctacccc                                    510
```

<210> SEQ ID NO 88
<211> LENGTH: 170
<212> TYPE: PRT
<213> ORGANISM: Artificial Sequence
<220> FEATURE:
<223> OTHER INFORMATION: Antibody 108F8 VK sequence

<400> SEQUENCE: 88

```
Met Gly Phe Lys Met Lys Ser Val Asp Leu Val Leu Ile Leu Leu Leu
 1               5                  10                  15

Leu Trp Val Ser Gly Thr Cys Gly Asp Ile Val Met Ser Gln Ser Pro
             20                  25                  30

Ser Ser Leu Ala Val Ser Ala Gly Glu Lys Val Thr Met Ser Cys Lys
         35                  40                  45

Ser Ser Gln Ser Leu Leu Asp Ser Arg Thr Arg Lys Asn Tyr Leu Val
     50                  55                  60

Trp Tyr Gln Gln Lys Pro Gly Gln Ser Pro Lys Leu Leu Ile Tyr Trp
 65                  70                  75                  80

Ala Ser Thr Arg Gly Ser Gly Val Pro Asp Arg Phe Thr Gly Ser Gly
                 85                  90                  95

Ser Gly Thr Asp Phe Thr Leu Thr Ile Ser Ser Val Gln Ala Glu Asp
            100                 105                 110

Leu Ala Val Tyr Tyr Cys Lys Gln Ser Tyr Asn Leu Arg Thr Phe Gly
        115                 120                 125

Gly Gly Thr Lys Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro
                165                 170
```

<210> SEQ ID NO 89
<211> LENGTH: 441
<212> TYPE: DNA
<213> ORGANISM: Artificial Sequence
<220> FEATURE:
<223> OTHER INFORMATION: Antibody 109A6 VH DNA sequence

<400> SEQUENCE: 89

```
atgaaatgca gctggattat gttcttcctg atggcagtgg ttacaggggt caattcagag    60
gttcagctgc agcagtctgg ggcagaactt gtgaagccag ggcctcagt caagttgtcc    120 tgcacagctt ctggcttcaa aattaaagac acctatatac actgggtgat ccagaggcct    180
gcacagggcc tggaatggat tggaaggatt gatcctgcga atggtaatac tattatggc    240 tcaaagttcc agggcaaggc cactctaaca gcggacacat catccaacac agcctacatt    300
cacctcagca gcctgacatc tgggactct gccgtctatt actgtgcggg ctacgtttgg    360
tttgcttact ggggccaagg gactctggtc actgtctctg cagctacaac aacagcccca    420
tccgtcttcc ccctggcacc a                                             441
```

<210> SEQ ID NO 90
<211> LENGTH: 147
<212> TYPE: PRT
<213> ORGANISM: Artificial Sequence
<220> FEATURE:

<223> OTHER INFORMATION: Antibody 109A6 VH sequence

<400> SEQUENCE: 90

```
Met Lys Cys Ser Trp Ile Met Phe Phe Leu Met Ala Val Val Thr Gly
1               5                   10                  15
Val Asn Ser Glu Val Gln Leu Gln Gln Ser Gly Ala Glu Leu Val Lys
            20                  25                  30
Pro Gly Ala Ser Val Lys Leu Ser Cys Thr Ala Ser Gly Phe Lys Ile
        35                  40                  45
Lys Asp Thr Tyr Ile His Trp Val Ile Gln Arg Pro Ala Gln Gly Leu
    50                  55                  60
Glu Trp Ile Gly Arg Ile Asp Pro Ala Asn Gly Asn Thr Ile Tyr Gly
65                  70                  75                  80
Ser Lys Phe Gln Gly Lys Ala Thr Leu Thr Ala Asp Thr Ser Ser Asn
                85                  90                  95
Thr Ala Tyr Ile His Leu Ser Ser Leu Thr Ser Gly Asp Ser Ala Val
            100                 105                 110
Tyr Tyr Cys Ala Gly Tyr Val Trp Phe Ala Tyr Trp Gly Gln Gly Thr
        115                 120                 125
Leu Val Thr Val Ser Ala Ala Thr Thr Thr Ala Pro Ser Val Phe Pro
    130                 135                 140
Leu Ala Pro
145
```

<210> SEQ ID NO 91
<211> LENGTH: 498
<212> TYPE: DNA
<213> ORGANISM: Artificial Sequence
<220> FEATURE:
<223> OTHER INFORMATION: Antibody 109A6 VK DNA sequence

<400> SEQUENCE: 91

```
atgaagttgc ctgttaggct gttggtgctg atgttctgga ttcctgcctc cagcagtgat    60
gttgtgatga cccaagttcc actctccctg cctgtcagtc ttggagatca agcctccatc   120
tcttgcagat ctagtcagag acttgtgcac agtaatggaa acacctattt acattggttc   180
ttacagaagc caggccagtc tccaaagctc ctgatctaca cagtttccaa ccgattttct   240
ggggtcccag acaggttcag tggcagtgga tcagggacag atttcacact caagatcagc   300
agagtggagg ctgaggatct gggagtttat ttctgctctc aaagtacact tgttccgtgg   360
acgttcggtg aggcaccaa gctggaaatc aaacgggctg atgctgcacc aactgtatcc   420
atcttcccac catccagtga gcagttaaca tctggaggtg cctcagtcgt gtgcttcttg   480
aacaacttct acccaaag                                                 498
```

<210> SEQ ID NO 92
<211> LENGTH: 166
<212> TYPE: PRT
<213> ORGANISM: Artificial Sequence
<220> FEATURE:
<223> OTHER INFORMATION: Antibody 109A6 VK sequence

<400> SEQUENCE: 92

```
Met Lys Leu Pro Val Arg Leu Leu Val Leu Met Phe Trp Ile Pro Ala
1               5                   10                  15
Ser Ser Ser Asp Val Val Met Thr Gln Val Pro Leu Ser Leu Pro Val
            20                  25                  30
Ser Leu Gly Asp Gln Ala Ser Ile Ser Cys Arg Ser Ser Gln Arg Leu
```

```
            35                  40                  45
Val His Ser Asn Gly Asn Thr Tyr Leu His Trp Phe Leu Gln Lys Pro
 50                  55                  60

Gly Gln Ser Pro Lys Leu Leu Ile Tyr Thr Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr Leu Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165

<210> SEQ ID NO 93
<211> LENGTH: 441
<212> TYPE: DNA
<213> ORGANISM: Artificial Sequence
<220> FEATURE:
<223> OTHER INFORMATION: Antibody 111A6 VH DNA sequence

<400> SEQUENCE: 93
atgaaatgca gctgggttat gttcttcctg atggcagtgg ttacaggggt caattcagag      60
gttcagctgc agcagtctgg ggcagaactt gtgaagccag ggcctcagt caagttgtcc     120 tgcacagctt ctggcttcaa aattaaagac acctatatac actgggtgat ccagaggcct    180
gcacagggcc tggaatggat tggaaggatt gatcctgcga atggtaatac tatttatggc    240
tcaaagttcc agggcaaggc cactctaaca gcggacacat catccaacac agcctacatt    300
cacctcagca gcctgacatc tggggactct gccgtctatt actgtgcggg ctacgtttgg    360
tttgcttact ggggccaagg gactctggtc actgtctctg cagctacaac aacagcccca    420
tccgtcttcc ccctggcacc a                                              441

<210> SEQ ID NO 94
<211> LENGTH: 147
<212> TYPE: PRT
<213> ORGANISM: Artificial Sequence
<220> FEATURE:
<223> OTHER INFORMATION: Antibody 111A6 VH sequence

<400> SEQUENCE: 94

Met Lys Cys Ser Trp Val Met Phe Phe Leu Met Ala Val Val Thr Gly
  1               5                  10                  15

Val Asn Ser Glu Val Gln Leu Gln Gln Ser Gly Ala Glu Leu Val Lys
             20                  25                  30

Pro Gly Ala Ser Val Lys Leu Ser Cys Thr Ala Ser Gly Phe Lys Ile
         35                  40                  45

Lys Asp Thr Tyr Ile His Trp Val Ile Gln Arg Pro Ala Gln Gly Leu
     50                  55                  60

Glu Trp Ile Gly Arg Ile Asp Pro Ala Asn Gly Asn Thr Ile Tyr Gly
65                  70                  75                  80

Ser Lys Phe Gln Gly Lys Ala Thr Leu Thr Ala Asp Thr Ser Ser Asn
                85                  90                  95
```

```
Thr Ala Tyr Ile His Leu Ser Ser Leu Thr Ser Gly Asp Ser Ala Val
            100                 105                 110

Tyr Tyr Cys Ala Gly Tyr Val Trp Phe Ala Tyr Trp Gly Gln Gly Thr
        115                 120                 125

Leu Val Thr Val Ser Ala Ala Thr Thr Thr Ala Pro Ser Val Phe Pro
    130                 135                 140

Leu Ala Pro
145

<210> SEQ ID NO 95
<211> LENGTH: 495
<212> TYPE: DNA
<213> ORGANISM: Artificial Sequence
<220> FEATURE:
<223> OTHER INFORMATION: Antibody 111A6 VK DNA sequence 1

<400> SEQUENCE: 95
atggattttc aggtgcagat tttcagcttc ttgctaatca gtgcctcagt tgcaatgtcc    60
agaggagaaa atgtgctcac ccagtctcca gcaatcatgt ctgcttctcc aggggagaag   120
gtcaccatga cctgcagggc caggtcaagt gtaagttcca gttacttgca ctggtaccag   180
cagaagtcag gtgcctcccc caaactctgg atttatagca catccaactt ggcttctgga   240
gtccctactc gcttcagtgg cagtgggtct gggacctctt actctctcac aatcagcagt   300
gtggaggctg aagatgctgc cacttattac tgccagcagt acagtggtta cccactcacg   360
ttcggtgctg ggaccaagct ggagctgaaa cgggctgatg ctgcaccaac tgtatccatc   420
ttcccaccat ccagtgagca gttaacatct ggaggtgcct cagtcgtgtg cttcttgaac   480
aacttctacc ccaag                                                   495

<210> SEQ ID NO 96
<211> LENGTH: 165
<212> TYPE: PRT
<213> ORGANISM: Artificial Sequence
<220> FEATURE:
<223> OTHER INFORMATION: Antibody 111A6 VK sequence 1

<400> SEQUENCE: 96

Met Asp Phe Gln Val Gln Ile Phe Ser Phe Leu Leu Ile Ser Ala Ser
1               5                   10                  15

Val Ala Met Ser Arg Gly Glu Asn Val Leu Thr Gln Ser Pro Ala Ile
            20                  25                  30

Met Ser Ala Ser Pro Gly Glu Lys Val Thr Met Thr Cys Arg Ala Arg
        35                  40                  45

Ser Ser Val Ser Ser Ser Tyr Leu His Trp Tyr Gln Gln Lys Ser Gly
    50                  55                  60

Ala Ser Pro Lys Leu Trp Ile Tyr Ser Thr Ser Asn Leu Ala Ser Gly
65                  70                  75                  80

Val Pro Thr Arg Phe Ser Gly Ser Gly Ser Gly Thr Ser Tyr Ser Leu
                85                  90                  95

Thr Ile Ser Ser Val Glu Ala Glu Asp Ala Ala Thr Tyr Tyr Cys Gln
            100                 105                 110

Gln Tyr Ser Gly Tyr Pro Leu Thr Phe Gly Ala Gly Thr Lys Leu Glu
        115                 120                 125

Leu Lys Arg Ala Asp Ala Ala Pro Thr Val Ser Ile Phe Pro Pro Ser
    130                 135                 140

Ser Glu Gln Leu Thr Ser Gly Gly Ala Ser Val Val Cys Phe Leu Asn
```

Asn Phe Tyr Pro Lys
                165

<210> SEQ ID NO 97
<211> LENGTH: 499
<212> TYPE: DNA
<213> ORGANISM: Artificial Sequence
<220> FEATURE:
<223> OTHER INFORMATION: Antibody 111A6 VK DNA sequence 2

<400> SEQUENCE: 97

```
atgaagttgc ctgttaggct gttggtgctg atgttctgga ttcctgcctc cagcagtgat      60
gttgtgatga cccaagttcc actctccctg cctgtcagtc ttggagatca agcctccatc     120
tcttgcagat ctagtcagag acttgtgcac agtaatggaa acacctattt acattggttc     180
ttacagaagc caggccagtc tccaaagctc ctgatctaca cagtttccaa ccgattttct     240
ggggtcccag acaggttcag tggcagtgga tcaggacag atttcacact caagatcagc      300
agagtggagg ctgaggatct gggagtttat ttctgctctc aaagtacact tgttccgtgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaag                                                  499
```

<210> SEQ ID NO 98
<211> LENGTH: 166
<212> TYPE: PRT
<213> ORGANISM: Artificial Sequence
<220> FEATURE:
<223> OTHER INFORMATION: Antibody 111A6 VK sequence 2

<400> SEQUENCE: 98

Met Lys Leu Pro Val Arg Leu Leu Val Leu Met Phe Trp Ile Pro Ala
1               5                   10                  15

Ser Ser Ser Asp Val Val Met Thr Gln Val Pro Leu Ser Leu Pro Val
            20                  25                  30

Ser Leu Gly Asp Gln Ala Ser Ile Ser Cys Arg Ser Ser Gln Arg Leu
        35                  40                  45

Val His Ser Asn Gly Asn Thr Tyr Leu His Trp Phe Leu Gln Lys Pro
    50                  55                  60

Gly Gln Ser Pro Lys Leu Leu Ile Tyr Thr Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr Leu Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys
                165

<210> SEQ ID NO 99
<211> LENGTH: 438

```
<212> TYPE: DNA
<213> ORGANISM: Artificial Sequence
<220> FEATURE:
<223> OTHER INFORMATION: Antibody 131B4 VH DNA sequence 1

<400> SEQUENCE: 99
atgaaatgca gctggattat gttcttcctg atggcagtgg ttacaggggt caattcagag      60
gttcaggtgc agcagtctgg ggcagagctt gtgaagccag gggcctcagt caagttgtcc     120
tgcacagctt ctggcttcaa aattaaggac acctatatac actggttaaa acagaggcct     180
gaacagggcc tggaatggat tggaaggatt gatcctgcga atggtaatac tatatatggc     240
tcaaagttcc agggcaaggc cactataaca gcagacacat catccaacac agcctacatt     300
caactcagca gcctgacatc tggggacact gccgtctatt tttgtgcggg ctacgtttgg     360
tttgcttact ggggccaagg gactctggtc actgtctctg cagccaaaac gacaccccca     420
tccgtcttcc ccctggcc                                                    438

<210> SEQ ID NO 100
<211> LENGTH: 146
<212> TYPE: PRT
<213> ORGANISM: Artificial Sequence
<220> FEATURE:
<223> OTHER INFORMATION: Antibody 131B4 VH sequence 1

<400> SEQUENCE: 100

Met Lys Cys Ser Trp Ile Met Phe Phe Leu Met Ala Val Val Thr Gly
1               5                   10                  15

Val Asn Ser Glu Val Gln Val Gln Gln Ser Gly Ala Glu Leu Val Lys
            20                  25                  30

Pro Gly Ala Ser Val Lys Leu Ser Cys Thr Ala Ser Gly Phe Lys Ile
        35                  40                  45

Lys Asp Thr Tyr Ile His Trp Leu Lys Gln Arg Pro Glu Gln Gly Leu
    50                  55                  60

Glu Trp Ile Gly Arg Ile Asp Pro Ala Asn Gly Asn Thr Ile Tyr Gly
65                  70                  75                  80

Ser Lys Phe Gln Gly Lys Ala Thr Ile Thr Ala Asp Thr Ser Ser Asn
                85                  90                  95

Thr Ala Tyr Ile Gln Leu Ser Ser Leu Thr Ser Gly Asp Thr Ala Val
            100                 105                 110

Tyr Phe Cys Ala Gly Tyr Val Trp Phe Ala Tyr Trp Gly Gln Gly Thr
        115                 120                 125

Leu Val Thr Val Ser Ala Ala Lys Thr Thr Pro Pro Ser Val Phe Pro
    130                 135                 140

Leu Ala
145

<210> SEQ ID NO 101
<211> LENGTH: 453
<212> TYPE: DNA
<213> ORGANISM: Artificial Sequence
<220> FEATURE:
<223> OTHER INFORMATION: Antibody 131B4 VH DNA sequence 2

<400> SEQUENCE: 101
atggctgtct tggggctgct cttctgcctg gtgacattcc caagctgtgt cctgtcccag      60
gtgcagctga agcagtcagg acctagccta gtgcagccct cacagagcct gtccataacc     120
tgcacagtct ctggtttctc attaactagc tatggtgtac actgggttcg ccagtctcca     180
```

```
ggaaagggtc tggagtggct gggagtgata tggagaggtg aagcacaga ctacaatgca      240 gctttcatgt ccagactgag catcaccaag acaactcca agagccaagt tttcttaaa       300 atgaacagtc tgcaagctga tgacactgcc atatactact gtgccaaaaa ttgggagtat     360
gatggttact gggggtttgc ttactggggc caagggactc tggtcactgt ctctgcagag     420
agtcagtcct tcccaaatgt cttccccctc gaa                                  453
```

<210> SEQ ID NO 102
<211> LENGTH: 151
<212> TYPE: PRT
<213> ORGANISM: Artificial Sequence
<220> FEATURE:
<223> OTHER INFORMATION: Antibody 131B4 VH sequence 2

<400> SEQUENCE: 102

```
Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Ser Leu Val Gln
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Asn Ala
65                  70                  75                  80

Ala Phe Met Ser Arg Leu Ser Ile Thr Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Lys Asn Trp Glu Tyr Asp Gly Tyr Trp Gly Phe Ala Tyr
        115                 120                 125

Trp Gly Gln Gly Thr Leu Val Thr Val Ser Ala Glu Ser Gln Ser Phe
    130                 135                 140

Pro Asn Val Phe Pro Leu Glu
145                 150
```

<210> SEQ ID NO 103
<211> LENGTH: 120
<212> TYPE: PRT
<213> ORGANISM: Artificial Sequence
<220> FEATURE:
<223> OTHER INFORMATION: Antibody 131B4 VH variable domain sequence 2

<400> SEQUENCE: 103

```
Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Asn Trp Glu Tyr Asp Gly Tyr Trp Gly Phe Ala Tyr Trp Gly Gln
```

Gly Thr Leu Val Thr Val Ser Ala
        115                 120

<210> SEQ ID NO 104
<211> LENGTH: 8
<212> TYPE: PRT
<213> ORGANISM: Artificial Sequence
<220> FEATURE:
<223> OTHER INFORMATION: Antibody 131B4 VH sequence 2 CDR1

<400> SEQUENCE: 104

Gly Phe Ser Leu Thr Ser Tyr Gly
1               5

<210> SEQ ID NO 105
<211> LENGTH: 7
<212> TYPE: PRT
<213> ORGANISM: Artificial Sequence
<220> FEATURE:
<223> OTHER INFORMATION: Antibody 131B4 VH sequence 2 CDR2

<400> SEQUENCE: 105

Ile Trp Arg Gly Gly Ser Thr
1               5

<210> SEQ ID NO 106
<211> LENGTH: 14
<212> TYPE: PRT
<213> ORGANISM: Artificial Sequence
<220> FEATURE:
<223> OTHER INFORMATION: Antibody 131B4 VH sequence 2 CDR3

<400> SEQUENCE: 106

Ala Lys Asn Trp Glu Tyr Asp Gly Tyr Trp Gly Phe Ala Tyr
1               5                   10

<210> SEQ ID NO 107
<211> LENGTH: 417
<212> TYPE: DNA
<213> ORGANISM: Artificial Sequence
<220> FEATURE:
<223> OTHER INFORMATION: Antibody 131B4 VH DNA sequence 3

<400> SEQUENCE: 107
atggcagtgg ttacagggggt caattcagag gttcagctgc agcagtctgg ggctgagctt      60
gtgaggccag ggcctcagt caagttgtcc tgcacagctt ctggctttaa cattaaagac       120
gactatatgc actgggtgaa gcagaggcct gaacagggcc tggagtggat tggaaggatt     180
gatcctgcga atggtaatac taaatatgcc ccgaagttcc aggacaaggc cactataact     240
gcagacacat cctccaacac agcctacctg cagctcagca gcctgacatc tgaggacact     300
gccgtctatt actgtgctag aagctatgat ggttctctgg gggactactg gggccaaggc     360
accactctca cagtctcctc agagagtcag tccttcccaa atgtcttccc cctcgag        417

<210> SEQ ID NO 108
<211> LENGTH: 139
<212> TYPE: PRT
<213> ORGANISM: Artificial Sequence
<220> FEATURE:
<223> OTHER INFORMATION: Antibody 131B4 VH sequence 3

<400> SEQUENCE: 108

Met Ala Val Val Thr Gly Val Asn Ser Glu Val Gln Leu Gln Gln Ser

```
                1               5                  10                  15
            Gly Ala Glu Leu Val Arg Pro Gly Ala Ser Val Lys Leu Ser Cys Thr
                            20                  25                  30

Ala Ser Gly Phe Asn Ile Lys Asp Asp Tyr Met His Trp Val Lys Gln
                            35                  40                  45

Arg Pro Glu Gln Gly Leu Glu Trp Ile Gly Arg Ile Asp Pro Ala Asn
                    50                  55                  60

Gly Asn Thr Lys Tyr Ala Pro Lys Phe Gln Asp Lys Ala Thr Ile Thr
             65                 70                  75                  80

Ala Asp Thr Ser Ser Asn Thr Ala Tyr Leu Gln Leu Ser Ser Leu Thr
                            85                  90                  95

Ser Glu Asp Thr Ala Val Tyr Tyr Cys Ala Arg Ser Tyr Asp Gly Ser
                           100                 105                 110

Leu Gly Asp Tyr Trp Gly Gln Gly Thr Thr Leu Thr Val Ser Ser Glu
                           115                 120                 125

Ser Gln Ser Phe Pro Asn Val Phe Pro Leu Glu
                           130                 135

<210> SEQ ID NO 109
<211> LENGTH: 118
<212> TYPE: PRT
<213> ORGANISM: Artificial Sequence
<220> FEATURE:
<223> OTHER INFORMATION: Antibody 131B4 VH variable domain sequence 3

<400> SEQUENCE: 109

Glu Val Gln Leu Gln Gln Ser Gly Ala Glu Leu Val Arg Pro Gly Ala
             1               5                  10                  15

Ser Val Lys Leu Ser Cys Thr Ala Ser Gly Phe Asn Ile Lys Asp Asp
                            20                  25                  30

Tyr Met His Trp Val Lys Gln Arg Pro Glu Gln Gly Leu Glu Trp Ile
                            35                  40                  45

Gly Arg Ile Asp Pro Ala Asn Gly Asn Thr Lys Tyr Ala Pro Lys Phe
                    50                  55                  60

Gln Asp Lys Ala Thr Ile Thr Ala Asp Thr Ser Ser Asn Thr Ala Tyr
             65                 70                  75                  80

Leu Gln Leu Ser Ser Leu Thr Ser Glu Asp Thr Ala Val Tyr Tyr Cys
                            85                  90                  95

Ala Arg Ser Tyr Asp Gly Ser Leu Gly Asp Tyr Trp Gly Gln Gly Thr
                           100                 105                 110

Thr Leu Thr Val Ser Ser
                           115

<210> SEQ ID NO 110
<211> LENGTH: 8
<212> TYPE: PRT
<213> ORGANISM: Artificial Sequence
<220> FEATURE:
<223> OTHER INFORMATION: Antibody 131B4 VH sequence 3 CDR1

<400> SEQUENCE: 110

Gly Phe Asn Ile Lys Asp Asp Tyr
             1               5

<210> SEQ ID NO 111
<211> LENGTH: 8
<212> TYPE: PRT
<213> ORGANISM: Artificial Sequence
<220> FEATURE:
```

<223> OTHER INFORMATION: Antibody 131B4 VH sequence 3 CDR2

<400> SEQUENCE: 111

Ile Asp Pro Ala Asn Gly Asn Thr
1               5

<210> SEQ ID NO 112
<211> LENGTH: 11
<212> TYPE: PRT
<213> ORGANISM: Artificial Sequence
<220> FEATURE:
<223> OTHER INFORMATION: Antibody 131B4 VH sequence 3 CDR3

<400> SEQUENCE: 112

Ala Arg Ser Tyr Asp Gly Ser Leu Gly Asp Tyr
1               5                   10

<210> SEQ ID NO 113
<211> LENGTH: 498
<212> TYPE: DNA
<213> ORGANISM: Artificial Sequence
<220> FEATURE:
<223> OTHER INFORMATION: Antibody 131B4 VK DNA sequence

<400> SEQUENCE: 113

```
atgaagttgc ctgttaggct gttggtgctg atgttctgga ttcctgcttc cagcagtgat      60
gctgtgttga cccaaactcc actctccctg cctgtcagtc ttggagatca agcctccatc     120
tcttgcacat ctagtcagag ccttgtacac agtaatggaa acacctattt acattggtac     180
ctgcagaagc caggccagtc tccaaagctc ctgatctaca agtttccga ccgatttttct     240
ggggtcccag acaggttcag tggcagtgga tcaggaacag atttcacact catgatcacc     300
agagtggagg ctgaggatct gggagtttat ttctgctctc aaagttcact tgttccgtgg     360
acgttcggtg aggcaccaa gctggaagtc aaacgggctg atgctgcacc aactgtatcc     420
atcttcccac catccagtga gcagttaaca tctggaggtg cctcagtcgt gtgcttcttg     480
aacaacttct accccaaa                                                   498
```

<210> SEQ ID NO 114
<211> LENGTH: 166
<212> TYPE: PRT
<213> ORGANISM: Artificial Sequence
<220> FEATURE:
<223> OTHER INFORMATION: Antibody 131B4 VK sequence

<400> SEQUENCE: 114

Met Lys Leu Pro Val Arg Leu Leu Val Leu Met Phe Trp Ile Pro Ala
1               5                   10                  15

Ser Ser Ser Asp Ala Val Leu Thr Gln Thr Pro Leu Ser Leu Pro Val
            20                  25                  30

Ser Leu Gly Asp Gln Ala Ser Ile Ser Cys Thr Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asp Arg Phe Ser
65                  70                  75                  80

Gly Val Pro Asp Arg Phe Ser Gly Ser Gly Ser Gly Thr Asp Phe Thr
                85                  90                  95

Leu Met Ile Thr Arg Val Glu Ala Glu Asp Leu Gly Val Tyr Phe Cys
            100                 105                 110

```
Ser Gln Ser Ser Leu Val Pro Trp Thr Phe Gly Gly Thr Lys Leu
        115                 120                 125

Glu Val Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145             150                 155                     160

Asn Asn Phe Tyr Pro Lys
                165

<210> SEQ ID NO 115
<211> LENGTH: 452
<212> TYPE: DNA
<213> ORGANISM: Artificial Sequence
<220> FEATURE:
<223> OTHER INFORMATION: Antibody 131E8 VH DNA sequence 1

<400> SEQUENCE: 115
atggctgttt tggggctgct cttctgcctg gtgacattcc caagctgtgt cctatcccag    60
gtgcagctga agcagtcaag acctggccca gtgcagccct cacagagcct gtccatcacc   120
tgcacagtct ctggtttctc attacctaac tatggtgtac actgggttcg ccagcctcca   180
ggaaagggtc tggagtggct gggagtgata tggagtggtg aagcacaga ctataatgca    240 gctttcaaat ccagactgag catcagcaag acaactcca agagccaagt tttctttaaa    300
atgaacagtc tgcaagctga tgacacagcc atatactact gtgccagaaa tttttatagt   360
aagtacgact atgctatgga ctactggggt caaggaacct cagtcaccgt ctcctcagcc   420
aaaacaacac cccatccgt cttccccctg gc                                   452

<210> SEQ ID NO 116
<211> LENGTH: 150
<212> TYPE: PRT
<213> ORGANISM: Artificial Sequence
<220> FEATURE:
<223> OTHER INFORMATION: Antibody 131E8 VH sequence 1

<400> SEQUENCE: 116

Met Ala Val Leu Gly Leu Leu Phe Cys Leu Val Thr Phe Pro Ser Cys
1               5                   10                  15

Val Leu Ser Gln Val Gln Leu Lys Gln Ser Arg Pro Gly Pro Val Gln
            20                  25                  30

Pro Ser Gln Ser Leu Ser Ile Thr Cys Thr Val Ser Gly Phe Ser Leu
        35                  40                  45

Pro Asn Tyr Gly Val His Trp Val Arg Gln Pro Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Lys Ser Arg Leu Ser Ile Ser Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Arg Asn Phe Tyr Ser Lys Tyr Asp Tyr Ala Met Asp Tyr
        115                 120                 125

Trp Gly Gln Gly Thr Ser Val Thr Val Ser Ser Ala Lys Thr Thr Pro
    130                 135                 140

Pro Ser Val Phe Pro Leu
145                 150
```

```
<210> SEQ ID NO 117
<211> LENGTH: 411
<212> TYPE: DNA
<213> ORGANISM: Artificial Sequence
<220> FEATURE:
<223> OTHER INFORMATION: Antibody 131E8 VH DNA sequence 2

<400> SEQUENCE: 117
atgttcttct tggtagcaac agctacaggt gtccactccc aggtccaact gcagcagcct     60
gggtctgtgc tggtgaggcc tggagcttca gtgaagctgt cctgcaaggc ttctggctac    120
acattcacca gctactggat gcactgggtg aagcagaggc cgggacaagg ccttgagtgg    180
attggaaata ttaatcctaa tagtggtagt actaactaca tgagaagtt caagggcaag     240 gccacactga ctgtagacac atcctccagc acagcctaca tggatctcag cagcctgaca    300
tctgaggact ctgcggtcta ttactgtgca agactggggtg actactgggg ccaaggcacc    360
actctcacag tctcctcaaa gagtcagtcc tccccatccg tcttccccct g             411

<210> SEQ ID NO 118
<211> LENGTH: 137
<212> TYPE: PRT
<213> ORGANISM: Artificial Sequence
<220> FEATURE:
<223> OTHER INFORMATION: Antibody 131E8 VH sequence 2

<400> SEQUENCE: 118

Met Phe Phe Leu Val Ala Thr Ala Thr Gly Val His Ser Gln Val Gln
1               5                   10                  15

Leu Gln Gln Pro Gly Ser Val Leu Val Arg Pro Gly Ala Ser Val Lys
            20                  25                  30

Leu Ser Cys Lys Ala Ser Gly Tyr Thr Phe Thr Ser Tyr Trp Met His
        35                  40                  45

Trp Val Lys Gln Arg Pro Gly Gln Gly Leu Glu Trp Ile Gly Asn Ile
    50                  55                  60

Asn Pro Asn Ser Gly Ser Thr Asn Tyr Asn Glu Lys Phe Lys Gly Lys
65                  70                  75                  80

Ala Thr Leu Thr Val Asp Thr Ser Ser Thr Ala Tyr Met Asp Leu
                85                  90                  95

Ser Ser Leu Thr Ser Glu Asp Ser Ala Val Tyr Tyr Cys Ala Arg Leu
            100                 105                 110

Gly Asp Tyr Trp Gly Gln Gly Thr Thr Leu Thr Val Ser Ser Lys Ser
        115                 120                 125

Gln Ser Ser Pro Ser Val Phe Pro Leu
    130                 135

<210> SEQ ID NO 119
<211> LENGTH: 435
<212> TYPE: DNA
<213> ORGANISM: Artificial Sequence
<220> FEATURE:
<223> OTHER INFORMATION: Antibody 131E8 VH DNA sequence 3

<400> SEQUENCE: 119
gctgtcttgg ggctgctctt ctgcctggtt gcatttccaa gctgtgtcct gtcccaggtg     60
cagctgaagg agtcaggacc tggcctggtg gcgccctcac agagcctgtc catcacttgc    120
actgtctctg ggttttcatt aaccagctat ggtgtacact gggttcgcca gcctccagga    180
aagggtctgg agtggctggg agtaatatgg gctggtggaa gcacaaatta taattcggct    240
ctcatgtcca gactgagcat cagcaaagac aactccaaga gccaagtttt cttaaaaatg    300
```

-continued

```
aacagtctgc aaactgatga cacagccatg tactactgtg ccagagatag taactacttt    360
gactactggg gccaaggcac cactctcaca gtctcctcag agagtcagtc cttcccaaat    420
gtcttccccc tcgta                                                     435
```

<210> SEQ ID NO 120
<211> LENGTH: 145
<212> TYPE: PRT
<213> ORGANISM: Artificial Sequence
<220> FEATURE:
<223> OTHER INFORMATION: Antibody 131E8 VH sequence 3

<400> SEQUENCE: 120

```
Ala Val Leu Gly Leu Leu Phe Cys Leu Val Ala Phe Pro Ser Cys Val
1               5                   10                  15

Leu Ser Gln Val Gln Leu Lys Glu Ser Gly Pro Gly Leu Val Ala Pro
            20                  25                  30

Ser Gln Ser Leu Ser Ile Thr Cys Thr Val Ser Gly Phe Ser Leu Thr
        35                  40                  45

Ser Tyr Gly Val His Trp Val Arg Gln Pro Pro Gly Lys Gly Leu Glu
    50                  55                  60

Trp Leu Gly Val Ile Trp Ala Gly Gly Ser Thr Asn Tyr Asn Ser Ala
65                  70                  75                  80

Leu Met Ser Arg Leu Ser Ile Ser Lys Asp Asn Ser Lys Ser Gln Val
                85                  90                  95

Phe Leu Lys Met Asn Ser Leu Gln Thr Asp Asp Thr Ala Met Tyr Tyr
            100                 105                 110

Cys Ala Arg Asp Ser Asn Tyr Phe Asp Tyr Trp Gly Gln Gly Thr Thr
        115                 120                 125

Leu Thr Val Ser Ser Glu Ser Gln Ser Phe Pro Asn Val Phe Pro Leu
    130                 135                 140

Val
145
```

<210> SEQ ID NO 121
<211> LENGTH: 115
<212> TYPE: PRT
<213> ORGANISM: Artificial Sequence
<220> FEATURE:
<223> OTHER INFORMATION: Antibody 131E8 VH variable domain sequence 3

<400> SEQUENCE: 121

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asp Ser Asn Tyr Phe Asp Tyr Trp Gly Gln Gly Thr Thr Leu Thr
            100                 105                 110

Val Ser Ser
```

<210> SEQ ID NO 122
<211> LENGTH: 8
<212> TYPE: PRT
<213> ORGANISM: Artificial Sequence
<220> FEATURE:
<223> OTHER INFORMATION: Antibody 131E8 VH sequence 3 CDR1

<400> SEQUENCE: 122

Gly Phe Ser Leu Thr Ser Tyr Gly
1               5

<210> SEQ ID NO 123
<211> LENGTH: 7
<212> TYPE: PRT
<213> ORGANISM: Artificial Sequence
<220> FEATURE:
<223> OTHER INFORMATION: Antibody 131E8 VH sequence 3 CDR2

<400> SEQUENCE: 123

Ile Trp Ala Gly Gly Ser Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Antibody 131E8 VH sequence 3 CDR3

<400> SEQUENCE: 124

Ala Arg Asp Ser Asn Tyr Phe Asp Tyr
1               5

<210> SEQ ID NO 125
<211> LENGTH: 489
<212> TYPE: DNA
<213> ORGANISM: Artificial Sequence
<220> FEATURE:
<223> OTHER INFORMATION: Antibody 131E8 VK DNA sequence

<400> SEQUENCE: 125
atggattttc aggtgcagat tttcagcttc ctgctaatca gtgcctcagt cataatgtcc      60
agaggagaaa atgttctcac ccagtctcca gcaatcatgt ctgcatctcc aggggaaaag    120
gtcaccatga cctgcagtgc cagctcaagt gtaagttaca tgcactggta ccagcagaag    180
tcaagcacct cccccaaact ctggatttat gacacatcca aactggcttc tggagtccca    240
ggtcgcttca gtggcagtgg gtctgggaaa tcttactctc tcacgatcag cagcatggag    300
gctgaagatg ttgccactta ttactgtttt caggggagtg gtacccact cacgttcggc     360 tcggggacaa agttggaaat aaaacgggct gatgctgcac caactgtatc catcttccca    420
ccatccagtg agcagttaac atctggaggt gcctcagtcg tgtgcttctt gaacaacttc    480
taccccaaa                                                            489

<210> SEQ ID NO 126
<211> LENGTH: 163
<212> TYPE: PRT
<213> ORGANISM: Artificial Sequence
<220> FEATURE:
<223> OTHER INFORMATION: Antibody 131E8 VK sequence

<400> SEQUENCE: 126

Met Asp Phe Gln Val Gln Ile Phe Ser Phe Leu Leu Ile Ser Ala Ser
1               5                   10                  15

Val Ile Met Ser Arg Gly Glu Asn Val Leu Thr Gln Ser Pro Ala Ile
            20                  25                  30

Met Ser Ala Ser Pro Gly Glu Lys Val Thr Met Thr Cys Ser Ala Ser
            35                  40                  45

Ser Ser Val Ser Tyr Met His Trp Tyr Gln Gln Lys Ser Ser Thr Ser
    50                  55                  60

Pro Lys Leu Trp Ile Tyr Asp Thr Ser Lys Leu Ala Ser Gly Val Pro
65                  70                  75                  80

Gly Arg Phe Ser Gly Ser Gly Ser Gly Asn Ser Tyr Ser Leu Thr Ile
                85                  90                  95

Ser Ser Met Glu Ala Glu Asp Val Ala Thr Tyr Tyr Cys Phe Gln Gly
            100                 105                 110

Ser Gly Tyr Pro Leu Thr Phe Gly Ser Gly Thr Lys Leu Glu Ile Lys
            115                 120                 125

Arg Ala Asp Ala Ala Pro Thr Val Ser Ile Phe Pro Pro Ser Ser Glu
            130                 135                 140

Gln Leu Thr Ser Gly Gly Ala Ser Val Val Cys Phe Leu Asn Asn Phe
145                 150                 155                 160

Tyr Pro Lys

<210> SEQ ID NO 127
<211> LENGTH: 453
<212> TYPE: DNA
<213> ORGANISM: Artificial Sequence
<220> FEATURE:
<223> OTHER INFORMATION: Antibody 131H1 VH DNA sequence

<400> SEQUENCE: 127
atggctgtct tggggctgct cttctgcctg gtgacattcc caagctgtgt cctatcccag    60
gtgcagctga agcagtcagg acctggccta gtgcagccct cacagagcct gtccatcacc   120
tgcacagtct ctggtttctc attaactagc tatggtgtac actgggttcg ccagtctcca   180
ggaaagggtc tggagtggct gggagtgata tggagtggtg aagcacaga ctataatgca    240 gctttcatat ccagactgag catcagcaag acaattcca agagccaagt tttctttaaa    300
atgaacagtc tgcaagctga tgacacagcc atatattact gtgccagatc ttatgattac   360
gacgggaggg gttactttga ctactggggc caaggcacca ctctcacagt ctcctcagag   420
agtcagtcct tcccaaatgt cttccccctc gta                                453

<210> SEQ ID NO 128
<211> LENGTH: 151
<212> TYPE: PRT
<213> ORGANISM: Artificial Sequence
<220> FEATURE:
<223> OTHER INFORMATION: Antibody 131H1 VH sequence

<400> SEQUENCE: 128

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
            35                  40                  45

Thr Ser Tyr Gly Val His Trp Val Arg Gln Ser Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Ser Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Arg Ser Tyr Asp Tyr Asp Gly Arg Gly Tyr Phe Asp Tyr
                115                 120                 125

Trp Gly Gln Gly Thr Thr Leu Thr Val Ser Ser Glu Ser Gln Ser Phe
        130                 135                 140

Pro Asn Val Phe Pro Leu Val
145                 150

<210> SEQ ID NO 129
<211> LENGTH: 120
<212> TYPE: PRT
<213> ORGANISM: Artificial Sequence
<220> FEATURE:
<223> OTHER INFORMATION: Antibody 131H1 VH variable domain sequence

<400> SEQUENCE: 129

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
            35                  40                  45

Gly Val Ile Trp Ser Gly Gly Ser Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Ser Tyr Asp Tyr Asp Gly Arg Gly Tyr Phe Asp Tyr Trp Gly Gln
                100                 105                 110

Gly Thr Thr Leu Thr Val Ser Ser
            115                 120

<210> SEQ ID NO 130
<211> LENGTH: 8
<212> TYPE: PRT
<213> ORGANISM: Artificial Sequence
<220> FEATURE:
<223> OTHER INFORMATION: Antibody 131H1 VH sequence CDR1

<400> SEQUENCE: 130

Gly Phe Ser Leu Thr Ser Tyr Gly
1               5

<210> SEQ ID NO 131
<211> LENGTH: 7
<212> TYPE: PRT
<213> ORGANISM: Artificial Sequence
<220> FEATURE:
<223> OTHER INFORMATION: Antibody 131H1 VH sequence CDR2

<400> SEQUENCE: 131

Ile Trp Ser Gly Gly Ser Thr
1               5

<210> SEQ ID NO 132
<211> LENGTH: 14
<212> TYPE: PRT
<213> ORGANISM: Artificial Sequence
<220> FEATURE:
<223> OTHER INFORMATION: Antibody 131H1 VH sequence CDR3

<400> SEQUENCE: 132

```
Ala Arg Ser Tyr Asp Tyr Asp Gly Arg Gly Tyr Phe Asp Tyr
1               5                   10
```

<210> SEQ ID NO 133
<211> LENGTH: 486
<212> TYPE: DNA
<213> ORGANISM: Artificial Sequence
<220> FEATURE:
<223> OTHER INFORMATION: Antibody 131H1 VK DNA sequence 1

<400> SEQUENCE: 133

```
atgagtgtgc tcactcaggt cctggggttg ctgctgctgt ggcttacagg tgccagatgt      60
gacatccaga tgactcagtc tccagcctcc ctgtctgcat ctgtgggaga aactgtcacc     120
atcacatgtc gagcaagtga aaatgtttac agatatttag catggtatca gcagagacag     180
ggaaaatctc ctcagctcct ggtctatagt gcaaaaacct tagcagaagg tgtgccatca     240
aggttcagtg gcagtggatc aggcacacag ttttctctga agatcaacac cctgcagcct     300
gaagattttg ggacttatta ctgtcaacat cattataata ctcctctcac gttcggtgct     360
gggaccaagc tggagctgaa acgggctgat gctgcaccaa ctgtatccat cttcccacca     420
tccagtgagc agttaacatc tggaggtgcc tcagtcgtgt gcttcttgaa caacttctac     480
cccaaa                                                                486
```

<210> SEQ ID NO 134
<211> LENGTH: 162
<212> TYPE: PRT
<213> ORGANISM: Artificial Sequence
<220> FEATURE:
<223> OTHER INFORMATION: Antibody 131H1 VK sequence 1

<400> SEQUENCE: 134

```
Met Ser Val Leu Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Glu Asn
            35                  40                  45

Val Tyr Arg Tyr Leu Ala Trp Tyr Gln Gln Arg Gln Gly Lys Ser Pro
        50                  55                  60

Gln Leu Leu Val Tyr Ser Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Thr Leu Gln Pro Glu Asp Phe Gly Thr Tyr Tyr Cys Gln His His Tyr
            100                 105                 110

Asn Thr Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
```

```
                    145                 150                 155                 160
Pro Lys

<210> SEQ ID NO 135
<211> LENGTH: 107
<212> TYPE: PRT
<213> ORGANISM: Artificial Sequence
<220> FEATURE:
<223> OTHER INFORMATION: Antibody 131H1 VK variable domain sequence 1

<400> SEQUENCE: 135

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Val Tyr Arg Tyr
            20                  25                  30

Leu Ala Trp Tyr Gln Gln Arg Gln Gly Lys Ser Pro Gln Leu Leu Val
        35                  40                  45

Tyr Ser Ala Lys Thr Leu Ala Glu Gly Val Pro Ser Arg Phe Ser Gly
    50                  55                  60

Ser Gly Ser Gly Thr Gln Phe Ser Leu Lys Ile Asn Thr Leu Gln Pro
65                  70                  75                  80

Glu Asp Phe Gly Thr Tyr Tyr Cys Gln His His Tyr Asn Thr Pro Leu
                85                  90                  95

Thr Phe Gly Ala Gly Thr Lys Leu Glu Leu Lys
            100                 105

<210> SEQ ID NO 136
<211> LENGTH: 6
<212> TYPE: PRT
<213> ORGANISM: Artificial Sequence
<220> FEATURE:
<223> OTHER INFORMATION: Antibody 131H1 VK sequence 1 CDR1

<400> SEQUENCE: 136

Glu Asn Val Tyr Arg Tyr
1               5

<210> SEQ ID NO 137
<211> LENGTH: 3
<212> TYPE: PRT
<213> ORGANISM: Artificial Sequence
<220> FEATURE:
<223> OTHER INFORMATION: Antibody 131H1 VK sequence 1 CDR2

<400> SEQUENCE: 137

Ser Ala Lys
1

<210> SEQ ID NO 138
<211> LENGTH: 9
<212> TYPE: PRT
<213> ORGANISM: Artificial Sequence
<220> FEATURE:
<223> OTHER INFORMATION: Antibody 131H1 VK sequence 1 CDR3

<400> SEQUENCE: 138

Gln His His Tyr Asn Thr Pro Leu Thr
1               5

<210> SEQ ID NO 139
<211> LENGTH: 486
<212> TYPE: DNA
<213> ORGANISM: Artificial Sequence
```

```
<220> FEATURE:
<223> OTHER INFORMATION: Antibody 131H1 VK DNA sequence 2

<400> SEQUENCE: 139
atggttctta tatggctcct gctatgggta tctggtacct gtggggacat tgtgatgtca      60
cagtctccat cctccctggc tgtgtcagca ggagagaagg tcactatgag ctgcaaatcc     120
agtcagagtc tgttcaacag taaaacccga agaactact tggcttggtt tcagcaaaaa      180
ccagggcagt ctcctgaact gctgatctac tgggcatcca ctaggaaatc tggggtccct     240
gatcgcttca caggcagtgg atctgggaca gatttcactc tcaccatcag cagtgtgcag     300
gctgaagacc tggcagttta ttactgcaag caatcttata atctgtggac gttcggcgga     360
ggcaccaagc tggaaatcaa acgggctgat gctgcaccaa ctgtatccat cttcccacca     420
tccagtgagc agttaacatc tggaggtgcc tcagtcgtgt gcttcttgaa caacttctac     480
cccaaa                                                                486

<210> SEQ ID NO 140
<211> LENGTH: 162
<212> TYPE: PRT
<213> ORGANISM: Artificial Sequence
<220> FEATURE:
<223> OTHER INFORMATION: Antibody 131H1 VK sequence 2

<400> SEQUENCE: 140

Met Val Leu Ile Trp Leu Leu Leu Trp Val Ser Gly Thr Cys Gly Asp
1               5                   10                  15

Ile Val Met Ser Gln Ser Pro Ser Ser Leu Ala Val Ser Ala Gly Glu
            20                  25                  30

Lys Val Thr Met Ser Cys Lys Ser Ser Gln Ser Leu Phe Asn Ser Lys
        35                  40                  45

Thr Arg Lys Asn Tyr Leu Ala Trp Phe Gln Gln Lys Pro Gly Gln Ser
    50                  55                  60

Pro Glu Leu Leu Ile Tyr Trp Ala Ser Thr Arg Lys Ser Gly Val Pro
65                  70                  75                  80

Asp Arg Phe Thr Gly Ser Gly Ser Gly Thr Asp Phe Thr Leu Thr Ile
                85                  90                  95

Ser Ser Val Gln Ala Glu Asp Leu Ala Val Tyr Tyr Cys Lys Gln Ser
            100                 105                 110

Tyr Asn Leu Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys

<210> SEQ ID NO 141
<211> LENGTH: 112
<212> TYPE: PRT
<213> ORGANISM: Artificial Sequence
<220> FEATURE:
<223> OTHER INFORMATION: Antibody 131H1 VK variable domain sequence 2

<400> SEQUENCE: 141

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
```

```
            20                  25                  30

Lys Thr Arg Lys Asn Tyr Leu Ala Trp Phe Gln Gln Lys Pro Gly Gln
            35                  40                  45

Ser Pro Glu Leu Leu Ile Tyr Trp Ala Ser Thr Arg Lys Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Trp Thr Phe Gly Gly Gly Thr Lys Leu Glu Ile Lys
            100                 105                 110
```

<210> SEQ ID NO 142
<211> LENGTH: 12
<212> TYPE: PRT
<213> ORGANISM: Artificial Sequence
<220> FEATURE:
<223> OTHER INFORMATION: Antibody 131H1 VK sequence 2 CDR1

<400> SEQUENCE: 142

```
Gln Ser Leu Phe Asn Ser Lys Thr Arg Lys Asn Tyr
1               5                   10
```

<210> SEQ ID NO 143
<211> LENGTH: 3
<212> TYPE: PRT
<213> ORGANISM: Artificial Sequence
<220> FEATURE:
<223> OTHER INFORMATION: Antibody 131H1 VK sequence 2 CDR2

<400> SEQUENCE: 143

```
Trp Ala Ser
1
```

<210> SEQ ID NO 144
<211> LENGTH: 8
<212> TYPE: PRT
<213> ORGANISM: Artificial Sequence
<220> FEATURE:
<223> OTHER INFORMATION: Antibody 131H1 VK sequence 2 CDR3

<400> SEQUENCE: 144

```
Lys Gln Ser Tyr Asn Leu Trp Thr
1               5
```

<210> SEQ ID NO 145
<211> LENGTH: 440
<212> TYPE: DNA
<213> ORGANISM: Artificial Sequence
<220> FEATURE:
<223> OTHER INFORMATION: Antibody 132H4 VH DNA sequence

<400> SEQUENCE: 145

```
tgagctgggt tttccttgtc cttatttta  aaggtgtcca gtgtgaagtg aagctggtgg      60
agtctggggg aggcttagtg aagcctggag ggtccctgaa actctcctgt gcagcctctg     120
gattcacttt cagtaactat gccatgtctt gggttcgcca gaatccggcg aagaggctgg     180
agtgggtcgc aaccattagt agtggtggtg ctaatattta ctatccagac agtgtgaagg     240
gccgattcat catctccaga gacaatgcca ggaacaccct gtacctgcaa atgagcagtc     300
tgaggtctga ggacacggcc atgtattact gtgcaagagg cgactatttt aaccacttct     360
ggtttgctta ctggggccaa gggactcttg tcactgtctc tgcagccaaa acaacagccc     420
```

```
catcggtctt cccctggca                                                     440
```

<210> SEQ ID NO 146
<211> LENGTH: 146
<212> TYPE: PRT
<213> ORGANISM: Artificial Sequence
<220> FEATURE:
<223> OTHER INFORMATION: Antibody 132H4 VH sequence

<400> SEQUENCE: 146

Ser Trp Val Phe Leu Val Leu Ile Leu Lys Gly Val Gln Cys Glu Val
1               5                   10                  15

Lys Leu Val Glu Ser Gly Gly Gly Leu Val Lys Pro Gly Gly Ser Leu
            20                  25                  30

Lys Leu Ser Cys Ala Ala Ser Gly Phe Thr Phe Ser Asn Tyr Ala Met
        35                  40                  45

Ser Trp Val Arg Gln Asn Pro Ala Lys Arg Leu Glu Trp Val Ala Thr
    50                  55                  60

Ile Ser Ser Gly Gly Ala Asn Ile Tyr Tyr Pro Asp Ser Val Lys Gly
65                  70                  75                  80

Arg Phe Ile Ile Ser Arg Asp Asn Ala Arg Asn Thr Leu Tyr Leu Gln
                85                  90                  95

Met Ser Ser Leu Arg Ser Glu Asp Thr Ala Met Tyr Tyr Cys Ala Arg
            100                 105                 110

Gly Asp Tyr Phe Asn His Phe Trp Phe Ala Tyr Trp Gly Gln Gly Thr
        115                 120                 125

Leu Val Thr Val Ser Ala Ala Lys Thr Thr Ala Pro Ser Val Phe Pro
    130                 135                 140

Leu Ala
145

<210> SEQ ID NO 147
<211> LENGTH: 481
<212> TYPE: DNA
<213> ORGANISM: Artificial Sequence
<220> FEATURE:
<223> OTHER INFORMATION: Antibody 132H4 VK DNA sequence

<400> SEQUENCE: 147

```
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgtagat cgagtcagag cattgtacat agtaatggaa acacctattt agaatggtac     180
ctgcagaaac caggccagtc tccaaagttc ctgatctaca agtttccaa ccgattttca      240 ggggtcccag acaggttcag tggcagtgga tcagggacag atttcacact caagatcaac     300
agagtggagg ctgaggatct gggaatttat tactgctttc agggttcaca tgttccgtgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
a                                                                     481
```

<210> SEQ ID NO 148
<211> LENGTH: 160
<212> TYPE: PRT
<213> ORGANISM: Artificial Sequence
<220> FEATURE:
<223> OTHER INFORMATION: Antibody 132H4 VK sequence

<400> SEQUENCE: 148

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Phe Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Asn Arg Val Glu Ala Glu Asp Leu Gly Ile Tyr Tyr Cys
            100                 105                 110

Phe Gln Gly Ser His Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160
```

<210> SEQ ID NO 149
<211> LENGTH: 456
<212> TYPE: DNA
<213> ORGANISM: Artificial Sequence
<220> FEATURE:
<223> OTHER INFORMATION: Antibody 133A6 VH DNA sequence

<400> SEQUENCE: 149

```
atgaactttg ggttgagatt ggttttcctt gtccttgttt taaaaggtgt ccagtgtgag    60
gtgaagctag tggagtctgg aggaggctta gtgaagcctg agggtccct  gaaactctcc   120
tgtgcagcct ctggattcac tttcagtaac tatgccatgt cttgggttcg ccagactccg   180
gcgaagaggc tggagtgggt cacaaccatt agtagtggtg gtggtaacat ctactataca   240
gacagtgtga agggccgatt caccgtctcc agagacaatg ccaggaacac cctgtacctg   300
caaatgagca gtctgaggtc tgaggacacg gccatgtatt actgtgcaag aggcgactat   360
agtaactact tctggtttgc ttactggggc caagggactc tggtctctgt ctctgaagcc   420
aaaacaacag ccccatcggt cttcccctg gcacct                              456
```

<210> SEQ ID NO 150
<211> LENGTH: 152
<212> TYPE: PRT
<213> ORGANISM: Artificial Sequence
<220> FEATURE:
<223> OTHER INFORMATION: Antibody 133A6 VH sequence

<400> SEQUENCE: 150

```
Met Asn Phe Gly Leu Arg Leu Val Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asn Tyr Ala Met Ser Trp Val Arg Gln Thr Pro Ala Lys Arg Leu
    50                  55                  60
```

```
Glu Trp Val Thr Thr Ile Ser Gly Gly Gly Asn Ile Tyr Tyr Thr
 65                  70                  75                  80

Asp Ser Val Lys Gly Arg Phe Thr Val Ser Arg Asp Asn Ala Arg Asn
                 85                  90                  95

Thr Leu Tyr Leu Gln Met Ser Ser Leu Arg Ser Glu Asp Thr Ala Met
            100                 105                 110

Tyr Tyr Cys Ala Arg Gly Asp Tyr Ser Asn Tyr Phe Trp Phe Ala Tyr
        115                 120                 125

Trp Gly Gln Gly Thr Leu Val Ser Val Ser Glu Ala Lys Thr Thr Ala
    130                 135                 140

Pro Ser Val Phe Pro Leu Ala Pro
145                 150
```

```
<210> SEQ ID NO 151
<211> LENGTH: 498
<212> TYPE: DNA
<213> ORGANISM: Artificial Sequence
<220> FEATURE:
<223> OTHER INFORMATION: Antibody 133A6 VK DNA sequence

<400> SEQUENCE: 151
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca agtttccaa ccgattttct      240 ggggtcccag acaggttcag tggcagtgga tcagggacag atttcacact caagatcagc     300
agagtggagg ctgaggatct gggagtttat tactgctttc aaggttcaca tgttccgtgg     360
acgttcggtg gaggcaccaa gctggaaatc aaacggctg atgctgcacc aactgtatcc      420
atcttcccac catccaggga gcagttaaca tctggaggtg cctcagtcgt gtgcttcttg     480
aacaacttct acccaaaa                                                   498
```

```
<210> SEQ ID NO 152
<211> LENGTH: 166
<212> TYPE: PRT
<213> ORGANISM: Artificial Sequence
<220> FEATURE:
<223> OTHER INFORMATION: Antibody 133A6 VK sequence

<400> SEQUENCE: 152

Met Lys Leu Pro Val Arg Leu Leu Val Leu Met Phe Trp Ile Pro Ala
 1                5                  10                  15

Ser Ser Ser Asp Val Leu Met Thr Gln Thr Pro Leu Ser Leu Pro Val
             20                  25                  30

Ser Leu Gly Asp Gln Ala Ser Ile Ser Cys Arg Ser Ser Gln Ser Ile
         35                  40                  45

Val His Ser Asn Gly Asn Thr Tyr Leu Glu Trp Tyr Leu Gln Lys Pro
     50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser His Val Pro Trp Thr Phe Gly Gly Gly Thr Lys Leu
```

```
                115                 120                 125
Glu Ile Lys Arg Ala Asp Ala Ala Pro Thr Val Ser Ile Phe Pro Pro
        130                 135                 140

Ser Arg Glu Gln Leu Thr Ser Gly Gly Ala Ser Val Val Cys Phe Leu
145                 150                 155                 160

Asn Asn Phe Tyr Pro Lys
                165
```